United States Patent
Bhatti et al.

(10) Patent No.: US 8,686,219 B2
(45) Date of Patent: Apr. 1, 2014

(54) METHODS OF QUANTIFYING TARGET ORGANISMS AND CREATING RENIFORM RESISTANT COTTON PLANTS

(75) Inventors: Muhammad Bhatti, Ballwin, MO (US); Roy G. Cantrell, St. Peters, MO (US); Bill L. Hendrix, West Sacramento, CA (US); Patsy L. Kohlfeld, St. Charles, MO (US); Kunsheng Wu, Ballwin, MO (US); Jinhua Xiao, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 575 days.

(21) Appl. No.: 12/901,756

(22) Filed: Oct. 11, 2010

(65) Prior Publication Data
US 2011/0088118 A1 Apr. 14, 2011

Related U.S. Application Data

(60) Provisional application No. 61/250,235, filed on Oct. 9, 2009.

(51) Int. Cl.
*A01H 1/02* (2006.01)
*A01H 1/04* (2006.01)
*A01H 5/10* (2006.01)

(52) U.S. Cl.
USPC .......... 800/266; 800/265; 800/314; 435/6.11; 435/6.12; 435/6.15; 435/7.22

(58) Field of Classification Search
None
See application file for complete search history.

(56) References Cited

U.S. PATENT DOCUMENTS

| | | |
|---|---|---|
| 6,277,560 B1 | 8/2001 | Andrieu |
| 7,271,386 B2 | 9/2007 | Lawrence et al. |
| 2006/0006335 A1 | 1/2006 | Lawrence et al. |
| 2007/0061916 A1 | 3/2007 | Kovalic et al. |

FOREIGN PATENT DOCUMENTS

WO   WO 2009/104641   8/2009

OTHER PUBLICATIONS

Manome et al. (Plant Pathology, (2008), 57, pp. 887-896).*
Qiu et al. (Journal of Nematology, vol. 38, No. 4, (2006), pp. 434-441).*
Cullen et al. (Plant Pathology, (2002), 51, pp. 281-292).*
Toyota et al. (Soil Science and Plant Nutrition (2008), 54, pp. 72-76).*
Gobbin et al., "Quantification of the biocontrol agent *Pseudomonas fluorescens* Pf153 in soil using a quantitative competitive PCR assay unaffected by variability in cell lysis- and DNA- extraction efficiency," *Soil Biology and Biochemistry* 39(7): 1609-1619, May 4, 2007.
Nui et al., "Identification of molecular markers associated with root-knot nematode resistance in upland cotton," *Crop Sci* 47(3); 951-960, May 1, 2007.
Stirling et al., "Combining an initial risk assessment process with DNA assays to improve prediction of soilborne diseases caused by root-knot nematode (*Meloidogyne* spp.) and *Fusarium oxysporum* f. sp. Lycopersci in the Queensland tomato industry," *Australian Plant Path* 33(2); 285-293, 2004.
EPO; European Search Report for Application No. PCT/US2010052157, dated Jul. 16, 2013.
Powers et al., "A Polymerase Chain Reaction Method for Identification of Five Major *Meloidogyne* Species," *Journal of Nematology* 25(1):1-6, Mar. 1993.
Tilahun et al., "Nuclear ribosomal DNA diversity of a cotton pest (*Rotylenchulus reniformis*) in the United States," *African Journal of Biotechnology* 7(18):3217-3224, Sep. 2008.
Wang et al., "Identification and mapping of microsatellite markers linked to a root-knot nematode resistance gene (*rkn1*) in Acala NemX cotton (*Gossypium hirsutum* L.)," *Theor. Appl. Genet.* 112(4):770-777, Feb. 2006.

* cited by examiner

*Primary Examiner* — Brent T Page
*Assistant Examiner* — Jared Shapiro
(74) *Attorney, Agent, or Firm* — Dentons US LLP; Lawrence M. Lavin, Jr.

(57) ABSTRACT

The present invention is in the field of plant breeding and disease resistance. More specifically, the invention includes methods for assaying a location to determine the amount of pest infestation, or assaying a plant for its ability to resist infection, and using this information to make agronomic treatment and/or breeding decisions. The invention also provides methods for breeding cotton plants containing one or more quantitative trait loci that are associated with resistance to reniform nematode infection. The invention further includes germplasm and the use of germplasm containing quantitative trait loci (QTL) conferring reniform resistance as a source of reniform resistant alleles for introgression into elite germplasm in a breeding program, thus producing novel elite germplasm comprising one or more reniform resistance loci.

11 Claims, No Drawings

```
                         SEQUENCE LISTING

<160> NUMBER OF SEQ ID NOS: 384

<210> SEQ ID NO 1
<211> LENGTH: 643
<212> TYPE: DNA
<213> ORGANISM: Gossypium hirsutum
<220> FEATURE:
<221> NAME/KEY: unsure
<222> LOCATION: (1)..(643)
<223> OTHER INFORMATION: unsure at all n locations

<400> SEQUENCE: 1
gttncncctt cctacctcct gttacaattt ttggtactttt ctcttcaatt cccttgagtt      60
ctgaaatata gttattgatg aaacttgcta tctctttccc ggtcctgttg gccttcttat     120
gaactctctt gtttctttct tcccagattg cccaaagagc gcagcaaaag atcctacacc     180
gcgaagaagt gttctgttca aaaacccagg tgagccactg ttgaaactcc atctgagata     240
cgtgtaataa ctccaaaaat gataattctt tccatactga tattgagaca gggcattcac     300
ggmatagatg attcgtggtt tctgctgctc ttccacaccc agaacagagt gcattgtgta     360
atagcctttt atgtagcaag gtagtcattg taggtagata attccatgat attctccaaa     420
ctataatttt tatcttagaa gatagattaa gtagccaaag atttttgtaa aaattcctat     480
agtcggtctg taaagcataa gctttaggat caatttcatt gccctgtaat agtttatagg     540
cactatgcac cgtgaattct cctgaaggca ctctgctcca ggccaaaaaa tcatcgtgga     600
cctcttttgc taacggaata tagagaatct tctcagttac atc                       643

<210> SEQ ID NO 2
<211> LENGTH: 599
<212> TYPE: DNA
<213> ORGANISM: Gossypium hirsutum

<400> SEQUENCE: 2
tcggacaaag ataattagat gcagaaaaaa caattcacct tgaagagaac atgaaagaaa      60
caagtcttgg ggttggcata attttcaaca ggaggctgca caagaacaaa aacatttaaa     120
atcaatatat aagcaatcaa accagtaccc caagtacaaa ataaacagct ggatctgaaa     180
ttagtaacat ttctatctaa ttttcatgtt ccgaacaagt atacaatggc catataagca     240
```

-continued

| | |
|---|---|
| aatgggaact ctattttgtt caatttcatc atctttcttc aaccaaaaca ttgaggaaaa | 300 |
| cataaagttg aaatctttac cggctaaagt tggatcttgg gatctaattt gaataaccca | 360 |
| gagttgrcta ttgaaattgt gtttagaaat ggttagtttt catctgtttt atcaaaaacc | 420 |
| aatcaaaagg gtaccgttca aaatcgaaat ctctcacaaa aaactcagat ctaccagtca | 480 |
| aacagtccaa tacgtagaac aaatagttac aaatttgata aaccagcaaa aggaaactga | 540 |
| agggaaggag aaacagagag agggatcaac tcacctgact aaaatccatt acgggaaga | 599 |

<210> SEQ ID NO 3
<211> LENGTH: 960
<212> TYPE: DNA
<213> ORGANISM: Gossypium hirsutum

<400> SEQUENCE: 3

| | |
|---|---|
| tgcagagatc ttcttcagcc attcaatcca gttccaaagt ttatcatcat aaaatctgtg | 60 |
| gttttcttaa cctattggca ggtaaaatct tgtgtgcctg ttatttcctc tcatactcat | 120 |
| gcatgcaaaa agaagacaaa tcctttgttt ttggctttta gatactttta tctttccttc | 180 |
| tatttcattg catcacccctt tgttgcttt tggtgataa tcatcattta gaaatcttgt | 240 |
| tagtatcttt atrgcaaacc ttggggatgg tgaattctgg ttactggaat gcaatctttc | 300 |
| ctaacctgtt tgctgtccac attgatatca tcttcatgtt ttgttttata ggggaggctg | 360 |
| ttttctata ttttgctttc ccttttttata ctgatgtcta atcataagac agcagttcga | 420 |
| agttccggaa gtgctgtgac ggcattgtac aatgtattaa accctgtaaa atagaatgca | 480 |
| tgcctatatt gatggttatc cataacatct tgtgttgtga tggcattgta ctgtttgtaa | 540 |
| acctcatcta gttgcatagg tgctaaataa actcaaaaca tccttttctt ttatttcctt | 600 |
| ttgcagggtg ttatgttttt tcttgctgca aaatctggat ttattaagga tgctgatgca | 660 |
| gcagctcaat ttcaaaactt cattatatgt gttgagatgc ttctagctgc tctaggtcat | 720 |
| ctttatgcat ttccatataa ggagtatgct ggtgcaaata ttggtatgtc tcgtggtttt | 780 |
| acacgaagcc ttgcacatgc cttgatgttg aatgacttct atcatgatac tgttcaccag | 840 |
| gtgacccta cttctgttgc catttcccaa aggttcctct actggattct tcttcttttg | 900 |
| tttagggtta tttatggttt ttatcatatt cgcagtttgc acctacgtat catgattatg | 960 |

<210> SEQ ID NO 4
<211> LENGTH: 654
<212> TYPE: DNA
<213> ORGANISM: Gossypium hirsutum

<400> SEQUENCE: 4

| | |
|---|---|
| aatctgaaat atgtgacatg cccagatgag atagtatatc attcatactc taccaagtca | 60 |
| tggttcccctt aaaaaataat ataggaaacc atttttgtac ctgatcagat catgagtccc | 120 |
| accagatata gcatttgaga tggcttgtgt agcttgtatc caaatatcat atttatcatc | 180 |
| attttgaagc aaatgaagta gaggagcaat aatattagct tcaattatag cctgtaaaat | 240 |
| tcataccatt acccatcgtt tcattgcaca agtcaacgca gataaaacct taggttcaaa | 300 |
| attgatactt gtacctttat ttcctgttgt gawacttgag attgtccaac aagcaaactt | 360 |
| attgattctc ttttcataat tatttttcaa aggtttaaaa ggcatgggaa tgcctgatga | 420 |
| ttaatgatac actttgtagc aacaagattt gcccataaat aagaaaataa atcatcttta | 480 |
| acaactaaac ctaaaaaaat ctttagtcta attaagaggg ggtataaatg tgattttagt | 540 |
| gagaaaatta gttattaaaa gaaatgata tgataaatgg aaagagatac atattctagt | 600 |

| aagatcattt aaaaggaaaa gcaaattaaa taaagtgcct gatacctgaa tttg | 654 |

<210> SEQ ID NO 5
<211> LENGTH: 503
<212> TYPE: DNA
<213> ORGANISM: Gossypium hirsutum

<400> SEQUENCE: 5

| cacaagggca ggctcactag gaatactaca gtactgaagt attctctcaa cagatataat | 60 |
| tttattctcc atactgcaaa tattccatac cacccaagcc agcaacatat ttagattgag | 120 |
| tccatacgtc acagctaaac cggcaatagc taaacaaaag aaaaatgcat aaagtcattc | 180 |
| tcctagaaca tttgctatct agtagtcaat aaagctgcca atatgaatct gcatttactt | 240 |
| accaggatcg ataattccct caggtataga gattaaaaag aataaagaga aggcaaacat | 300 |
| aacagaagac agtaagtcca ggcggaagca cagccattcc attgcaccgc aaacatggaa | 360 |
| ttttggacga gaatacgagt crgtcagcac catattggtg tcttggaacc ttttctcttg | 420 |
| atcaaagctc cttatagttg ttgctcctaa aattgtttca gcaaaattct ggattactgg | 480 |
| agctttgcat actccaacca acc | 503 |

<210> SEQ ID NO 6
<211> LENGTH: 501
<212> TYPE: DNA
<213> ORGANISM: Gossypium hirsutum

<400> SEQUENCE: 6

| agatgctatt tggacatatg gtgactttac taaaagatta tcatcaggtc agcttcttct | 60 |
| tcttcttcat ttatcttaaa tgtggcaaat ggtttatatg ctgaataatc gagcatgttt | 120 |
| ctaataattg taactgacca ggaattccct aaaataaaca aggtgattac atgtgtccct | 180 |
| ggaagtgaga tcccggaatg gtttgatttc aaaagctcag gatcttccat aaacatccaa | 240 |
| ttgccttcaa agtggtacta caatagcagc aaaaactttc caactttcgt tgtttccact | 300 |
| gttgtttctt tccaagacta ttctggcgac agagaaattc tcattagatg taaatgtcgt | 360 |
| ctaaaatccc gtaatggcga ctgtcatgac cttagttgtt ctttcttaac ttggacaaaa | 420 |
| cgaattcctg gaagcgaatt gactggrtcg aatcacttgt tcctcttata taaaacttgt | 480 |
| ttctgtgatg aggatgatga g | 501 |

<210> SEQ ID NO 7
<211> LENGTH: 673
<212> TYPE: DNA
<213> ORGANISM: Gossypium hirsutum

<400> SEQUENCE: 7

| catcttctgc aatgatgata gtcaactttg gtactcgatt caggtgctac aaaccacatc | 60 |
| accaatgatg tctcgacact cagtcatctt actgaataaa caggtatgag ccaacttttg | 120 |
| atcggcaatg gtgctcctgt tcctattgmt catgtaggga gatcctctat tggtacttgt | 180 |
| agtaggatat tacatcttaa acatgttttt acatgttccc tatgtctgta aaaatttgat | 240 |
| ttctgtagca cagtttactt gttttttgaa tttcatccct ctcgttgttt tgtgaaggac | 300 |
| atcaagacag ggaaggtttt gctagtaggt cacattcata aagggttata tcgatttaac | 360 |
| acatcaccac aacaaagaag ttttgctggc tttgatgagg ctttcaata tgcacatact | 420 |
| actaagattc aagcttgaga caccttctgt tctgagttcg acttatggca caaaggcttt | 480 |
| ggccatccct gcacaaaaat tctttttcaa gttcttcgaa gttgtaatat ttcactgaat | 540 |

| | |
|---|---|
| aaattcacac cacctagagt gtgtgttcct cgtcagctag gaaagtctca taagctggtg | 600 |
| tttgataatt ctaagactgt atatacttcc ccttttcaac ttgttgtgtc tgatttgtgg | 660 |
| ggacaatcac cta | 673 |

<210> SEQ ID NO 8
<211> LENGTH: 748
<212> TYPE: DNA
<213> ORGANISM: Gossypium hirsutum
<220> FEATURE:
<221> NAME/KEY: unsure
<222> LOCATION: (1)..(748)
<223> OTHER INFORMATION: unsure at all n locations

<400> SEQUENCE: 8

| | |
|---|---|
| aaagaggaga aaagagcctc ggccttctcc ttgcgtcgat tctaacgatg ggaaagaata | 60 |
| tcccggcgac gcaaccccg ggtttgggta agttttcctt ctttctcctt ttatttattt | 120 |
| tgttgaaaaa taaatttaaa agagcagaaa aataaataaa aagaaaacc raaagaaaaa | 180 |
| agagaaccca aaaatgagat ttaaaatcaa cttttattt ttttgctttt tacttctgaa | 240 |
| aaaatttgcc tgtaatacaa ttttttttg tataccgaaa tcccctctta cattcggttc | 300 |
| ttccctcggc ttatatagcc gaatacatag aaaatatttt ctgctctctt ctattgtttg | 360 |
| ttgttttcg ctctctttcc ttctgctttg tgtgcttctc ctttgttttg caggtaacgt | 420 |
| cagagtaggt gagcagaggc gatgggacgg gcgtctgttc gggcgcaaaa tgcgctgaca | 480 |
| ccacgtgggg gagggaggta cagcgcctag cataggaacc ctagggtttt ttctttttt | 540 |
| ctgataaatt tgggctttgg gttaggttta gttgggcttt ggattgggtc atagttcggg | 600 |
| ctttgtatt gggctgtgaa ttgtaaaagg tatgggttga gcctgttttg tttgttcatt | 660 |
| gggcccggtc taatttgggc atttacaata tgtatgatgc aaatttcctg annnnnatnn | 720 |
| nnntagannn tagtatgcaa nnnnngct | 748 |

<210> SEQ ID NO 9
<211> LENGTH: 591
<212> TYPE: DNA
<213> ORGANISM: Gossypium hirsutum

<400> SEQUENCE: 9

| | |
|---|---|
| gaatgcctca cttgcctaat ttattgcttt gactctttgt tgtatgctat ttgactttta | 60 |
| accaccatcg aatataaata tataattatt acaaatagtt tagaagatta ataattata | 120 |
| tttatattca acccttttga atattcctcg gaaagttctt tgaacaaagc acaaccatg | 180 |
| aaggttacct gtgctcgtca agaagaaacc acgaaatttc actgtttcac accaaagctc | 240 |
| caccaccaag tttcccaatt ctaaccaatt ttgattaaac tgagattttc ccaatgcaag | 300 |
| tgacccaatt ctaaatggtc ttyttatgtt ttcaagccaa gctccgagca gcaaggttgg | 360 |
| tggtccaagt tcagaccta accaaaacag ctacccgagg ggctctatcg atcggaatgg | 420 |
| acacactcat tcgtagacgc agaaggtctc gttgtcatct tcgctttcct attctacttc | 480 |
| tgctactttc attgatcgga agggttatcg gagtcgtact tggattgttg atcaccagaa | 540 |
| tgttgatgag aaggcaataa tctacatacc ataggttgga aattgtatta g | 591 |

<210> SEQ ID NO 10
<211> LENGTH: 615
<212> TYPE: DNA
<213> ORGANISM: Gossypium hirsutum

<400> SEQUENCE: 10

```
tttgaaaaat tttatgcaac tgctccacct acaaaataga aagcagatct caatcatttc      60 attttttgcag caaatatgta ttttaagggt cttaaagcca tgttatatgc atggacatgt   120
cattactcag tttatttgca caaatatgta tatatgtttt ggcttagaac tctaaaattc    180
tacatgcttt gtaggaaatc tttcatttaa atgataaaaa cacacctcag ttcttcctgg   240
cataataggc ttkccagcat ataactcagc aagtatgcaa cctgtactcc atagatccac   300
agcggtacca tagtaagtgg ctccaagtaa aagttctggt ggtctatacc aaagggttac   360
gacacggctt gtcatgggtt gactttgatg gggatcataa aagctagcca gaccaaagtc   420
tgcaatcttc aagatgccat tattgtcgat tagaaggttt gaacccttta tgtcacgatg   480
taggacacca cggctgtgac aatgatcaag accacacaaa agttgttgta tgtaacactt   540
cacctgcaca atagatcaat aaattaaacg tcaggataac ctttcaatgg aaagtgcaaa   600
attctgtatt tgcag                                                    615

<210> SEQ ID NO 11
<211> LENGTH: 635
<212> TYPE: DNA
<213> ORGANISM: Gossypium hirsutum

<400> SEQUENCE: 11
gttactagct gtttagctaa tggattgctt gaagccgttg tgaagaaaag gtaactgagg     60
aggctcaaag agcaatggtt atggcttttt cttcccctg cattggactt agtactatgc    120
atatgcttta agcatgagtt tagaaaaggt gaatatccaa cttgatattt aatgaatctg   180
ctacttttgg aatcaatgaa atagatttgt cttatttttg aaatcaaata gttggtatta   240 tattttttt tgttgaaata taaaacaaaa aattacataa acttattcat aaacagaatg   300
cctctagtac tgtctccttg tagascttct ttaattgcct ctagaaattc ttcgaacata   360
tgcaaatagt cgtcatcatc tgttcgagct actgccttat taaattctct agggacatat   420
ttcaagaact actttttttc atttgataaa atctattaaa ttcgtctaac cagagtggaa   480
tttaatcttt caattttact gtcttcaata attttacaa cctcaaaatt atttttttgg    540
ataacgaact catcataatc ttgtttatta atcaattaaa ccatccaaaa tgtcccaaaa   600
ttcctcaagg aatacaggac acttcccaaa aaaaa                              635

<210> SEQ ID NO 12
<211> LENGTH: 598
<212> TYPE: DNA
<213> ORGANISM: Gossypium hirsutum

<400> SEQUENCE: 12
tgggaacaat cgtaagagga tggcatcctt agtaacgcca ttgatcttga aagtgtcgca     60
aatctctaga aagttatcca atgggcatt caaatcttta tcttgcaacc catcaaactt    120
aacatattat tgtatcattt gaattgtgtt cagatttagc taaaaattgt ttacagcaac   180
agtcgatctg acgatactcg attcagcccc aattcaagtg tgcttagcat aatcatacat   240
agtacgaaga gcaggagttg caagaagcag twgattattt tgattaccac tcatctccat   300
ggtaatatca ttttttttct tgatcatcta ctatatttgt tgattttgcc ttacttctct   360
aaccttttta tgattttgc gagcaatctt ttcaacttca ctataaaaaa ttaatgattc    420
caacgagttt cctctagtca taaaccaaaa gaacctgtca gaatcaaacg aatgaacaaa   480 tttgaatgt aaaattaaa ttaaaaacaa aaatattaaa attaaaaaat agctaaatta    540
atagaaataa aattttccta atattttagt ccctgtcaat agtggcaaac acttaatg     598
```

<210> SEQ ID NO 13
<211> LENGTH: 585
<212> TYPE: DNA
<213> ORGANISM: Gossypium hirsutum

<400> SEQUENCE: 13

| | | | | | |
|---|---|---|---|---|---|
| gcgccgatct | acgtctatca | gcagagacga | acagccccgg | gcttcaaagg | atgaccattt | 60 |
| cdgtcgtggg | atcccttcta | aaccccgatt | tcgacgaaat | gaaggggata | cgacggccaa | 120 |
| ctcgcaaggt | aaacctctct | tttgctttct | tttttgttt | ttgagataga | tttcaaaata | 180 |
| aaagaaaat | agaggcgtaa | aaatgaaaac | agggaacaac | ctttgcagaa | tattcaactt | 240 |
| ctttgtattt | gattcctctt | tttttgtgt | aatctgttcg | tagtcgtatt | acaatcgaaa | 300 |
| atcaaaggct | tcatagccga | ataactaaag | aaaacaacaa | tttttgtcct | ctgcttttgt | 360 |
| attggcttgt | tgctgctttc | gtttgttttc | ttttgcaggt | acggagcacg | gggctgtgcg | 420 |
| ttggcgctcg | ggtacgggtc | taggctaggg | tacgaggtg | gtacggtcgt | tgcgaggctg | 480 |
| ttgcggcgca | agagggtgac | ctagggttcc | cgaaagtgtt | gaagttttttg | ggcttttttgg | 540 |
| gctattcggg | attgggctta | tgggctagg | atattaagtt | tggtt | | 585 |

<210> SEQ ID NO 14
<211> LENGTH: 530
<212> TYPE: DNA
<213> ORGANISM: Gossypium hirsutum

<400> SEQUENCE: 14

| | | | | | |
|---|---|---|---|---|---|
| gatagcttgg | aaggatctct | ctcttatatg | taagagcaga | gaactttgga | ttatataaat | 60 |
| attaaaatag | taaaaattta | tattatattt | taattattac | tttttcataa | tcatgctaat | 120 |
| ctataattct | taagtgcata | aaacacaaac | cgtccgacac | attaattaaa | gtaggctcca | 180 |
| ctttgtcaac | tctcaccttc | ttgattcctt | ttgggaaaag | catcactgct | catctatgac | 240 |
| ctcatgcgtt | attattggaa | aaagaaaaag | tgggaaatgc | atagagaaat | tgcttagaaa | 300 |
| cctttgctgt | tccctggaaa | tttgagctgt | ttttctttct | tgttgctat | atacttattg | 360 |
| tttctcgttt | cttctgggg | tattrggtgg | tttgttttct | ggttttgaac | accaaactga | 420 |
| gatacctttt | ttcttgtcgt | acgttgtcat | gttgtcgtta | ccttcaactt | cctcatctat | 480 |
| ttctaaaatg | aaatattgta | gagctgttat | ccaccgtaga | cattctagac | | 530 |

<210> SEQ ID NO 15
<211> LENGTH: 699
<212> TYPE: DNA
<213> ORGANISM: Gossypium hirsutum

<400> SEQUENCE: 15

| | | | | | |
|---|---|---|---|---|---|
| ctaatcactt | acctacctcc | attaattaca | ttgaaacttg | ataacctata | ctagcacawt | 60 |
| ttgtaaagct | gatttatcag | ctcaaatgtc | aacaaaatta | catcaagtac | attaccaacc | 120 |
| tagttctaaa | caaaccaagt | tacaaaatgt | taatttaaag | taacaaaatt | agcagcattg | 180 |
| tcttcaactg | cgacctgcat | ggctcgggca | gcttgttctt | cttcttggct | gcttcatgtg | 240 |
| ctgcatgaag | gccaacttca | acactcctct | ttggcctgca | tactgcatac | ttccagctta | 300 |
| gctcgcaaat | ccataaacct | tgacacacaa | agaggctttg | tcaagatgta | agcaagttga | 360 |
| tcctctaaac | tgcaatgaat | cagtttcact | tcttgtgctt | gtttcatttc | tctaacaaaa | 420 |
| tgaagcttaa | tgttgaagtg | atttgtcctt | ccatggaata | ctggattctt | tgcaattgca | 480 |
| acatcagatt | ggttgtcaca | cataatctct | gttgcttccc | tttagtgaag | attcaaatca | 540 |

```
gctaagattt tccttagcca actggcttgg ttgacaactc ctgcagctgc cacatattct    600
gcctctactg tcgattgaga acaacaaat tgctcctttt cactctaaca aaaaatggat    660
gaaccaagag taaaaacata tcctgaggta ctcttcatg                          699
```

<210> SEQ ID NO 16
<211> LENGTH: 738
<212> TYPE: DNA
<213> ORGANISM: Gossypium hirsutum

<400> SEQUENCE: 16

```
tatattcccg aaatctcttt tactttcaca gtaaaccttt aaaaaaccga aatttacaaa     60
tcaaaactct gaacaaaatt acttaaatgc taagaaaatg agccaamaac aaccggagag    120
gccccaagag ccaatcaatt acggagatat cttctccgga aaaggcgagc ttgccgagaa    180
gacagtggca cctaaagatg ttgccatgat gcagaaggcg gggaactccg tgattggtca    240
aacccagaag ggtggtgtcg atgcatctat gcaatttgca acgtcgaaga atgagagttc    300
gggattggtt ggccgcgaaa gagtcagtgc tgattctggt gtttatatta agagaccga    360 gtcccctaga aaacgtgtaa tctcggagta ctttggtaaa gaggtaagag gagcaatcta    420
tagagagagc tctaatttaa tatttgttac cgctttttaa ttatagttaa tatatcaaaa    480
aattattctt atattataga aatgtctgtt tgaattaggt tgagctgagc ctaagtactg    540
agtctatact tagtaccaag tattaattta tttatgtttg tcaaaattcg atctaattca    600
acatataaat tttaaatttt actcaaattt actataatat ttatatgact aacttaaata    660
tgtttacatc atccattttt taaaatttaa tttatctttt tttattaatt tttaaacata    720
aacaacatta aaatattt                                                 738
```

<210> SEQ ID NO 17
<211> LENGTH: 557
<212> TYPE: DNA
<213> ORGANISM: Gossypium hirsutum

<400> SEQUENCE: 17

```
aaacacgaaa ggttgttgat ttgttttatt cctttctttg aaactacgca tatattcata     60
catatttcat tttatttgt gttctatgta tatatataag atatattaat aagttttttt    120 taaaaaaag aaaaaagcga aaaaactaaa attttttacct ttttcgaaaa tccggccacc    180
gtgtacggtg gtcggcggcg gtggcgcatg gcggtgctgg agtctcaccg gaaatcccca    240
ggctgagaga gagagagaga gagagagctt ttttgaagag aaagaaagaa aaaatgaatt    300
tttttacaaa tttttttgct tttataacaa tatgaaatga cgccgttttg cattaaagac    360
ccagggcata aaatgacgtc gttttgtcct gggtcggatt gacctgaccc atactcgctt    420
agaatccgcg tgttttgac ggaagggcta attgcacttg tagcccttcc gcttttttat    480
agctttgtaa tttaattttt tgtattttta attttgccca aaatttttat ttttgtttca    540
ttttggtcct ctgctgc                                                  557
```

<210> SEQ ID NO 18
<211> LENGTH: 450
<212> TYPE: DNA
<213> ORGANISM: Gossypium hirsutum

<400> SEQUENCE: 18

```
cgctgctcta attgtgtcca gctcaaccac aacaatatga tttgagctgt caccgttgtt     60
tgattgattg aaaagaccaa gatactggct gggaagagct ccaggaattc tattattagg    120
```

| | |
|---|---|
| cragattaaa aaggctaatc catggccaga caaagtaggg tattcctccg gtacaattgc | 180 |
| aaaaaagaat gtggtcgaaa aagagaaaac actaccattt gtggagttct tgaattggat | 240 |
| tggattcttg tagaagatgt gacctgttga ttggattgta gaattagtca gttttaagag | 300 |
| cccacttgaa tctacgcctg caactccatc aacattcaag taaccattga aactgaactg | 360 |
| accctgattg atatctgaag atgcaaggtt caggaggaaa agcaacacaa gcatgatcaa | 420 |
| gcaagacatc attacacaca caaaaaaaaa | 450 |

<210> SEQ ID NO 19
<211> LENGTH: 548
<212> TYPE: DNA
<213> ORGANISM: Gossypium hirsutum

<400> SEQUENCE: 19

| | |
|---|---|
| tgcgtgataa attatatcca ttttccttga aagataaata tggtggctgt gaaaccaata | 60 |
| atttacggac aacagattgc ttagatcata acgtgatgg gcttcatgtg tatttcaatg | 120 |
| ggcatagcct taaggtgaag aagtgtggtg ttagaatagt gtatgagaaa gatttggaag | 180 |
| aaataaaaga gttgcagtgc catacccctc aatcttcacc aaattttgaa cacatccacc | 240 |
| aacactctgc tcacaacgat ggatcagtag gtagcacttc tgacattaaa caagaacgta | 300 |
| atatctccga ggaagcggag gaagaggggc agcaaccaaa actgttgcaa aaattttca | 360 |
| attttataat gggccaatca gggaagaagc attaactgtg gtaaactact taaccaatct | 420 |
| tgtcctatta acttttttc acatctttya tttaatgtga tcaatctaga cttacttacg | 480 |
| atccttctta cataccacaa agttataaat cttttactca tattcaacag gagctcatat | 540 |
| tccgtaaa | 548 |

<210> SEQ ID NO 20
<211> LENGTH: 415
<212> TYPE: DNA
<213> ORGANISM: Gossypium hirsutum

<400> SEQUENCE: 20

| | |
|---|---|
| gcccttgatt cggtttgtat tatcttctaa tccaatctat ttgctatctc cgaagtttgt | 60 |
| tgggagaaaa gcttgaccgt attatgcgaa cgttttggtg gggtcatgat ccgaatcaga | 120 |
| ggaaacttca ctttgggaaa ccgaaaacca atggtggact tagtattcac agcatggagt | 180 |
| gatgcattac ttagtaagca ggcctggarg ttactgactg aaccccaaca cttcgccata | 240 |
| taggaaaata tcatcgacac caacatttct ttaatggaag agtttagttg aaggagacga | 300 |
| gatggttgtt tgagtggtat tgatatctaa atttgcaagg tgcaaacaac tctttttaag | 360 |
| tgactaggtg atggatgatg ggtagacaaa cttctaacc cacgcttctc acact | 415 |

<210> SEQ ID NO 21
<211> LENGTH: 646
<212> TYPE: DNA
<213> ORGANISM: Gossypium hirsutum

<400> SEQUENCE: 21

| | |
|---|---|
| ttctggagcc ttctctggat attccctcca ggtacttctt taaataaggt tatttgtttt | 60 |
| ggaagtgctt gaaaaaacaa tatttcaaat taggctgatt aggtataacc aataatgtta | 120 |
| ttacttgtaa acaattgagg ctgcaaaata caactgtttg aagcaatatc aagaagccgg | 180 |
| tttgatacat tgtgaagaaa taacacgact tggagcagtt aagttttgga tcttgcattt | 240 |
| gtggatggac ttatccatta gtgtttacat accataggga atttgtttgt aacaagtttt | 300 |

```
cttgggcttg tgtttacagt tgcttatctt ggtctttgga tatgatagtc ctttgggatg      360 cctcctttc ttaaatatta tttataataa gttttcttag gcaccatctt tagtgttttg       420
tcatattggt tgcatattgc taatcttcat taatcttgat taggtgatgg agtcccatca      480
agcaggcaaa ttggacactt ctggtactgc taaggctatt atttcttgct ttcagaaatt     540
gggggtgtca tttgacatgg atcaggtgtg tggctcttac atattcttaa ttgtaattga     600
aagagaaatc aagttctttt ttcttattgg ttaggggctg gggagg                   646

<210> SEQ ID NO 22
<211> LENGTH: 645
<212> TYPE: DNA
<213> ORGANISM: Gossypium hirsutum

<400> SEQUENCE: 22
taacattttg attgctctaa ctttaaaaaa ttctaaaata ctcattaaat tatttcaaaa       60
tttttatttt tatttcaaaa agaaaagcat aatgccttgt tgtttaacaa taatgccaaa      120
atctmattag catgcagtag aagtagaggt gtttaggttg gagtctagct caattaaaat     180
tttaggaatg tttgttaagt ttggatttga ctttaccttaa aaattgatc taaaattttg     240 gtcaagctcg atgtaaataa aaatattaaa atttcaagtt cggccggccc atattcaaat    300
tttttatata atatttttat aaaaataata taatacataa aaaatactaa aaacattaaa     360
ataaatgtct cccagcaatt tgaaaataaa ttttaaaaat atatgtgctt aaataacact     420
gagataagtg caatttaaca gacaaatacc tttaaaatag taacaaaatt aacaataaaa     480
taagaattat ataatatcca aacaataaga acaatatagt aacaaaataa tagtaaaatg     540
atagcaaaat agtgagaaaa caataatata gcagcaaaac aataaaaaac aacaagaaaa     600
caacattttt tttatttttg tagattcata cgagctgagc ttcag                    645

<210> SEQ ID NO 23
<211> LENGTH: 611
<212> TYPE: DNA
<213> ORGANISM: Gossypium hirsutum

<400> SEQUENCE: 23
tcatgttaga gggtacacac ctggtatgat tttgatgtga aaccacacca gagaccacca       60
gcacctaaaa gaatacccaa cacctttta gcaatcaaat tgcaaatcca tcaatactaa      120
accgaacagc gtacacatac ttaccactat caaaccggat cacgcgcaca gattagactg     180
attgagcgaa aactgcagtc tcaactcctt ctcctgcaca aaacgtttac agagaattat    240
tttcccttac aacwtacact aagaattcaa gtgaaaagga gaaacccccat agcttactga    300 agatgaaacc tatcgacaag tgaaagcccc cacttatctg atcacacgaa aaacactgaa     360
atcccaaatt gcatgtgaag aacaaaagga gagtacagat tgaaaaggga aaattgaaag    420
aagaagagaa tagtggagaa aagcaaaac gtacgtcaga aattttggaa gagagagaaa    480
cgaaattaga aaaaaataaa ataaaataaa caacaatatc tatcctaacc tctcattctt      540
tcccactcga actagtaagt ttattttaat atgagttaat aaagaatatt acataagcct     600
acccagtaga g                                                         611

<210> SEQ ID NO 24
<211> LENGTH: 300
<212> TYPE: DNA
<213> ORGANISM: Gossypium hirsutum

<400> SEQUENCE: 24
```

```
aagtttagtc aacttctaaa ccataaagaa cattagcata cttttcaatt gggtccccat    60
ctgcaaaata cctttccttt atcttcaacc aagcgtgcaa tgtcaacaaa ctatcggaac   120
cagcttgatg actcttccca attgcacgct ttactcccaa atctgtagac gcacgatcga   180
gacctccrtg taatccagcg cagaatttca tcaagtgttt gacgtcgtag attctgtctc   240
cgaagaacac tcgcacgagt tccaaaaact cagtgagttg gtcaggcaat aacccaccgg   300
```

<210> SEQ ID NO 25
<211> LENGTH: 631
<212> TYPE: DNA
<213> ORGANISM: Gossypium hirsutum

<400> SEQUENCE: 25

```
atgttaattg ccataggctc aaaatgtgct ttgcatgctg ggtttcccat aacattgcac    60
tgagttatga attttttatg ctaattgca tgttaaggat tgatgaaatt ttgtacaaaa   120
tattaaatca aaacagataa aaacctttct atctgtaatg catgttttca tctgcacagc   180
aggcatgtgc acagatcaca aaccatcaca acataaacct ttggtttgct attatctatg   240
catttcccga ctgttcattt tcttgaagt atttgtcttg cgattatgaa tatatgaccc   300
ttcaatacat ggaaaaactt agaaaacaat taaacatacc cgtatctgaa actgcccaa   360 atccaagtaa catgggctcg aatatctctt attatattgg ttacttcccg ttggtcttcg   420
taactctttc aagatatgct tttacttatg agattatgtt gttttagttg cttttcttag   480
attttgatcc aacattaaat ggatgtttta tgtgtttcaa gggtgctttt tgagaaactg   540
aatttaaatt acgaggaggg tgagagatgg attgtgaatc tcatccgaaa ctctaaactt   600
gatgcaaaga ttgattcaaa gactggaacc g                                  631
```

<210> SEQ ID NO 26
<211> LENGTH: 658
<212> TYPE: DNA
<213> ORGANISM: Gossypium hirsutum

<400> SEQUENCE: 26

```
ccgatgggaa agccactgga gaggcatacg tggagtttgc ttccgtcgag gaagctaaaa    60
gagcaatgtg caaggataag atgatgatag ggtctcgata tgtggagttg tttccttcaa   120
caccagacga agctcgacga gcygaatcaa gatcgaggca gtgaagaggt cctgttatct   180 gggttttga tatgtagtct ttggtttgta tgtttgtcat tctagcctga agaaatgcat   240
gtcaacccat atttaatggg ttaatcttct tcctatgtgt gtctctgctc tcaaaatata   300
atctcctaat cctattaggt taaatatgat cagtatgttg ttgatgtact ttttttgtt   360 tttcttttag atatttgaat tttggttta aggatataaa atatattta gataaatatg   420 tagacttttt acctttcaaa ttcatgctca tggttgcctt cgggtggttt cattgttcat   480
tttgcatgtt gtggtattgc catggcatta aatagagtcc ttcttgatcg aagattttaa   540
agattattat ttgttacatt gggtggtttt aattccacaa ggttatttat tttttaaata   600
ctagttaagg ataaaaaaat ccaaagggcc gatggattgg gtttcaatcg gattaaaa     658
```

<210> SEQ ID NO 27
<211> LENGTH: 578
<212> TYPE: DNA
<213> ORGANISM: Gossypium hirsutum

<400> SEQUENCE: 27

```
gaaaaattat ataaaaattt gtgtcggtat tatcttcact tgacccttgc tttaccatt    60
```

```
tgattcgccg aacaatccaa gaatttaaca cccacaaggc cagaacaatc gcctatcacc      120
gccgtagccg acacccaaaa tgaggaagga agcggcgccc tcctccgtcc cttccgccgc      180
cgcaggcacc accactttgg ggaagctatt catttgcttc gagaccaaaa cattagtgac      240
cacattgctg gcacttactt tagttacgtt cttatggaac ttacctcctt actaccaaaa      300
cctcctctcc accacccgtc cttgctccgc tccgataacc tccgtttccg tcaccgcttc      360
cgccgcatcc gtcaccgcca rtttgatctc caccaatgtc tcaatgcctt acaagccgaa      420
tccggtagct aagaagtaca cacggcgac accacctaaa cccaaggacc caaacaagcg       480
ggttttcgag tcgtacggga acgcggcgg tttgtttgta cagatgggtg cttacagagg       540
aggaccgagg acgttcgcgg tggtgggatt agcttcca                              578
```

<210> SEQ ID NO 28
<211> LENGTH: 652
<212> TYPE: DNA
<213> ORGANISM: Gossypium hirsutum

<400> SEQUENCE: 28

```
atgaatgctg acgacttgct cgatgatttc tctaccgaaa ctttgcggaa agatctaatg       60
gctgggaaca agctgatgaa agaggtacgc cttttctttt caagctcaaa tcactttgct      120
tacggtctca aaatgggtca gaaaattaag gccattaagg cgaggttagc ttcaattgaa      180
agtgaggcca acactttggg ctgcatggtg cgtgaccgcc yagtggaaac ctctttcatg      240
attaaaaaga gacagcgaac acactctttt gtgagtaaag ataaaataat agggagggat      300
gatgataaag cggctctttt aaaactcatg ttagagtttg aaagtgaaga gaacgtttac      360
atcattccag ttgtggagtt tggaaggtta gggaagactg cattggcgca gtttgtttat      420
aatgataaaa tggtctatga ttattttcaa ttgaggatgt gggtgtgtgt ttcagatgtt      480
tttgatgtca aattaatttt agaaaacatt attaaatcta taactggcca agtaccagat      540
caaaatctcg aaattgacca attgcaaaaa caacttcgag ataaaattgg tggaaaaaaa      600
tatttgcttg ttttggatga catttagaat gaagagaggg aagaatgcgt ta              652
```

<210> SEQ ID NO 29
<211> LENGTH: 585
<212> TYPE: DNA
<213> ORGANISM: Gossypium hirsutum

<400> SEQUENCE: 29

```
tacctcccag ttacaaaagt cccaactttc catctcaacc gtccatcaat cttgatcatc       60
aaaaaaacac tcccggccat ctattcagca cccaatgcga cggaatattc cggtgagatc      120
ggtaccatag taccatatat tataggtgac caaatattga cctcawtatg gccttgtcca      180
gagtgttatt tcttggttcc cgttagaagc gtaaacgtcg agccggtcgt aataaacacc      240
gatatcgtcg tttgggttac gtgaacggac tgtgatttga agtttgaag tgagggagtt       300 gacggtggtg gcgttgaagg cgtagacggt ggtgtcgagg agagtgaagt tggatttgct      360
gggaggaagg attgcccata tgagtaagat tgtgatgaga atgaggagga ttagaataca      420
agcgatgact cggcgaaaaa atttctggcg ggatttgtgg tggtggccgc cgcagtctta      480
gctaccagac atggtggatt tggaagttat tgggtttctt tttggtgatt gtgtgaggat      540
ttagtgatgg aatagtattc agtgtgtgct attagctttc ttgtg                      585
```

<210> SEQ ID NO 30
<211> LENGTH: 592
<212> TYPE: DNA

<213> ORGANISM: Gossypium hirsutum

<400> SEQUENCE: 30

```
acagaaatag aaatgattgc agtctgtcta ttttctttcc ttttattgga attaaatatt      60
gatgttttt ctcgaaataa agaaatttat gcatgtcata tgggctttga tatcttctca     120
ttgttgagaa cttggttctg aaatggttac tatgttctaa ttgttttttt tttctgattt     180
ttagggaaaa cacgggcaag agatgctgcg ctaaatgcya tccagtcgcc tttgttagat     240
cttggtatag aaagggctac tggaattgtt tggaacataa ctggtggaag tcatttaacc     300
ttgtttaagg taacgcgcca tctccgactc tctcagtgtg tctgcgtttt cttgcggaga     360
ctttatatat tatcttgata ttgagcgcaa aattgttgat tattcgtaaa tggagcactt     420
ccctgtagga gaagagtcat tgaagcccaa gcggccccac catatctgat acctgcattc     480
ttgagtaaca gacaagtgaa taattggaaa tagtatagta atgaatacta ctttgtcatt     540
gaaatgttat acatgggaaa ccttgattat attgactgat ccacttgggt tc             592
```

<210> SEQ ID NO 31
<211> LENGTH: 579
<212> TYPE: DNA
<213> ORGANISM: Gossypium hirsutum

<400> SEQUENCE: 31

```
tgcatcacag aacattgaat tttagggttg agagaagaaa gagtaaaaac caacaacgat      60
tcctcaaccc atgtctttgc cttcgcctcc tatcgccatt ctctctacac ctttaagtcg     120
cactttcagg agggagagat ctgtcattgt ttggcatccg gagagtgttt tcttccactt     180
tctgagacgt gcattatatt actacagtag tcttgatcgt gaaattcagg taagttcttg     240
gtattgtttt gttgagtcta atttgttatg gttttcgttg atcgaatcag ttatagacca     300
tcagatttgg gattcaacaa agtacaagta ggacgtgcgc aatggacatt gacacrgagt     360
ttgagggtct gaatttgttg tttaagtctt aaactagtaa tggattttcc ttttgcctga     420
gttctttgtt aacttaatta ttgtaaaatt gatgtaaact tatatgagaa gttgctgctg     480
ttagctctttt ccataagcat tttccataag catcggaagc ttaaaaggtt acttttaacc     540
tgtttatcat cttttctttt ggactgtaat tgtatgata                            579
```

<210> SEQ ID NO 32
<211> LENGTH: 620
<212> TYPE: DNA
<213> ORGANISM: Gossypium hirsutum

<400> SEQUENCE: 32

```
tcaaagttcc atccaacata gaagttcaag cctgaaagtt ccaccattaa cgatttcttc      60
ttgtcaaccc catcttcaac atcctgcaaa tgcatctgtt ccattgagct caattctatg     120
ttggaagcac cattggctac tggacttcca ttaatttcaa gtccagacgt gtctacactt     180
ccactcaatg tctccatccc aacactgtta ttttctcaat tttccaacct ttgtctaaag     240
caaatttacc ctcctgtttg aaaactgacg atcttcatcg gttgattggg cttttgaaaa     300
atatatcttt ttcttttttg gtacctttca aagtccattc aagcagcaaa gcaaacaagc     360
aacttattca cagatattgg atcattacgc atgataacgg gatttattwg tgttcatcgg     420
attgatcatt tagcccaata gactttgagc ctaaacccaa gatctgtcct gaattaaaag     480
aaataaaaat tggatttcaa tttccaaaat taaaaaacaa ctgaaattat aacatcaaat     540
ttgcattact gccaccaagg caccaatcaa gatttgaacc cttcttcttt tgacatggag     600
```

-continued

```
aaggatgact gttgcagtta                                                  620

<210> SEQ ID NO 33
<211> LENGTH: 574
<212> TYPE: DNA
<213> ORGANISM: Gossypium hirsutum

<400> SEQUENCE: 33
ctttactatt cgcggtggct gcctctttc ttctctacac gtgagcagta ctgaaatttg        60
cagactttct tttcttcatt tcctagtcgt ttcgagtttc tttagtttat aattttctat      120
cagttgtttg aagaaaacat ttcggtgttg ttgatttgct tgctctttat gttttttatt      180
tgattattaa acgactcatc atctgatctg agttaaaatt ttcagatctg tacagttttt      240
tttgaatagt ctccdagcaa ctatgggcca tcaacagctt gcgagggagg catcttaagc      300
acaatatgac taaacgaacc tccattgttg gcaggaagca agaaaagaag tcgggagaga      360
gttttcgatc ggttcccttt agcttctcaa aacttatctg aaattctttc ccggcttctt      420 ttcttgctt cgttttattg ttcgtttgcg ttgtgcttca gatgtcgcac atccaggctg       480
tttgaagttg tttgtaggcc aacctaatct ccatggaaga aatccagtag ccgaagttga      540
ggtgaagtgg agattgttcg aaaaaacact ataa                                  574

<210> SEQ ID NO 34
<211> LENGTH: 789
<212> TYPE: DNA
<213> ORGANISM: Gossypium hirsutum
<220> FEATURE:
<221> NAME/KEY: unsure
<222> LOCATION: (1)..(789)
<223> OTHER INFORMATION: unsure at all n locations

<400> SEQUENCE: 34
ttcttaaaca aaccctaaac cttaatttct ctcacatttt caatggaatt tnnngggtaa       60
attttccttt acatcttaca tttctttcag ttaaaatttg ttctttgaat atttgtttca      120
attgcgaaat tagttgaaat taataattat ttatgtttga ttatcgatta tttacgtttc      180
tttgaaaatg ckaatcgtat gttcagatgc tgtcttctag taaggatttg atgtttcagg      240
ctgtttcttt tgctaactat ttttcttta atgatatt tttttatctt tgattttgta         300
tgtaagagtg cggcatggaa ttatatatat atatacatgt tctcccagat agattcattc      360
actcttttga attagaattt aggtttggta tttctattga ttttgttctt ttaaattgtt      420
ttcttagttt catttcacgt ctgattaaag gaaaattact tatgttgtac aatttttct       480 caagcatttc tctgtaaaat ttccctataa tttactcatt atgaatattg aagggaaaaa      540
aagaaaatga taccttttt tccttgttaa atcgtaattt ctttggacat tattaagggt       600
ttgaaataat attttatagt ttgatgtttt gaattggatt accctgttgg aaacctttta      660
gaatatgttc tatctgctac tactgttggt attgcgtttc atcatttggt gttattgtag      720
ttttttacat ctcaatgatg attgcttgtc aaatattttt tgattgttac atattttgcg      780
atttcatgt                                                              789

<210> SEQ ID NO 35
<211> LENGTH: 687
<212> TYPE: DNA
<213> ORGANISM: Gossypium hirsutum

<400> SEQUENCE: 35
taaggctggt caagacacat tgatttcagt atataatata catcattcct cacaggtgct       60
```

```
tgcttatttt catcatactc gtaatttttt ttctttgaat ttttcctgg ttattactcc    120 tatgttgttc cgtttcttca tttttcttaa aatgcctgtg tttgatacct tgtccgatg    180 tatataacct aaaagacccc gccaaatata tgggaatact tagaaaaaat tttgaaaata    240
tccaaatcct ctgtgaaata cctcattttc tgttgttcgc agcctacgta tcaaattgta    300
catgcactat ctctatgctg aatttgctga ctgcataacc gatcaacgtt tggtttcctt    360
caaatagaat attctaagtt tgaaaatagg gagttttacg attcctacca tttgttttct    420
tggacagcaa taagcgatat tccgtctttt tcttctttcc aggtctggga agagctgaa     480 gagtttgtgc ccgagaggtt cgacttggaa agctcagtcc ctaasgaatc aaatacagat    540
tacaggtacg aaaaacaacc gtgttttact agttttctcc ctgtccctga tatccttccc    600
acatttgcat tacatactct tcatcatatt aatacggtag aacatcttca ggttcattcc    660
gttcagcggg ggtcctcgta aatgtgt                                        687

<210> SEQ ID NO 36
<211> LENGTH: 620
<212> TYPE: DNA
<213> ORGANISM: Gossypium hirsutum

<400> SEQUENCE: 36
tagtgagggt atggtgaaac gtcaggatgt atgggtcacc tcaaaactat ggtttgcttt     60
tgtgctttaa tacttttctt tataagttct tctcaatgga gtccgttact ttgcatatct    120
aatatgtcat tgcgttgtac gtttaggtgt actgatcact tgcctgaaga tgtaccaaag    180
gcattgcata aaactctgca ggatttgcaa cttgattwtg ttgatctcta tctagtatgt    240
cttaacactt actttattga aatgatatat atgtatatat gacatttgtg gtaactgcga    300
tgaatgttga agatacattg gccagtgagt gcaaaaaggg gagcaattgc tgtgaagggt    360
gaaagcctta cacaaccaga catcccagct acatggaaag caatggaggc actctacgat    420
tccggtaagg ctaaagctat tggagtgagt aatttctcgg caaagaagct cagggatcta    480
ttggaagtgg cacgtatacc gcctgcagtc aatcaagtgg aacttcaccc tgtatggcag    540
cagccaaagc tgcatgaatt tgtaaatcc aagggaattc acttgtcggt aagaaaacag    600
gccgcttcag gttcatatca                                                620

<210> SEQ ID NO 37
<211> LENGTH: 669
<212> TYPE: DNA
<213> ORGANISM: Gossypium hirsutum

<400> SEQUENCE: 37
gggtgactaa tgaagaacat aggaaggga ttttcccaat ataaaagaa acaatgtaa       60 tattgtggac caagtcaaat aaaaccccac aacatgtaac gtaatgcaca ctaccatcac    120
aaccaccact aaaggcacgt caaaccgccc ccaaagcaca cgtatacgcg caatagaacc    180
ggcgtttaaa gatgcatagc ctcggaagtg gtcgaccgat tccatgactc catcactatc    240 cttttacct tacctagtcc tcaccaaaat caatcattta aaagtataat aataatattc    300
tgatattaaa tgaaaacgg gdatgttgta ataaaacctc gttcatttca ttaacatttt    360
cactttcaac aagatatatt tattcccaga ttaaaaaga gtaaccccctt cctatagctt    420 taactggttt tccctaagcc caaagtaatg aacaaaatct ggctgcaacc ccatatatat    480
atatcatcat cattcctgga aactagaaaa ttattgattt tcatctaaac ctaaccctaa    540
aaacctatat atgtcttcta tactactaat atagtcaaca accatatgca aagttgagtc    600
```

| aataagtcca atcttgtggt aactggactt cacggttgat cccttgctga ggccttgagt | 660 |
| tatgcttgt | 669 |

<210> SEQ ID NO 38
<211> LENGTH: 656
<212> TYPE: DNA
<213> ORGANISM: Gossypium hirsutum

<400> SEQUENCE: 38

| aagagacagc tctagagtcg acctgcagaa agtgcaaatc catttcaact ttaccttgaa | 60 |
| cttctctatt tatcaaatac aattatattt tgatgaatta aggagccagc tcaagtccgg | 120 |
| attgcattta gctccatacg aggttaggca atctgtcttt ttttattgat tatgctttgt | 180 |
| tattttcgt ttttgcktttt tttgtactta ccatttgtaa gagagtttat tggctttagc | 240 |
| atctcttatg ccgaatctga tgcgatttac ttgcgagttt cagaacttgt atatcatctt | 300 |
| atcgaattct aaaggctcca ctgttgctcc cccatatcg ttcagtcaaa agttctgctt | 360 |
| gctgtaggga atcctccatc aacgccaaga ttaaagcaac tagctcaaac catcacgggt | 420 |
| tctcattcga aaaaccttgg cctaaaccac actgtatttg gtaaagttaa gcaagttcgc | 480 |
| cttttcttcca ttttgcaaca ttctcttcac ggaggtgacg gcagttcaaa ctcacctgct | 540 |
| ccttcacctc atcctgtcca cagtaatcat catcatcacc accaccacca ccatcaccac | 600 |
| caccatcacc atcaccacca tagtgctgat ctagctcctg caggtcgact ctagag | 656 |

<210> SEQ ID NO 39
<211> LENGTH: 574
<212> TYPE: DNA
<213> ORGANISM: Gossypium hirsutum

<400> SEQUENCE: 39

| atctagcatg actataactg caccaggcta tattacttgg actcgggaat ragtatagta | 60 |
| tatgggtata tatccaacaa gagcatgctc aattttttcta agttttttttc acatgttggt | 120 |
| ggatacctac atccaaatat gtatcaaaca tgagtgtcgg acatatatac cttaacaaaa | 180 |
| atgaagagtt ttaagtaatg tatgcattgg gtagaaatga caggtttgtg tataaaaata | 240 |
| ctgaaaacag ctggtcaagt gaataatatt ggtaccgggg tattatcacc caaaaaagaa | 300 |
| agcttgaaat gttcaaaata gaaataccat tttatgcttc tccaacattc tctcttacat | 360 |
| gtcaaataaa cttcacaaag acttaaaaca taagtatcga tttgttatat aatgaaagca | 420 |
| aaatataaga acctgaaact aaaccaattc tctgaagcag tgtatctgat gaccactagg | 480 |
| tcgatcatac aattcgactg aacactaata ctaataacat aaaagaccag caaagtaaca | 540 |
| gttccaaagc aaatcaaatt tgtataattt attc | 574 |

<210> SEQ ID NO 40
<211> LENGTH: 708
<212> TYPE: DNA
<213> ORGANISM: Gossypium hirsutum

<400> SEQUENCE: 40

| aagagacagg tcaaatattg gtatattcta tcccttagct gctgcaatgt attattgttg | 60 |
| ttgttgaatg ttttttaaaat atggaattaa tgctaatagc agcatttcgg aataaaaatc | 120 |
| cacgactaag ctagatttca tcgatgataa aatgttcttg ttgttacggg ttgattgttt | 180 |
| tgaacaaagc attatgggtt gatttatta ttattgattt gattgttgaa agttttttgg | 240 |
| atgcaatagg ttgttagggg ttgaaccttg atcatcggaa ctaaagtcta gcattctact | 300 |

```
gacaaaccac ttgattgttg aaactttgct gaaatttctt gttgatttaa tttctttccc      360
aattcattct actttccatg agcatttat tctggctttc ttcggagact tgcttggttt      420
cctgctcttc ctaaacattc ttttgtcatt tggattaata acctgcctat tattagtgct      480
ccataaacga ggcgagtgga gataagggga aagaaggga gggaagagtt ccagaagatg      540
acattgaagt cttaataaaa taaacatgta ataatatatg ttaggaacaa ccatctgttg      600
aaatcttttg ctctttgcyg cccaactgta tgtcataata gattgctgga ttttccgcaa      660
gttctcatca agttgatctc tctcttttc catatatatc tgtctctt                    708

<210> SEQ ID NO 41
<211> LENGTH: 174
<212> TYPE: DNA
<213> ORGANISM: Gossypium hirsutum
<220> FEATURE:
<221> NAME/KEY: unsure
<222> LOCATION: (1)..(174)
<223> OTHER INFORMATION: unsure at all n locations

<400> SEQUENCE: 41
agttaccccc tggcccatga aggtangcag tatttcttaa tatgacacag cattttctta       60
cactgttttg ttctggcctt aygaaaaata aaaagatgag atatagggtt tatagcggtt      120
nagtacaata tatttgatta tttatgttat tctttttccc gagtagcctt ggtg            174

<210> SEQ ID NO 42
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 42
aagagacagc ctctagagtc gacctgcaga acagcattgg cataacaact gcaaataaa        60 aacaacaatc aatccataaa acattagctc ctattatttt atgtacttac aaacaagtca      120
tccatttaag gaaactccaa aacacgcatc cycggattac aagtagaact actgaatcgc      180
gaagtttagn taatgaacta gatatacttt ttaattaaca ttcaagaata agtatagcat      240
gcttaaacta taagtcaatc atcattattt cttttctttt gttaatagga acatatatat      300
cctacacgtc atgttactcg gactcaggtg agtgtgttat atgagggatg tgtccaacat      360
gagtatcttt ttttacatgt aattgatggt cctncaaaac atgtatttga agtctccaaa      420
atcatgtcca natatgtgcc aagcatggat gctttcaaga aaatgaana ccatactcca       480 agtaatatng caaatatggt agaaaatagg accataaagc aataacattg atacctgttc      540
cctatattta gaagtcccct cggtgataag tcnaaggctn cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                  814

<210> SEQ ID NO 43
<211> LENGTH: 281
<212> TYPE: DNA
<213> ORGANISM: Gossypium hirsutum

<400> SEQUENCE: 43
```

| | |
|---|---|
| atattggcta ttgaatcatg taaacctcaa gaactcatgt gcatcttcct ggcttccatc | 60 |
| acccatctga caattaatac ttcggatgtg cgaaaggatc ctactagaag acaagggacc | 120 |
| cccactctct cttaacaaca tcacatgttg ttcaagctca cacayaagac accaatcttt | 180 |
| cccataacct acaatgaatt aaaaagttat gctatgcatg tggtcaaaca gtgacatcat | 240 |
| tctcatgtac aaataacaaa caagtgaaca taaaaatttt t | 281 |

<210> SEQ ID NO 44
<211> LENGTH: 908
<212> TYPE: DNA
<213> ORGANISM: Gossypium hirsutum

<400> SEQUENCE: 44

| | |
|---|---|
| aatctgcact actcggtgac aacgtgaatt cacagttctt tgggtacatt aataagcagg | 60 |
| ctatcatcaa acatcacct ttagatcata caaatatttg tccattaacc actgttgtat | 120 |
| ttgctaacag ggattgttct atggttgatt cctctcaagt ccrtctggct gatatgagaa | 180 |
| gtacagagaa gagaattcct cgtaaatcca acaaagacat gttgcaaaga gaggatgcaa | 240 |
| ctatatttga ttcttgtgag gaaacctcaa ggactagagc tagtagttca gcatctaata | 300 |
| atatttcttc gaaagaggct tttataaggc ataaggttct ttcattattc tttttaccta | 360 |
| gaacatttta tcttttattt aataatatgt agtttagtaa catcgagcta ctgcatctag | 420 |
| agagatacta cgagtcctcc gtcccagatt ccatcgccgc ggccatctgg ttcaccggta | 480 |
| ctaccaaaaa gtctcatgct tacgttactg ttattgatgg ttttattatt tttgactacg | 540 |
| aaggccccgg tcgtgcttct ggtttccatt cccatcatca tattgatgat aaatctcctc | 600 |
| gtgctctgcc ataagaactt ggagtccgta tcatggtgaa ggtaaggtaa cgctgtgatt | 660 |
| cttgctcaaa aaacagaccg aacgcgttcg agtaattggc tcgtccaacc cggcagcatt | 720 |
| catgagtcgc tcgttcaact gtccctcgga gacacggtcg agaagtacca tgcatggttg | 780 |
| ccctccgtcc ttttttctc tcagtcccac ccagaaagat acggctcagc caaaaaaaag | 840 |
| tgaacgcccc tgcgcgagcc ttattttatt agtaaggtaa gctttggct ccctaaagac | 900 |
| taaaaaaa | 908 |

<210> SEQ ID NO 45
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 45

| | |
|---|---|
| aagagacagc tctctagagtc gacctgcaga acagcattgg cataacaact gcaaaataaa | 60 |
| aacaacaatc aatccataaa acattagctc ctattatttt atgtacttac aaacaagtca | 120 |
| tccatttaag gaaactccaa aacacgcatc cncggattac aagtagaact actgaatcgc | 180 |
| gaagtttagn taatgaacta gatatacttt ttaattaaca ttcaagaata agtatagcat | 240 |
| gcttaaacta taagtcaatc atcattattt ctttcttttt gttaatagga acatatatat | 300 |
| cctacacgtc atgttactcg gactcaggtg agtgtgttat atgagggatg tgtccaacat | 360 |
| gagtatcttt ttttacatgt aattgatggt cctncaaaac atgtatttga agtctccaaa | 420 |
| atcatgtcca natatgtgcc aagcatggat gctttcaaga aaaatgaana ccatactcca | 480 |
| agtaatatng caaatatggt agaaaatagg accataaagc aataacattg atacctgttc | 540 |

```
cctatattta gaagtccccct cggtgataag tcnaaggctn cacactggaa aaattttaca    600
aattcttcrt aaggaaacag catctgagac agcacaataa cggatcatag tcagagtttt    660
cctttcacaa ttcaagagcc aaatgaaact aaaagggatg caatagatat tgatcatata    720
taaacataaa gaaagtatga aactgacctt tattttcttc cgtctctcgc cacaaagcgc    780
agaaaaactg ctcctggcag gctttgttga cttc                                814
```

<210> SEQ ID NO 46
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 46

```
gtgtacttta tatcagaaga tttcaaccag tagatctcca ataaacttaa atggttttga     60
atgttgaatg cngaagcaaa atataacata cagtgggctt tgagtygaca ttatccataa    120
caatttctcg tattttttcct tgtccaattt caaattcgga ccgcagatct ctggtaggat   180
tagtggcatt atgcacagca gaaggagcct ctgtaatatt tgattgnaag tttaacttac   240
aacttgggtt gagaatatta acctggaanc aaaacataac agatnaaaat aganacaaag   300
cgatcaacaa agttggagaa acgaggctaa aatgtctcta cctcaca                347
```

<210> SEQ ID NO 47
<211> LENGTH: 578
<212> TYPE: DNA
<213> ORGANISM: Gossypium hirsutum

<400> SEQUENCE: 47

```
ccgtgattga agttgacagg ctagcaggaa ggcaggaagt tcttgcattc ctagcttcag     60
aagggttcat gaattgaacc ttaaccaaat ccaaaagttt ctttatcttt acaccaatac    120
caactgcctt gatacgagga gagcctacat tataatccaa gaaagaatct cccttactgg    180
taagggaact tgtgttcata tgtggtttac tggaggccca tattgacata cgcctgaccc    240
cacttaagtt cattccagat aacttacagc tagttaaaac aatgcaccct aatatagcaa    300
caaaagttac cctttcggtg acattacttt gcgaaaacca gctttcccaa gttttattct    360
ggtttactcc aaattttctt tccaactgaa cagaagatga actgacattg cttccaccgc    420
tatcgtcacc cattaccaaa ggactctgca aatcagttgg tcctaattgc ttaacagctg    480
acacaatatg tagagaagat ttcatatggg gaagggaatc ctcaaaatct ytcctctccg    540
atgcaagagc agtaggtagt gatctatggc ctagattt                            578
```

<210> SEQ ID NO 48
<211> LENGTH: 749
<212> TYPE: DNA
<213> ORGANISM: Gossypium hirsutum

<400> SEQUENCE: 48

```
cagatacaaa gcaatagcga agaaatggga gacggtccga gtcgaggaac ttgaaatcga     60
ggaggatgag ttcgttgttg ttaactgttt gtatcgtgct aagaatttgc ttgatgaaac   120
cgtggcggta catagtccra ggaatcttgt tctcaacttg atacggaaga ttaatccgaa   180
tttgttcatc catgggatta ttaatggtgc ttacaatgct ccattctttg taacacggtt   240
ccgagaggcc ttgtttcatt tctcatcaat gtttgacatg ctcgacgcga tcgtgcctcg   300
```

```
cgaagattgg gaaaggatgt tgatcgagag agagatctta ggcagggagg ccttgaatgc    360
cattgcttgt gagagttggg agagagtaga gcggccggaa acagtcaaac aatggcacgc    420
acgtatccta agggccggtt ttctacaaca gccattcgaa cgcgagatag tcaaggaagc    480
attcgagcga gtccagacgt tttaccacaa ggatttcgtg atcgacgaag ataaccggtg    540
gctggtacaa gggtggaaag gcagaataat ctatgccctt tctgcttgga aacctgataa    600
ggatatcgaa aatttaggtt gcgttccacc cggttccaga actcgttcgt tactgtacat    660
atcaacggag gcacacaaca aagccacgag ggtcggtagg ggactaaaga gacaatactt    720
tggatgtctc gagatatacg tctcggaac                                     749
```

<210> SEQ ID NO 49
<211> LENGTH: 443
<212> TYPE: DNA
<213> ORGANISM: Gossypium hirsutum
<220> FEATURE:
<221> NAME/KEY: unsure
<222> LOCATION: (1)..(443)
<223> OTHER INFORMATION: unsure at all n locations

<400> SEQUENCE: 49

```
cactatacac gcgcacacat atatataggg ttcgaattcg gtacacctag caatacaatc     60
ttttaactcc acaaaggagt taaaaaaact gccacatgtc ctattttttat tattatttta   120 ctacaccttta agggtatgta ttacctattc aaccttgctb atggagacta aacaagccac   180
tagcagaatt ttccatggat acacacacag gccagtccaa taaagagtaa catactgtgg   240
caatatatga cnaatncacg agcgcgcata tatatcataa tgacatattt gtcatactat   300
ggaagattct ttttcttttt taaatnacaa attagattat actgggcaac ttaaaccgtc   360
attcaggctc accaattaac aaccaataaa atgctaaaac caacactata tgtatatctg   420
agaaaatgca tacacatata aat                                           443
```

<210> SEQ ID NO 50
<211> LENGTH: 209
<212> TYPE: DNA
<213> ORGANISM: Gossypium hirsutum

<400> SEQUENCE: 50

```
aaatacgggt attgttcgct tttctctttt caagtttttc tatgcattta gagagtcctt     60
gtaggatcat atccccataa caacgtctag ataagmatca aaacacggat acttcaagaa    120
aactaaagaa tcagagtaat atagtttcca atgaactaaa ccgattcatg ttgacttcaa    180
ctaaggcata cttgcagtta gacacatac                                     209
```

<210> SEQ ID NO 51
<211> LENGTH: 432
<212> TYPE: DNA
<213> ORGANISM: Gossypium hirsutum

<400> SEQUENCE: 51

```
tggaatccga cattgcttcg tgttttggtc ttgtatttat tcgtgaaatt tgtgaatgaa     60
ggggttactc ccgaatctat gaatccatcc gttgatgaag tagtagacga ggaagaagaa    120
gggcttccgt ctcctccttt agacatggaa gctctctttg ctcaacckac agcaatggag    180
ctctcgcagg tctttacttt tttaaccttt acgtgttcgt gttttttctt ttaatattat    240
gcttgtgact gattggaatt attttttccccc tttgttgccg gtccgtgtta tgtgaagttt   300
ttcgatggca tggatgatga tggaagtgag ttgattttttt tcccttttcta atgcttagat   360
```

```
agattgtgag cctttagatt ctcaattttg atctggggaa tgttgtttca gatcctggaa    420
gcagtgggga ct                                                       432
```

<210> SEQ ID NO 52
<211> LENGTH: 581
<212> TYPE: DNA
<213> ORGANISM: Gossypium hirsutum
<220> FEATURE:
<221> NAME/KEY: unsure
<222> LOCATION: (1)..(581)
<223> OTHER INFORMATION: unsure at all n locations

<400> SEQUENCE: 52

```
gtttgattca gttgaaggtt cgagagataa gataaccacc tggttcaaag aagtaaatca    60
caatttaggc aaaaatgtaa tacaaagtac ttacatcata acaaaaaagg atgaaatatt   120
atactttgct cgtacgaaag cctatctcat caaaaatgtc attttcaagc tgcaagatat   180
tgtctcccag aaaagaaacc ggcttctyaa ctttaaaact tgctactata tcatgatctg   240
gacaataaaa taaccaaatg ttanatcact tccataatta taaattcaat attggtccaa   300
ccccacagca aatatngaat tgccaatcct acggaccagc ttcgaccaga aaaccgtata   360
taaataacta taacaattat tatatgaatg cagagattaa taaccaagtt gatacatcca   420
aaaaaattct caaacaata ccgatgacaa gtacttatat gcaatatacg tgatataaca    480
tccaatagta attgatctat gaaatgttga acaattcggt cagaaaaccg tataaacaac   540
aacaatggtt atatgaatgc agagatcaat aaccaagtta a                       581
```

<210> SEQ ID NO 53
<211> LENGTH: 516
<212> TYPE: DNA
<213> ORGANISM: Gossypium hirsutum
<220> FEATURE:
<221> NAME/KEY: unsure
<222> LOCATION: (1)..(516)
<223> OTHER INFORMATION: unsure at all n locations

<400> SEQUENCE: 53

```
gatttagctt gtccagtctg ctgcaaaatg aaatgtcgga gcaatgtaga nncgaaaaca    60
tataaaaagg agaggaaaaa gaatgaaaaa acaacctgtt ggttactttg atcttttgag   120
gaagtcactg tttgattctg ttgttgcaat tgcggcacrt atgtaacgga atgagaacct   180
ccaanagtgt tgccgttcat ctgaccacgg tttggcctgg tttgtcttgg agcagtaggg   240
aactatcaca tggtatagta agtactcata ttcgtacagt tcgaaccgct aacgtacttg   300
tatataaata cacataccag gggaagtgat gagtattgaa agactggtct ggttggtggt   360
gcaaagccat tagctctcca tcctggcctt aaacctaaag gttggtgcat catcccgggc   420 cttagggta cttgtgaaac aaagccagtt ggagatgcgt agtaaagcgg agggtatcct    480
cccgggagaa caactgttga aggccctgct aatcct                             516
```

<210> SEQ ID NO 54
<211> LENGTH: 624
<212> TYPE: DNA
<213> ORGANISM: Gossypium hirsutum

<400> SEQUENCE: 54

```
ggccctcagc gctggtacct acgaggccaa cagctgctgg tagaggccgg ggcattaggt    60
tgatagattt agaccccgaa ccttgtcagg ttcttccagg ggcttacct ttggttgctg    120 ctgaaccggc ggcttttaac cgagtagagg tggtggcaga taaagatatt gcaatggagg   180
```

```
gtaggagygg tgacaaaata gttggagttg atgaagaagc tagtacaacc ccggttcctg      240
aaagggtatc tccaaagtgt ttgccatatg tttccttttt aaatatattt attttttact      300
taaatcttcc atagtaagtt gcttattccc gggacacctt acttttggca agaaaaccgg      360
ttaaatacag tttttttcg tatccttcat gacagcattt caagaatgct tcaactaatt       420
ggataatcat ttctacttct attgttcatg aaagtgaggg aaccagtgtt ttaactttct      480
taccaactat aacgtacgta gttattttgt tgtttctctc aatgcatacc attttattta      540
tttgttgcag gtacaagtgg gtaattctcc tgtatataag gtagaaagga aactgggaaa     600
gggtggtttt ggccaggttt atgt                                             624

<210> SEQ ID NO 55
<211> LENGTH: 839
<212> TYPE: DNA
<213> ORGANISM: Gossypium hirsutum
<220> FEATURE:
<221> NAME/KEY: unsure
<222> LOCATION: (1)..(839)
<223> OTHER INFORMATION: unsure at all n locations

<400> SEQUENCE: 55
aagagacaga ttgtatggat gtttattaga ggtatacata tatcggatca aaacgggtcg       60
atgttcaatt ttaaaatatt ttttatgttt aagcttgttt tgaagtcgga tcgatccacc     120
caaaagctca ttttactatt aaaaaaataa atataaatga aatgcaccaa tagtaaagta     180
gtttgtatct aatgaaactt taatttgaga tttcaatctt accatttaac taaaaagact     240
atttattcca ctgaaattgg gtttccagaa atattaactt aatttccttt taaccagcat     300 gccattttc attaaccaaa catacccctaa ataatatcac agaatcagaa taaaaccata    360
ggcaaacatt tcaaacctat attttcaatt aaaaaataac ataatatttt gaatacaaat     420
taggataaaa cttgcgcaaa aaacaaatgg aacaaccgca ccagcgatgt gtaaatgtat     480
aataataagc tgtgagactg taatctattg ggacatgtat tcatgccaaa aaaccctaat    540
tagatataaa tattattccc atcatagaaa gaatagggtt aagttgaaaa aaatgattaa    600
tgagaaaaaa aaataaagaa tctagccatc attagttggg cctttcaatt gaattttcag    660
gcattgtcat cgatggcggt atrttctgga gggttaccgg caagccaacc ccaaacaccg    720
ctcgaaccct gcctctgcnt tgcatttaag gcagcttgtt cagatgcagc tttcagtcgt    780
tgcaggaatt caagttcttt ttctagtgtt tccattgtct gaagcttttt gtcgcagtt     839

<210> SEQ ID NO 56
<211> LENGTH: 481
<212> TYPE: DNA
<213> ORGANISM: Gossypium hirsutum
<220> FEATURE:
<221> NAME/KEY: unsure
<222> LOCATION: (1)..(481)
<223> OTHER INFORMATION: unsure at all n locations

<400> SEQUENCE: 56
gggaatatgc gtgttttata tatcaaaatc ggacaatttg ttctgccagg aaagaacttt      60
tcattttatc aaagtaattt gaataagtct atcaaatttc aaataagaca ttaagatgaa    120
agaatgaaaa tgttaacctt aagatataaa ckctttgctg gaatggaatg aataaataca    180
tcagtnagag cctgaagaat ctccggagca catgatgata atgccttgat attttttggtt    240 gcagttttct ttgaataagt gnctggaatn ctgagctcta atttagagtc tcccattaca     300
gtattgtttg attcatcagc atcctctcca gatctaagta tatttttgtt ttggttgaca    360
```

```
agaatctaca gaaaaaataa caccactata gatattatac aagagaaaag aaaacaacna    420
acaaaagtta tttggaaaga ggatcaacgt aaggttctag gacttacaaa actaatggta    480
a                                                                   481
```

<210> SEQ ID NO 57
<211> LENGTH: 603
<212> TYPE: DNA
<213> ORGANISM: Gossypium hirsutum

<400> SEQUENCE: 57

```
aagagacagg gctacggatc atcgcagccg tggctcgttg ccatgagatc aagctcaagg     60
tttcattgcc ttactctgtt tctcctcttt tcgctgtatt ttttcggttt ttgtttgttt    120
tatttcaatt tcttaagttt ttatcaaatt caatttattc ttcttgtttt agttgcttga    180
gcttcaatac tatgtttgga atagtgtttg gatgatattt gagatgctga atttgactgt    240
tatttcctgc atctgaaaac gtaatgattt agcaagaatt ttgtggtatg atcattcact    300
ctgagataat arttcaaaat tcaaccaagt gagatcgatc tcgatttctc tcaatttgtt    360
tttaaattca aacctcaagc tgttgtagtt tcttcaatgt ttacgtttac ttttcttctt    420
ttgcaattac taattatttt gaatttattt tctctgagca tcgtatatga ttcctttat    480 tatgatttga ttgcaataat attcaattta ttcttgatta tgtgcctttg atttatgttt    540
tcactctcgt tagattttga atttcaaatt tcgattcaat atatctccac gatcagttca    600
agt                                                                 603
```

<210> SEQ ID NO 58
<211> LENGTH: 756
<212> TYPE: DNA
<213> ORGANISM: Gossypium hirsutum
<220> FEATURE:
<221> NAME/KEY: unsure
<222> LOCATION: (1)..(756)
<223> OTHER INFORMATION: unsure at all n locations

<400> SEQUENCE: 58

```
ctctagagtc gacctgcagc tctttaagta atctgttatt tcaactaaca gacagtaatt     60
tgcagcagca attatgatta tgcaattgtt ttcagccaaa gaaaaaaagg aaaagcattt    120
taaaaatcaa tataaatgat ctcaagaaat aacattcata tgtcacgaag ctagaacatt    180
cacggcccct gacgcatgtt ctagccccgt gacgcataca tgttsaagct taaaacaaag    240
tagtaagatg atgcgataca tgaatggcca attctatata aacacnagga agaagggaca    300
aaatttacta ttttatttag ggtgatggat caaatttatt ttccatcttt gcaagtgtgc    360
aaattgtgct tctaatttta ttgaaaatgt caaatttaca attggggtat tctacagaat    420
ttttcttgcc attatcatta accttttttta accaaattca ggaacttggg aataataata    480
ttcgaaagag gacacaataa gaaggatatc atcttggatg aataaatgca aaaagaagtt    540
aatgaaatca aagatagcat gcctgtaact ccactaaatc tattgcagag cttttcaaca    600
agtgattcca tttgtttgtc ctgcaaaata tagtagatat caatatatca tgttaacgag    660
attataaaga acagtagttt cagttttata tcaacaatgt aaaccttctt gatggaaccg    720
attaagaact gcatgatgtt gcagaaagac actttc                             756
```

<210> SEQ ID NO 59
<211> LENGTH: 459
<212> TYPE: DNA
<213> ORGANISM: Gossypium hirsutum
<220> FEATURE:

```
<221> NAME/KEY: unsure
<222> LOCATION: (1)..(459)
<223> OTHER INFORMATION: unsure at all n locations

<400> SEQUENCE: 59
cattaacatt aagttgacct tgttcatgtt aacagcaata tatacgcatt gtcatataga      60
aattcatggt gntttntttt ttaatggatg aattgtagaa gatgattcct catttatcct     120
ttaccaacta attgcgttac ttttgcaggt tttactggca tagatgatcc ttacgaacca     180
cctttgaact gtgaggtatg tgtttarttg aatacggaaa ttattagcgg cggcattgtg     240
aattaaaatt aggctattat tctgatataa atactgctag tttatgggta atcgttttcc     300
tcctttatag atagaactaa atcagaaaga tggagtttgt cccacaccta gtgccatggc     360
tggggaagta attacttact tggaggacaa aggatatctg caaggttagc gaccaattct     420
cggttgtcat ggtcgagcat tctcagtcga gttcaattg                             459

<210> SEQ ID NO 60
<211> LENGTH: 826
<212> TYPE: DNA
<213> ORGANISM: Gossypium hirsutum

<400> SEQUENCE: 60
actatatcga aacgaaaatc tcagaatgaa tcatagggtt gcaacttttg aaattatgtt      60
tacagtcatc tttgggaaga ttaagaactg tgattaaacc tttttaacct ggttgttggc     120
ccaatgatta aacctcagga tttcgagaca ccgaaactga gctggtggca atcatgttat     180
ggtttagcca ccactatcaa gaatttaaat gcagtaaaag gaatcgatac aaaacagaga     240
tttgaaacat agaaagtatt tgcttacagc taggagtagt caatttaaga gtcctgaagc     300
agatatcgta taaagcctca ttatcaagaa ccatgcactc atcagcattc tcaacaagct     360
gatgaaccga aagagtagca ttgtatggct cgacaaccgt atcggaaacc tttggcgagg     420
ggaacacgga gaacgtaagc atcatcctat cggggtactc ctctctgatc ttcgagataa     480
gcaatgtacc cataccggaa ccagttcccc cacccaatga gtggcatacc tggaaacctg     540
caatggcaga tcrgatccac aattgtcact aatgatagta agatgttca gtggctaaaa     600 ttaaacggaa catatcgatt tataacatcc ggaacctaaa gaaacaatgt cttcaccttg     660
caggcagtca cagttctcag cttctttcct cacaacatca agaacggcat cgataagctc     720
ggctccttca gtgtaatggc ccttggccca gttgtttcca gcaccggatt gtccaaaaac     780
aaagttgtct ggcctgaaaa tctggccgta aggaccagtt cggaca                    826

<210> SEQ ID NO 61
<211> LENGTH: 629
<212> TYPE: DNA
<213> ORGANISM: Gossypium hirsutum
<220> FEATURE:
<221> NAME/KEY: unsure
<222> LOCATION: (1)..(629)
<223> OTHER INFORMATION: unsure at all n locations

<400> SEQUENCE: 61
aagagacagc tctagagtcg acctgcagaa gagtgngaaa aaatgttcag aatgggtgat      60
cgggttggtc gagcttcata tgacaagaaa aaactgttgc tctatgctat catatcgggg     120
tctcgtaggc aaaattgacyg tcttctcaga gatataccat cactttttcag taccatagag     180 gatttcctgt ggttcatatt ntcagcagta caggactttc ctggtggaac ctcatctaat     240
gagggnttag taccatacag tcttgacgat ttgcaagctt acctaaacaa atttgagccg     300
```

```
tcatattaca caaaaaatgg aaaggatcct ctagtatatc cgtacatctt gcttttaagt    360
atccagttgc taccagctat ttcatacctg tctaaagaag caggagagga agaataccat    420
attgatgctg ctcacatagc aattgtgcta gcagacaata gggtcctttc tgaagtttct    480
ggagccggac aaaagctggg agttatggat gcgtacgcag aagcttctag cattattagg    540
cagtatggct ctatgtatct acggcttggt aaccttcaaa tggctctaga atattacgca    600
caagctgctg ctgcaggtcg actctagag                                      629

<210> SEQ ID NO 62
<211> LENGTH: 287
<212> TYPE: DNA
<213> ORGANISM: Gossypium hirsutum
<220> FEATURE:
<221> NAME/KEY: unsure
<222> LOCATION: (1)..(287)
<223> OTHER INFORMATION: unsure at all n locations

<400> SEQUENCE: 62
atgagaaacg gtcccaccat ggactttcat attatcgcgc gcgcatatta cantggcttc     60
tcgcgatggg cgctaacttt ctcgcgatga gcgcgagcat attcaacttt aacaatatta    120
attgttttta tccattactg tcraaatgaa ctaaaatagt cgtcctagaa aaattgtaat    180
gactttacaa aaagaaaata atattaaaaa ctataaagtg ctaaaaaaaa cttcttttct    240
aattcaaatc gctaaataca gtcaaacctt attacctaac cacacta                  287

<210> SEQ ID NO 63
<211> LENGTH: 1086
<212> TYPE: DNA
<213> ORGANISM: Gossypium hirsutum
<220> FEATURE:
<221> NAME/KEY: unsure
<222> LOCATION: (1)..(1086)
<223> OTHER INFORMATION: unsure at all n locations

<400> SEQUENCE: 63
ctctagagtc gacctgcagt acatgcagag cgttatcttc ttgttttcgg tgggagttca     60
catgctactt tcttcaatga tttgcatgtc cttgatttgc aaactgtaag ataatttcac    120
ttttcagttt tctcatttgc ttgtctgagg aattaaattc tttatctttc ccttttttt    180 cttttcttat ttnttttttt gggtttgtag atggaatggt caaaacctgc acaactaggt    240
gagttaccaa ctcctagagc tggtcatgca ggagtgacta ttggggaaaa ctggtttatt    300
gctggaggtg gagacaacaa aagcggtaaa tgcttagttt tagtgttatt atactgtcag    360
catttgatat gacaataaga aaagcttgac ggattggttg tgtgaaaaag cttacttcta    420
tcactactta ttcttcgttg tttgtccttt tctcttcctc caggggcgtc aaaaactata    480
gtccttaaca tgtctagctt cgtttggtca gttgtgacat cagttgaagg aactgttcct    540
cttgctagta aggtatttta cattktacga atgcttattg tgttcaaaat tctgtgcatg    600
tggcaaatct cttttttgcat tgcttaatca tatgtatatt gttcaaatg tgtcgggact    660 gctgnaaaag tttaaacttc tgaatcttga tatacaaggg ttgttagact ttctgcatat    720
gttgtgcttc tctgtaatga ttatgatcat ttgacttgat tatcaataat aattttgaca    780
tgtttttttc tcatctattt tacttacgac tcaggtgtaa gtttcagata tcggtatgtt    840
caaattattc taagtttttt catgtattta tagtatcttt tacgggtcat attttcccat    900
acctatgttc taataagtgt tggacatggt tacttaaagg aaaaatgaag agtcagagca    960
acataggttc tcatcaatta acttcatcga cttctttagc ttgtaagctt aaaagcaaaa   1020
```

-continued

```
ttactgttgc atggaaatag ttcaaaattt ctggatattg cgcctctctg caggtcgact    1080
ctagag                                                               1086

<210> SEQ ID NO 64
<211> LENGTH: 367
<212> TYPE: DNA
<213> ORGANISM: Gossypium hirsutum
<220> FEATURE:
<221> NAME/KEY: unsure
<222> LOCATION: (1)..(367)
<223> OTHER INFORMATION: unsure at all n locations

<400> SEQUENCE: 64
acggaaaaat aagggtgtaa aagatagagc ctacaattcc aatatcaaac aaaaagctaa      60
aggcaaccaa anaagatgac gaaacttcaa gctaaaacat tgcacaattt tatggtayaa     120
gatactacaa tctaacttac ttcttcgcac tccttcatct tcttctgtgc tccatcaaat     180
tcatagttga cataaacaca tgccaaaaac tccgtgatgg gatctttgta agagcattga     240
tcttgctgga taaccttgat aaattctttg aattgaggtc ttctccttt gttgacaata      300 aaagcagtgg ctaagtacct tagaagatgg ggagcactgg tttgaatggc gtttagatac     360
ctggaaa                                                              367

<210> SEQ ID NO 65
<211> LENGTH: 958
<212> TYPE: DNA
<213> ORGANISM: Gossypium hirsutum
<220> FEATURE:
<221> NAME/KEY: unsure
<222> LOCATION: (1)..(958)
<223> OTHER INFORMATION: unsure at all n locations

<400> SEQUENCE: 65
taagtataaa gatattgaat gatcaacatg tgtgatatat tatgttaaaa aaacacacat      60
gtatgatata ccatatcact tgttccaat tcagaatcaa aaggaagatc aaatgggttg      120
gttggtttaa gatcagcagc ttgtgtctct ttctctccct gcaaaattaa gtttagaacc     180
taaattagat taaagaagag ctcaataaga atccatataa tataaagaac aaaagaacca     240
gtaagttaaa agaacaaacc ggaagtggat tcattgatgg agcatataat ggtgctatgc     300
cattctctga tggtagagta gcagcaggaa aaccaatatg ggagtcagca gtttggatac     360
cataattatc atggttctgc aagaatagat attttaaaca taaatacaag aaatgtgaac     420
tttttggcat aattagaaat aaaagtagca aacctctgaa actgctaagc ccaaatgttc     480
atcagtggtg gccatatgtt cgtatgctac tacttgaggt tcaagaggaa gtgattcaac     540
cgaatcatta aaagcattcc atgactgttc aaagacaaag ggtcacttga gcatgcaatt     600
gacaggagag aaaattttat atttcaaacc gtaaccatat gtagaccaag caataaagcc     660
gttgaataaa tgcatgctta aagcatctct ttccttattct tcacaaamct gcatgtgaaa    720
tggcttacct gagtgccagt tgcaacaggg ggggcttgan cctcatgtcc atcttgccat     780
ttagtagaca ttgctgaaga atccccaaaa gcactaaaat tttcaaaagg tgaccactgc     840
atggttgtgt ttatggatga ctgttggtca aacttcactg acaaatcttc atcactgggc     900
atcacagcag gtaaaagatt tttggatact ggatcagatg ctgcaggtcc tgtctctt      958

<210> SEQ ID NO 66
<211> LENGTH: 410
<212> TYPE: DNA
<213> ORGANISM: Gossypium hirsutum
```

-continued

<400> SEQUENCE: 66

```
ttcaacaagc tgtactttaa gctacacgtc taaatgtttg tgttttacca agctgttcat    60
ctaattcttg gcacctctag gtgcagttgc tggcacccct ttgttcccag atgcttctgc   120
atttgaatgg ataacttgag cacatgtact atcagggcac tcagcaactc gatcctgagg   180
tgagactgga ctgggggctt ttgatttctg ctgcttgttt cgtccaagaa ctctgcaaaa   240
ggagaatccg ttgataggtt ccagtatttg taacaacttt cataaacttc taatcccatg   300
gtctgagaga aattcaattc aaccatcaaa gatgacarca ttcgaggtaa agtgcaaat    360
accatcagat aatgtaacca atgatttgaa atggatacaa tctgtctctt              410
```

<210> SEQ ID NO 67
<211> LENGTH: 453
<212> TYPE: DNA
<213> ORGANISM: Gossypium hirsutum
<220> FEATURE:
<221> NAME/KEY: unsure
<222> LOCATION: (1)..(453)
<223> OTHER INFORMATION: unsure at all n locations

<400> SEQUENCE: 67

```
gatagacaat tacatttaaa atggaaataa gataaaacaa taatttaaaa caattcaaaa    60
ctagaataaa aataataact ttatttctaa gattacgtta ttatgacccc tagattgatg   120
gttggtagag cagtaatctt agattgacaa ttatgaaaaa agtgtgaaca gttgatggta   180
aaagaaaggt ggattttcca acttaggaag ttgaaatgat gaactcttgt agtgagttac   240
ggtagcatag aaactgaatg caaaatgtga tttgacatct attaggcaag gcccctcaac   300
cgactaccaa gataatcrgg cacgaacctc actgctttga actaatagat agaagccgat   360
gattggttgn taataaagaa aaccggttgg ttggctttgg tgaataagag ttggtgttgt   420
ttcagccaaa aaggtaaata gttagaacta tac                                453
```

<210> SEQ ID NO 68
<211> LENGTH: 551
<212> TYPE: DNA
<213> ORGANISM: Gossypium hirsutum

<400> SEQUENCE: 68

```
cattgaagcg gcagctacaa tgatggcggt ggagaacttc ttcatgtcca tggcgtataa    60
agggattatt aaacgcaccg gaaatgaaag agacctgcgt ttaawtactg gtgaatggga   120
agccgccggt gattattatt tgctttgtta ttgcaggtct gaagaacaat gatggtgggg   180
gaggtgattt ataggtgaaa attaatggct attttagtg atgacattca aaaggataat    240
tacgtgtttg gttttgcat ggtttgcggg atagacatgc attttaaaa acgatttga     300
cagggtttta cgtaagggat tttaaatttt aagattatat gataatgatt tttttattta   360
aatttaatta aattatgtat tttcactttt ttaaatca caaaactta attagagttg     420
gatatattaa ttttgataaa ttattttatg dacccttct attccattac ataatcccgt    480
ccaataaaaa agggacacat cattttaat ttgaaatttt aatccaaatg tacatataat   540
gcctgtctct t                                                        551
```

<210> SEQ ID NO 69
<211> LENGTH: 560
<212> TYPE: DNA
<213> ORGANISM: Gossypium hirsutum

<400> SEQUENCE: 69

```
ctggctgttg gcctccagcg ttggtggccg ccgtatatgg tggtcggagt aatacgaaaa    60
gaggtctttt tgaccgtttg gttctcccca accctgattt aaaacctaaa attctagaaa   120
aagcctttta aaagtaaaat aaaacaaaca aaccctttggt tccctctcc gatctcagaa   180 aggtaacttt ttttcttttga atatctatat atgcatgttc tttattcgaa aataaacttg   240
caaaggaaat aaaagaacag aacgaaagac caccttgatt ctttttttat ccgattgcta   300
ttttttttgt gtctccttct aaaaaaatta caatgaaaaa tgtttatggc tttgtagccg   360
agtgattaca gttttttttt gttctttttt gctgctattt cttgctgttg tgtggccttt   420
tcttgtaggt ataaggctgg atgcaagtgt ggcatgctag tacgcggacg tggaggccgt   480
tcggaggttg cgctgtaggc tgggggctgc gacgcgcctw aacaaaccct agggtttctt   540 atttttttaat tttcgggcca                                              560
```

<210> SEQ ID NO 70
<211> LENGTH: 174
<212> TYPE: DNA
<213> ORGANISM: Gossypium hirsutum
<220> FEATURE:
<221> NAME/KEY: unsure
<222> LOCATION: (1)..(174)
<223> OTHER INFORMATION: unsure at all n locations

<400> SEQUENCE: 70

```
agttaccccc tggcccatga aggtangcag tatttcttaa tatgacacag cattttctta    60
cactgttttg ttctggcctt angaaaaata aaaagatgag atatagggtt tatagcggtt   120
yagtacaata tatttgatta tttatgttat tcttttttccc gagtagcctt ggtg        174
```

<210> SEQ ID NO 71
<211> LENGTH: 174
<212> TYPE: DNA
<213> ORGANISM: Gossypium hirsutum
<220> FEATURE:
<221> NAME/KEY: unsure
<222> LOCATION: (1)..(174)
<223> OTHER INFORMATION: unsure at all n locations

<400> SEQUENCE: 71

```
agttaccccc tggcccatga aggtargcag tatttcttaa tatgacacag cattttctta    60
cactgttttg ttctggcctt angaaaaata aaaagatgag atatagggtt tatagcggtt   120
nagtacaata tatttgatta tttatgttat tcttttttccc gagtagcctt ggtg        174
```

<210> SEQ ID NO 72
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 72

```
aagagacagc ctctagagtc gacctgcaga acagcattgg cataacaact gcaaataaaa    60
aacaacaatc aatccataaa acattagctc ctattatttt atgtacttac aaacaagtca   120
tccatttaag gaaactccaa aacacgcatc cncggattac aagtagaact actgaatcgc   180
gaagtttagr taatgaacta gatatacttt ttaattaaca ttcaagaata agtatagcat   240
gcttaaacta taagtcaatc atcattattt ctttctttttt gttaatagga acatatatat   300
cctacacgtc atgttactcg gactcaggtg agtgtgttat atgagggatg tgtccaacat   360
```

```
gagtatcttt ttttacatgt aattgatggt cctncaaaac atgtatttga agtctccaaa      420
atcatgtcca natatgtgcc aagcatggat gctttcaaga aaaatgaana ccatactcca      480
agtaatatng caaatatggt agaaaatagg accataaagc aataacattg atacctgttc      540
cctatattta gaagtcccct cggtgataag tcnaaggctn cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                 814

<210> SEQ ID NO 73
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 73
aagagacagc ctctagagtc gacctgcaga acagcattgg cataacaact gcaaaataaa       60
aacaacaatc aatccataaa acattagctc ctattatttt atgtacttac aaacaagtca      120
tccatttaag gaaactccaa aacacgcatc cncggattac aagtagaact actgaatcgc      180
gaagtttagn taatgaacta gatatacttt ttaattaaca ttcaagaata agtatagcat      240
gcttaaacta taagtcaatc atcattattt ctttcttttt gttaatagga acatatatat      300
cctacacgtc atgttactcg gactcaggtg agtgtgttat atgagggatg tgtccaacat      360
gagtatcttt ttttacatgt aattgatggt cctwcaaaac atgtatttga agtctccaaa      420
atcatgtcca natatgtgcc aagcatggat gctttcaaga aaaatgaana ccatactcca      480
agtaatatng caaatatggt agaaaatagg accataaagc aataacattg atacctgttc      540
cctatattta gaagtcccct cggtgataag tcnaaggctn cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                 814

<210> SEQ ID NO 74
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 74
aagagacagc ctctagagtc gacctgcaga acagcattgg cataacaact gcaaaataaa       60
aacaacaatc aatccataaa acattagctc ctattatttt atgtacttac aaacaagtca      120
tccatttaag gaaactccaa aacacgcatc cncggattac aagtagaact actgaatcgc      180
gaagtttagn taatgaacta gatatacttt ttaattaaca ttcaagaata agtatagcat      240
gcttaaacta taagtcaatc atcattattt ctttcttttt gttaatagga acatatatat      300
cctacacgtc atgttactcg gactcaggtg agtgtgttat atgagggatg tgtccaacat      360
```

```
gagtatcttt ttttacatgt aattgatggt cctncaaaac atgtatttga agtctccaaa    420
atcatgtcca watatgtgcc aagcatggat gctttcaaga aaaatgaana ccatactcca    480
agtaatatng caaatatggt agaaaatagg accataaagc aataacattg atacctgttc    540
cctatattta gaagtccoct cggtgataag tcnaaggctn cacactggaa aaattttaca    600
aattcttcnt aaggaaacag catctgagac agcacaataa cggatcatag tcagagtttt    660
cctttcacaa ttcaagagcc aaatgaaact aaaagggatg caatagatat tgatcatata    720
taaacataaa gaaagtatga aactgacctt tattttcttc cgtctctcgc cacaaagcgc    780
agaaaaactg ctcctggcag gctttgttga cttc                               814
```

```
<210> SEQ ID NO 75
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 75
aagagacagc ctctagagtc gacctgcaga acagcattgg cataacaact gcaaaataaa     60
aacaacaatc aatccataaa acattagctc ctattatttt atgtacttac aaacaagtca    120
tccatttaag gaaactccaa aacacgcatc cncggattac aagtagaact actgaatcgc    180
gaagtttagn taatgaacta gatatacttt ttaattaaca ttcaagaata agtatagcat    240
gcttaaacta taagtcaatc atcattattt ctttcttttt gttaatagga acatatatat    300
cctacacgtc atgttactcg gactcaggtg agtgtgttat atgagggatg tgtccaacat    360
gagtatcttt ttttacatgt aattgatggt cctncaaaac atgtatttga agtctccaaa    420
atcatgtcca natatgtgcc aagcatggat gctttcaaga aaaatgaara ccatactcca    480
agtaatatng caaatatggt agaaaatagg accataaagc aataacattg atacctgttc    540
cctatattta gaagtcccct cggtgataag tcnaaggctn cacactggaa aaattttaca    600
aattcttcnt aaggaaacag catctgagac agcacaataa cggatcatag tcagagtttt    660
cctttcacaa ttcaagagcc aaatgaaact aaaagggatg caatagatat tgatcatata    720
taaacataaa gaaagtatga aactgacctt tattttcttc cgtctctcgc cacaaagcgc    780
agaaaaactg ctcctggcag gctttgttga cttc                               814
```

```
<210> SEQ ID NO 76
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 76
aagagacagc ctctagagtc gacctgcaga acagcattgg cataacaact gcaaaataaa     60
aacaacaatc aatccataaa acattagctc ctattatttt atgtacttac aaacaagtca    120
tccatttaag gaaactccaa aacacgcatc cncggattac aagtagaact actgaatcgc    180
gaagtttagn taatgaacta gatatacttt ttaattaaca ttcaagaata agtatagcat    240
gcttaaacta taagtcaatc atcattattt ctttcttttt gttaatagga acatatatat    300
cctacacgtc atgttactcg gactcaggtg agtgtgttat atgagggatg tgtccaacat    360
```

```
gagtatcttt ttttacatgt aattgatggt cctncaaaac atgtatttga agtctccaaa      420
atcatgtcca natatgtgcc aagcatggat gctttcaaga aaaatgaana ccatactcca      480
agtaatatyg caaatatggt agaaaatagg accataaagc aataacattg atacctgttc      540
cctatattta gaagtcccct cggtgataag tcnaaggctn cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                 814

<210> SEQ ID NO 77
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 77
aagagacagc ctctagagtc gacctgcaga acagcattgg cataacaact gcaaaataaa       60
aacaacaatc aatccataaa acattagctc ctattatttt atgtacttac aaacaagtca      120
tccatttaag gaaactccaa aacacgcatc cncggattac aagtagaact actgaatcgc      180
gaagtttagn taatgaacta gatatacttt ttaattaaca ttcaagaata agtatagcat      240
gcttaaacta taagtcaatc atcattattt ctttcttttt gttaatagga acatatatat      300
cctacacgtc atgttactcg gactcaggtg agtgtgttat atgagggatg tgtccaacat      360
gagtatcttt ttttacatgt aattgatggt cctncaaaac atgtatttga agtctccaaa      420
atcatgtcca natatgtgcc aagcatggat gctttcaaga aaaatgaana ccatactcca      480
agtaatatng caaatatggt agaaaatagg accataaagc aataacattg atacctgttc      540
cctatattta gaagtcccct cggtgataag tcraaggctn cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                 814

<210> SEQ ID NO 78
<211> LENGTH: 814
<212> TYPE: DNA
<213> ORGANISM: Gossypium hirsutum
<220> FEATURE:
<221> NAME/KEY: unsure
<222> LOCATION: (1)..(814)
<223> OTHER INFORMATION: unsure at all n locations

<400> SEQUENCE: 78
aagagacagc ctctagagtc gacctgcaga acagcattgg cataacaact gcaaaataaa       60
aacaacaatc aatccataaa acattagctc ctattatttt atgtacttac aaacaagtca      120
tccatttaag gaaactccaa aacacgcatc cncggattac aagtagaact actgaatcgc      180
gaagtttagn taatgaacta gatatacttt ttaattaaca ttcaagaata agtatagcat      240
gcttaaacta taagtcaatc atcattattt ctttcttttt gttaatagga acatatatat      300
cctacacgtc atgttactcg gactcaggtg agtgtgttat atgagggatg tgtccaacat      360
```

```
gagtatcttt ttttacatgt aattgatggt cctncaaaac atgtatttga agtctccaaa      420
atcatgtcca natatgtgcc aagcatggat gctttcaaga aaaatgaana ccatactcca      480
agtaatatng caaatatggt agaaaatagg accataaagc aataacattg atacctgttc      540
cctatattta gaagtcccct cggtgataag tcnaaggctk cacactggaa aaattttaca      600
aattcttcnt aaggaaacag catctgagac agcacaataa cggatcatag tcagagtttt      660
cctttcacaa ttcaagagcc aaatgaaact aaaagggatg caatagatat tgatcatata      720
taaacataaa gaaagtatga aactgacctt tattttcttc cgtctctcgc cacaaagcgc      780
agaaaaactg ctcctggcag gctttgttga cttc                                 814

<210> SEQ ID NO 79
<211> LENGTH: 366
<212> TYPE: DNA
<213> ORGANISM: Gossypium hirsutum
<220> FEATURE:
<221> NAME/KEY: unsure
<222> LOCATION: (1)..(366)
<223> OTHER INFORMATION: unsure at all n locations

<400> SEQUENCE: 79
gagtcgacct gcagatttcg ggcacagcgt tagttttgga tgaaatcatc aaccatgtgc       60
agtccctaca acgtcaagtg gaggttagaa ttgtgcatct tnagcatcac tttagttttt      120
ctcatgtact rttcggtttg aacttgttaa aagaaatcat gaattcttga tatgttctga      180
agcattgcaa gtggactaat aagtntagtg aaagccactt gattcccccc tattgctacc      240
caaaatcttt ggtaattttt ttatcatata gttttaaaa tttatagtct atttgttcca       300
aaatcacttt caaatgacta tagatgtgaa tttggcctga gattaatcgc cttaaatatt      360
tgccga                                                                366

<210> SEQ ID NO 80
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 80
gtgtacttta tatcagaaga tttcaaccag tagatctcca ataaacttaa atggttttga       60
atgttgaatg cngaagcaaa atataacata cagtgggctt tgagtngaca ttatccataa      120
caatttctcg tattttcct tgtccaattt caaattcgga ccgcagatct ctggtaggat       180
tagtggcatt atgcacagca gaaggagcct ctgtaatatt tgattgyaag tttaacttac      240
aacttgggtt gagaatatta acctggaanc aaaacataac agatnaaaat aganacaaag      300
cgatcaacaa agttggagaa acgaggctaa aatgtctcta cctcaca                   347

<210> SEQ ID NO 81
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 81
gtgtacttta tatcagaaga tttcaaccag tagatctcca ataaacttaa atggttttga       60
```

```
atgttgaatg cngaagcaaa atataacata cagtgggctt tgagtngaca ttatccataa    120
caatttctcg tattttcct tgtccaattt caaattcgga ccgcagatct ctggtaggat     180
tagtggcatt atgcacagca gaaggagcct ctgtaatatt tgattgnaag tttaacttac    240
aacttgggtt gagaatatta acctggaarc aaaacataac agatnaaaat aganacaaag    300
cgatcaacaa agttggagaa acgaggctaa aatgtctcta cctcaca                 347
```

<210> SEQ ID NO 82
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 82

```
gtgtacttta tatcagaaga tttcaaccag tagatctcca ataaacttaa atggttttga     60
atgttgaatg cngaagcaaa atataacata cagtgggctt tgagtngaca ttatccataa    120
caatttctcg tattttcct tgtccaattt caaattcgga ccgcagatct ctggtaggat     180
tagtggcatt atgcacagca gaaggagcct ctgtaatatt tgattgnaag tttaacttac    240
aacttgggtt gagaatatta acctggaanc aaaacataac agatmaaaat aganacaaag    300
cgatcaacaa agttggagaa acgaggctaa aatgtctcta cctcaca                 347
```

<210> SEQ ID NO 83
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 83

```
gtgtacttta tatcagaaga tttcaaccag tagatctcca ataaacttaa atggttttga     60
atgttgaatg cngaagcaaa atataacata cagtgggctt tgagtngaca ttatccataa    120
caatttctcg tattttcct tgtccaattt caaattcgga ccgcagatct ctggtaggat     180
tagtggcatt atgcacagca gaaggagcct ctgtaatatt tgattgnaag tttaacttac    240
aacttgggtt gagaatatta acctggaanc aaaacataac agatnaaaat agaracaaag    300
cgatcaacaa agttggagaa acgaggctaa aatgtctcta cctcaca                 347
```

<210> SEQ ID NO 84
<211> LENGTH: 347
<212> TYPE: DNA
<213> ORGANISM: Gossypium hirsutum
<220> FEATURE:
<221> NAME/KEY: unsure
<222> LOCATION: (1)..(347)
<223> OTHER INFORMATION: unsure at all n locations

<400> SEQUENCE: 84

```
gtgtacttta tatcagaaga tttcaaccag tagatctcca ataaacttaa atggttttga     60
atgttgaatg crgaagcaaa atataacata cagtgggctt tgagtngaca ttatccataa    120
caatttctcg tattttcct tgtccaattt caaattcgga ccgcagatct ctggtaggat     180
tagtggcatt atgcacagca gaaggagcct ctgtaatatt tgattgnaag tttaacttac    240
aacttgggtt gagaatatta acctggaanc aaaacataac agatnaaaat aganacaaag    300
```

-continued cgatcaacaa agttggagaa acgaggctaa aatgtctcta cctcaca        347

<210> SEQ ID NO 85
<211> LENGTH: 581
<212> TYPE: DNA
<213> ORGANISM: Gossypium hirsutum
<220> FEATURE:
<221> NAME/KEY: unsure
<222> LOCATION: (1)..(581)
<223> OTHER INFORMATION: unsure at all n locations

<400> SEQUENCE: 85
gtttgattca gttgaaggtt cgagagataa gataaccacc tggttcaaag aagtaaatca    60
caatttaggc aaaaatgtaa tacaaagtac ttacatcata acaaaaaagg atgaaatatt   120
atactttgct cgtacgaaag cctatctcat caaaaatgtc attttcaagc tgcaagatat   180
tgtctcccag aaaagaaacc ggcttctnaa ctttaaaact tgctactata tcatgatctg   240
gacaataaaa taaccaaatg ttaratcact tccataatta taaattcaat attggtccaa   300
ccccacagca aatatngaat tgccaatcct acggaccagc ttcgaccaga aaccgtata    360 taaataacta taacaattat tatatgaatg cagagattaa taaccaagtt gatacatcca   420
aaaaaattct caaacaata ccgatgacaa gtacttatat gcaatatacg tgatataaca    480
tccaatagta attgatctat gaatgttga acaattcggt cagaaaaccg tataaacaac    540
aacaatggtt atatgaatgc agagatcaat aaccaagtta a                      581

<210> SEQ ID NO 86
<211> LENGTH: 581
<212> TYPE: DNA
<213> ORGANISM: Gossypium hirsutum
<220> FEATURE:
<221> NAME/KEY: unsure
<222> LOCATION: (1)..(581)
<223> OTHER INFORMATION: unsure at all n locations

<400> SEQUENCE: 86
gtttgattca gttgaaggtt cgagagataa gataaccacc tggttcaaag aagtaaatca    60
caatttaggc aaaaatgtaa tacaaagtac ttacatcata acaaaaaagg atgaaatatt   120
atactttgct cgtacgaaag cctatctcat caaaaatgtc attttcaagc tgcaagatat   180
tgtctcccag aaaagaaacc ggcttctnaa ctttaaaact tgctactata tcatgatctg   240
gacaataaaa taaccaaatg ttanatcact tccataatta taaattcaat attggtccaa   300
ccccacagca aatatygaat tgccaatcct acggaccagc ttcgaccaga aaccgtata    360 taaataacta taacaattat tatatgaatg cagagattaa taaccaagtt gatacatcca   420
aaaaaattct caaacaata ccgatgacaa gtacttatat gcaatatacg tgatataaca    480
tccaatagta attgatctat gaatgttga acaattcggt cagaaaaccg tataaacaac    540
aacaatggtt atatgaatgc agagatcaat aaccaagtta a                      581

<210> SEQ ID NO 87
<211> LENGTH: 516
<212> TYPE: DNA
<213> ORGANISM: Gossypium hirsutum
<220> FEATURE:
<221> NAME/KEY: unsure
<222> LOCATION: (1)..(516)
<223> OTHER INFORMATION: unsure at all n locations

<400> SEQUENCE: 87
gatttagctt gtccagtctg ctgcaaaatg aaatgtcgga gcaatgtaga nncgaaaaca    60

```
tataaaaagg agaggaaaaa gaatgaaaaa acaacctgtt ggttactttg atctttgag    120 gaagtcactg tttgattctg ttgttgcaat tgcggcacnt atgtaacgga atgagaacct    180
ccaaragtgt tgccgttcat ctgaccacgg tttggcctgg tttgtcttgg agcagtaggg    240
aactatcaca tggtatagta agtactcata ttcgtacagt tcgaaccgct aacgtacttg    300
tatataaata cacataccag gggaagtgat gagtattgaa agactggtct ggttggtggt    360
gcaaagccat tagctctcca tcctggcctt aaacctaaag gttggtgcat catcccgggc    420
cttaggggta cttgtgaaac aaagccagtt ggagatgcgt agtaaagcgg agggtatcct    480
cccgggagaa caactgttga aggccctgct aatcct                              516
```

<210> SEQ ID NO 88
<211> LENGTH: 516
<212> TYPE: DNA
<213> ORGANISM: Gossypium hirsutum
<220> FEATURE:
<221> NAME/KEY: unsure
<222> LOCATION: (1)..(516)
<223> OTHER INFORMATION: unsure at all n locations

<400> SEQUENCE: 88

```
gatttagctt gtccagtctg ctgcaaaatg aaatgtcgga gcaatgtaga sncgaaaaca    60
tataaaaagg agaggaaaaa gaatgaaaaa acaacctgtt ggttactttg atctttgag    120 gaagtcactg tttgattctg ttgttgcaat tgcggcacnt atgtaacgga atgagaacct    180
ccaanagtgt tgccgttcat ctgaccacgg tttggcctgg tttgtcttgg agcagtaggg    240
aactatcaca tggtatagta agtactcata ttcgtacagt tcgaaccgct aacgtacttg    300
tatataaata cacataccag gggaagtgat gagtattgaa agactggtct ggttggtggt    360
gcaaagccat tagctctcca tcctggcctt aaacctaaag gttggtgcat catcccgggc    420
cttaggggta cttgtgaaac aaagccagtt ggagatgcgt agtaaagcgg agggtatcct    480
cccgggagaa caactgttga aggccctgct aatcct                              516
```

<210> SEQ ID NO 89
<211> LENGTH: 516
<212> TYPE: DNA
<213> ORGANISM: Gossypium hirsutum
<220> FEATURE:
<221> NAME/KEY: unsure
<222> LOCATION: (1)..(516)
<223> OTHER INFORMATION: unsure at all n locations

<400> SEQUENCE: 89

```
gatttagctt gtccagtctg ctgcaaaatg aaatgtcgga gcaatgtaga gscgaaaaca    60
tataaaaagg agaggaaaaa gaatgaaaaa acaacctgtt ggttactttg atctttgag    120 gaagtcactg tttgattctg ttgttgcaat tgcggcacnt atgtaacgga atgagaacct    180
ccaanagtgt tgccgttcat ctgaccacgg tttggcctgg tttgtcttgg agcagtaggg    240
aactatcaca tggtatagta agtactcata ttcgtacagt tcgaaccgct aacgtacttg    300
tatataaata cacataccag gggaagtgat gagtattgaa agactggtct ggttggtggt    360
gcaaagccat tagctctcca tcctggcctt aaacctaaag gttggtgcat catcccgggc    420
cttaggggta cttgtgaaac aaagccagtt ggagatgcgt agtaaagcgg agggtatcct    480
cccgggagaa caactgttga aggccctgct aatcct                              516
```

<210> SEQ ID NO 90
<211> LENGTH: 614
<212> TYPE: DNA

```
<213> ORGANISM: Gossypium hirsutum
<220> FEATURE:
<221> NAME/KEY: unsure
<222> LOCATION: (1)..(614)
<223> OTHER INFORMATION: unsure at all n locations

<400> SEQUENCE: 90
cayanaccaa ttacctattt agctcccaca tccagtccgc tgccaaatgt agcttttgct      60
catgccaagc ctccatcaaa gagtgaacca aataaagagg atcctgatag gataccttca     120
gtttcaccat cagcatcggc acctttctgt gagtaaatga cgttttctga ataattaaac    180
atatcattgc acgccaaacc gaattttatg atcataaatt acctggacta ttcgtttcat    240
acaaatggtg tctaaagatg attttcttgt gcagtgattt tagtcatatt ttgaaattta    300
agatcgttat agcgattggt cggtctaatt catatattta tccatgctga gctcttcggt    360
aaaattacca tggaagccct tatactagaa gccgattgca ttttgtccct tctactaaaa    420
aaatagcaaa ttagttctta taggttagat taaagagcaa attggttctt ctattaaaaa    480
ttccagccat ttttactgtt aaaaattggt ctttgtatat tagcatgagg tacatgttaa    540
tagaaagact agttttctct ttaatctaac tttacatggt aaagagggta aaatgcaatt    600
tgactcctag taca                                                      614

<210> SEQ ID NO 91
<211> LENGTH: 614
<212> TYPE: DNA
<213> ORGANISM: Gossypium hirsutum
<220> FEATURE:
<221> NAME/KEY: unsure
<222> LOCATION: (1)..(614)
<223> OTHER INFORMATION: unsure at all n locations

<400> SEQUENCE: 91
canaraccaa ttacctattt agctcccaca tccagtccgc tgccaaatgt agcttttgct     60
catgccaagc ctccatcaaa gagtgaacca aataaagagg atcctgatag gataccttca    120
gtttcaccat cagcatcggc acctttctgt gagtaaatga cgttttctga ataattaaac   180
atatcattgc acgccaaacc gaattttatg atcataaatt acctggacta ttcgtttcat   240
acaaatggtg tctaaagatg attttcttgt gcagtgattt tagtcatatt ttgaaattta   300
agatcgttat agcgattggt cggtctaatt catatattta tccatgctga gctcttcggt   360
aaaattacca tggaagccct tatactagaa gccgattgca ttttgtccct tctactaaaa   420
aaatagcaaa ttagttctta taggttagat taaagagcaa attggttctt ctattaaaaa   480
ttccagccat ttttactgtt aaaaattggt ctttgtatat tagcatgagg tacatgttaa   540
tagaaagact agttttctct ttaatctaac tttacatggt aaagagggta aaatgcaatt   600
tgactcctag taca                                                     614

<210> SEQ ID NO 92
<211> LENGTH: 839
<212> TYPE: DNA
<213> ORGANISM: Gossypium hirsutum
<220> FEATURE:
<221> NAME/KEY: unsure
<222> LOCATION: (1)..(839)
<223> OTHER INFORMATION: unsure at all n locations

<400> SEQUENCE: 92
aagagacaga ttgtatggat gtttattaga ggtatacata tatcggatca aaacgggtcg     60
atgttcaatt ttaaaatatt ttttatgttt aagcttgttt tgaagtcgga tcgatccacc   120
```

-continued

```
caaaagctca ttttactatt aaaaaaataa atataaatga aatgcaccaa tagtaaagta      180
gtttgtatct aatgaaactt taatttgaga tttcaatctt accatttaac taaaaagact      240
atttattcca ctgaaattgg gtttccagaa atattaactt aatttccttt taaccagcat      300 gccattttc attaaccaaa catacccctaa ataatatcac agaatcagaa taaaaccata      360
ggcaaacatt tcaaacctat attttcaatt aaaaaataac ataatatttt gaatacaaat      420
taggataaaa cttgcgcaaa aaacaaatgg aacaaccgca ccagcgatgt gtaaatgtat      480
aataataagc tgtgagactg taatctattg ggacatgtat tcatgccaaa aaaccctaat      540
tagatataaa tattattccc atcatagaaa gaatagggtt aagttgaaaa aaatgattaa      600
tgagaaaaaa aaataaagaa tctagccatc attagttggg cctttcaatt gaattttcag      660
gcattgtcat cgatggcggt atnttctgga gggttaccgg caagccaacc ccaaacaccg      720
ctcgaaccct gcctctgcwt tgcatttaag gcagcttgtt cagatgcagc tttcagtcgt      780
tgcaggaatt caagttcttt ttctagtgtt tccattgtct gaagcttttt gtcgcagtt      839
```

<210> SEQ ID NO 93
<211> LENGTH: 481
<212> TYPE: DNA
<213> ORGANISM: Gossypium hirsutum
<220> FEATURE:
<221> NAME/KEY: unsure
<222> LOCATION: (1)..(481)
<223> OTHER INFORMATION: unsure at all n locations

<400> SEQUENCE: 93

```
gggaatatgc gtgttttata tatcaaaatc ggacaatttg ttctgccagg aaagaacttt       60
tcattttatc aaagtaattt gaataagtct atcaaatttc aaataagaca ttaagatgaa      120
agaatgaaaa tgttaacctt aagatataaa cnctttgctg gaatggaatg aataaataca      180
tcagtyagag cctgaagaat ctccggagca catgatgata atgccttgat attttttggtt     240 gcagttttct ttgaataagt gnctggaatn ctgagctcta atttagagtc tcccattaca      300
gtattgtttg attcatcagc atcctctcca gatctaagta tattttttgtt ttggttgaca     360 agaatctaca gaaaaaataa caccactata gatattatac aagagaaaag aaaacaacna      420
acaaaagtta tttggaaaga ggatcaacgt aaggttctag gacttacaaa actaatggta      480
a                                                                      481
```

<210> SEQ ID NO 94
<211> LENGTH: 481
<212> TYPE: DNA
<213> ORGANISM: Gossypium hirsutum
<220> FEATURE:
<221> NAME/KEY: unsure
<222> LOCATION: (1)..(481)
<223> OTHER INFORMATION: unsure at all n locations

<400> SEQUENCE: 94

```
gggaatatgc gtgttttata tatcaaaatc ggacaatttg ttctgccagg aaagaacttt       60
tcattttatc aaagtaattt gaataagtct atcaaatttc aaataagaca ttaagatgaa      120
agaatgaaaa tgttaacctt aagatataaa cnctttgctg gaatggaatg aataaataca      180
tcagtnagag cctgaagaat ctccggagca catgatgata atgccttgat attttttggtt     240 gcagttttct ttgaataagt gkctggaatn ctgagctcta atttagagtc tcccattaca      300
gtattgtttg attcatcagc atcctctcca gatctaagta tattttttgtt ttggttgaca     360 agaatctaca gaaaaaataa caccactata gatattatac aagagaaaag aaaacaacna      420
```

| | |
|---|---|
| acaaaagtta tttggaaaga ggatcaacgt aaggttctag gacttacaaa actaatggta | 480 |
| a | 481 |

<210> SEQ ID NO 95
<211> LENGTH: 481
<212> TYPE: DNA
<213> ORGANISM: Gossypium hirsutum
<220> FEATURE:
<221> NAME/KEY: unsure
<222> LOCATION: (1)..(481)
<223> OTHER INFORMATION: unsure at all n locations

<400> SEQUENCE: 95

| | |
|---|---|
| gggaatatgc gtgttttata tatcaaaatc ggacaatttg ttctgccagg aaagaacttt | 60 |
| tcattttatc aaagtaattt gaataagtct atcaaatttc aaataagaca ttaagatgaa | 120 |
| agaatgaaaa tgttaacctt aagatataaa cnctttgctg gaatggaatg aataaataca | 180 |
| tcagtnagag cctgaagaat ctccggagca catgatgata atgccttgat attttttggtt | 240 |
| gcagttttct ttgaataagt gnctggaatw ctgagctcta atttagagtc tcccattaca | 300 |
| gtattgtttg attcatcagc atcctctcca gatctaagta tattttttgtt ttggttgaca | 360 |
| agaatctaca gaaaaaataa caccactata gatattatac aagagaaaag aaaacaacna | 420 |
| acaaaagtta tttggaaaga ggatcaacgt aaggttctag gacttacaaa actaatggta | 480 |
| a | 481 |

<210> SEQ ID NO 96
<211> LENGTH: 481
<212> TYPE: DNA
<213> ORGANISM: Gossypium hirsutum
<220> FEATURE:
<221> NAME/KEY: unsure
<222> LOCATION: (1)..(481)
<223> OTHER INFORMATION: unsure at all n locations

<400> SEQUENCE: 96

| | |
|---|---|
| gggaatatgc gtgttttata tatcaaaatc ggacaatttg ttctgccagg aaagaacttt | 60 |
| tcattttatc aaagtaattt gaataagtct atcaaatttc aaataagaca ttaagatgaa | 120 |
| agaatgaaaa tgttaacctt aagatataaa cnctttgctg gaatggaatg aataaataca | 180 |
| tcagtnagag cctgaagaat ctccggagca catgatgata atgccttgat attttttggtt | 240 |
| gcagttttct ttgaataagt gnctggaatn ctgagctcta atttagagtc tcccattaca | 300 |
| gtattgtttg attcatcagc atcctctcca gatctaagta tattttttgtt ttggttgaca | 360 |
| agaatctaca gaaaaaataa caccactata gatattatac aagagaaaag aaaacaacma | 420 |
| acaaaagtta tttggaaaga ggatcaacgt aaggttctag gacttacaaa actaatggta | 480 |
| a | 481 |

<210> SEQ ID NO 97
<211> LENGTH: 756
<212> TYPE: DNA
<213> ORGANISM: Gossypium hirsutum
<220> FEATURE:
<221> NAME/KEY: unsure
<222> LOCATION: (1)..(756)
<223> OTHER INFORMATION: unsure at all n locations

<400> SEQUENCE: 97

| | |
|---|---|
| ctctagagtc gacctgcagc tctttaagta atctgttatt tcaactaaca gacagtaatt | 60 |
| tgcagcagca attatgatta tgcaattgtt ttcagccaaa gaaaaaaagg aaaagcattt | 120 |

-continued

```
taaaaatcaa tataaatgat ctcaagaaat aacattcata tgtcacgaag ctagaacatt      180
cacggcccct gacgcatgtt ctagccccgt gacgcataca tgttnaagct taaaacaaag      240
tagtaagatg atgcgataca tgaatggcca attctatata aacacwagga agaagggaca      300
aaatttacta ttttatttag ggtgatggat caaatttatt ttccatcttt gcaagtgtgc      360
aaattgtgct tctaatttta ttgaaaatgt caaatttaca attggggtat tctacagaat      420
ttttcttgcc attatcatta acctttttta accaaattca ggaacttggg aataataata      480
ttcgaaagag gacacaataa gaaggatatc atcttggatg aataaatgca aaagaagtt       540 aatgaaatca agatagcat  gcctgtaact ccactaaatc tattgcagag cttttcaaca      600
agtgattcca tttgtttgtc ctgcaaaata tagtagatat caatatatca tgttaacgag      660
attataaaga acagtagttt cagttttata tcaacaatgt aaaccttctt gatggaaccg      720
attaagaact gcatgatgtt gcagaaagac actttc                                756
```

```
<210> SEQ ID NO 98
<211> LENGTH: 459
<212> TYPE: DNA
<213> ORGANISM: Gossypium hirsutum
<220> FEATURE:
<221> NAME/KEY: unsure
<222> LOCATION: (1)..(459)
<223> OTHER INFORMATION: unsure at all n locations

<400> SEQUENCE: 98
```

```
cattaacatt aagttgacct tgttcatgtt aacagcaata tatacgcatt gtcatataga       60
aattcatggt grttttnttt ttaatggatg aattgtagaa gatgattcct catttatcct      120
ttaccaacta attgcgttac ttttgcaggt tttactggca tagatgatcc ttacgaacca      180
cctttgaact gtgaggtatg tgtttanttg aatacgaaa  ttattagcgg cggcattgtg      240
aattaaaatt aggctattat tctgatataa atactgctag tttatgggta atcgttttcc      300
tcctttatag atagaactaa atcagaaaga tggagtttgt cccacaccta gtgccatggc      360
tggggaagta attacttact tggaggacaa aggatatctg caaggttagc gaccaattct      420
cggttgtcat ggtcgagcat tctcagtcga gttcaattg                             459
```

```
<210> SEQ ID NO 99
<211> LENGTH: 459
<212> TYPE: DNA
<213> ORGANISM: Gossypium hirsutum
<220> FEATURE:
<221> NAME/KEY: unsure
<222> LOCATION: (1)..(459)
<223> OTHER INFORMATION: unsure at all n locations

<400> SEQUENCE: 99
```

```
cattaacatt aagttgacct tgttcatgtt aacagcaata tatacgcatt gtcatataga       60
aattcatggt gntttyttt  ttaatggatg aattgtagaa gatgattcct catttatcct      120
ttaccaacta attgcgttac ttttgcaggt tttactggca tagatgatcc ttacgaacca      180
cctttgaact gtgaggtatg tgtttanttg aatacgaaa  ttattagcgg cggcattgtg      240
aattaaaatt aggctattat tctgatataa atactgctag tttatgggta atcgttttcc      300
tcctttatag atagaactaa atcagaaaga tggagtttgt cccacaccta gtgccatggc      360
tggggaagta attacttact tggaggacaa aggatatctg caaggttagc gaccaattct      420
cggttgtcat ggtcgagcat tctcagtcga gttcaattg                             459
```

```
<210> SEQ ID NO 100
```

-continued

```
<211> LENGTH: 629
<212> TYPE: DNA
<213> ORGANISM: Gossypium hirsutum
<220> FEATURE:
<221> NAME/KEY: unsure
<222> LOCATION: (1)..(629)
<223> OTHER INFORMATION: unsure at all n locations

<400> SEQUENCE: 100
aagagacagc tctagagtcg acctgcagaa gagtgngaaa aaatgttcag aatgggtgat      60
cgggttggtc gagcttcata tgacaagaaa aaactgttgc tctatgctat catatcgggg    120
tctcgtaggc aaattgacng tcttctcaga gatataccat cacttttcag taccatagag    180
gatttcctgt ggttcatatt rtcagcagta caggactttc ctggtggaac ctcatctaat    240
gagggnttag taccatacag tcttgacgat ttgcaagctt acctaaacaa atttgagccg    300
tcatattaca caaaaaatgg aaaggatcct ctagtatatc cgtacatctt gcttttaagt    360
atccagttgc taccagctat ttcatacctg tctaaagaag caggagagga agaataccat    420
attgatgctg ctcacatagc aattgtgcta gcagacaata gggtccttc tgaagtttct     480 ggagccggac aaaagctggg agttatggat gcgtacgcag aagcttctag cattattagg    540
cagtatggct ctatgtatct acggcttggt aaccttcaaa tggctctaga atattacgca    600
caagctgctg ctgcaggtcg actctagag                                      629

<210> SEQ ID NO 101
<211> LENGTH: 629
<212> TYPE: DNA
<213> ORGANISM: Gossypium hirsutum
<220> FEATURE:
<221> NAME/KEY: unsure
<222> LOCATION: (1)..(629)
<223> OTHER INFORMATION: unsure at all n locations

<400> SEQUENCE: 101
aagagacagc tctagagtcg acctgcagaa gagtgngaaa aaatgttcag aatgggtgat      60
cgggttggtc gagcttcata tgacaagaaa aaactgttgc tctatgctat catatcgggg    120
tctcgtaggc aaattgacng tcttctcaga gatataccat cacttttcag taccatagag    180
gatttcctgt ggttcatatt ntcagcagta caggactttc ctggtggaac ctcatctaat    240
gagggyttag taccatacag tcttgacgat ttgcaagctt acctaaacaa atttgagccg    300
tcatattaca caaaaaatgg aaaggatcct ctagtatatc cgtacatctt gcttttaagt    360
atccagttgc taccagctat ttcatacctg tctaaagaag caggagagga agaataccat    420
attgatgctg ctcacatagc aattgtgcta gcagacaata gggtccttc tgaagtttct     480 ggagccggac aaaagctggg agttatggat gcgtacgcag aagcttctag cattattagg    540
cagtatggct ctatgtatct acggcttggt aaccttcaaa tggctctaga atattacgca    600
caagctgctg ctgcaggtcg actctagag                                      629

<210> SEQ ID NO 102
<211> LENGTH: 629
<212> TYPE: DNA
<213> ORGANISM: Gossypium hirsutum
<220> FEATURE:
<221> NAME/KEY: unsure
<222> LOCATION: (1)..(629)
<223> OTHER INFORMATION: unsure at all n locations

<400> SEQUENCE: 102
aagagacagc tctagagtcg acctgcagaa gagtgygaaa aaatgttcag aatgggtgat      60
```

-continued

| | |
|---|---|
| cgggttggtc gagcttcata tgacaagaaa aaactgttgc tctatgctat catatcgggg | 120 |
| tctcgtaggc aaattgacng tcttctcaga gatataccat cacttttcag taccatagag | 180 |
| gatttcctgt ggttcatatt ntcagcagta caggactttc tggtggaac ctcatctaat | 240 |
| gagggnttag taccatacag tcttgacgat ttgcaagctt acctaaacaa atttgagccg | 300 |
| tcatattaca caaaaaatgg aaaggatcct ctagtatatc cgtacatctt gcttttaagt | 360 |
| atccagttgc taccagctat ttcatacctg tctaaagaag caggagagga agaataccat | 420 |
| attgatgctg ctcacatagc aattgtgcta gcagacaata gggtcctttc tgaagtttct | 480 |
| ggagccggac aaaagctggg agttatggat gcgtacgcag aagcttctag cattattagg | 540 |
| cagtatggct ctatgtatct acggcttggt aaccttcaaa tggctctaga atattacgca | 600 |
| caagctgctg ctgcaggtcg actctagag | 629 |

<210> SEQ ID NO 103
<211> LENGTH: 287
<212> TYPE: DNA
<213> ORGANISM: Gossypium hirsutum
<220> FEATURE:
<221> NAME/KEY: unsure
<222> LOCATION: (1)..(287)
<223> OTHER INFORMATION: unsure at all n locations

<400> SEQUENCE: 103

| | |
|---|---|
| atgagaaacg gtcccaccat ggactttcat attatcgcgc gcgcatatta cartggcttc | 60 |
| tcgcgatggg cgctaacttt ctcgcgatga gcgcgagcat attcaacttt aacaatatta | 120 |
| attgttttta tccattactg tcnaaatgaa ctaaatagt cgtcctagaa aaattgtaat | 180 |
| gactttacaa aaagaaaata atattaaaaa ctataaagtg ctaaaaaaaa cttcttttct | 240 |
| aattcaaatc gctaaataca gtcaaacctt attacctaac cacacta | 287 |

<210> SEQ ID NO 104
<211> LENGTH: 1086
<212> TYPE: DNA
<213> ORGANISM: Gossypium hirsutum
<220> FEATURE:
<221> NAME/KEY: unsure
<222> LOCATION: (1)..(1086)
<223> OTHER INFORMATION: unsure at all n locations

<400> SEQUENCE: 104

| | |
|---|---|
| ctctagagtc gacctgcagt acatgcagag cgttatcttc ttgttttcgg tgggagttca | 60 |
| catgctactt tcttcaatga tttgcatgtc cttgatttgc aaactgtaag ataatttcac | 120 |
| ttttcagttt tctcatttgc ttgtctgagg aattaatttc tttatctttc ccttttttt | 180 |
| cttttcttat ttwtttattt gggtttgtag atggaatggt caaaacctgc acaactaggt | 240 |
| gagttaccaa ctcctagagc tggtcatgca ggagtgacta ttggggaaaa ctggtttatt | 300 |
| gctggaggtg gagacaacaa aagcggtaaa tgcttagttt tagtgttatt atactgtcag | 360 |
| catttgatat gacaataaga aaagcttgac ggattggttg tgtgaaaaag cttacttcta | 420 |
| tcactactta ttcttcgttg tttgtccttt tctcttcctc caggggcgtc aaaaactata | 480 |
| gtccttaaca tgtctagctt cgtttggtca gttgtgacat cagttgaagg aactgttcct | 540 |
| cttgctagtg aggtatttta cattntacga atgcttattg tgttcaaaat tctgtgcatg | 600 |
| tggcaaatct cttttttgcat tgcttaatca tatgtatatt gtttcaaatg tgtcgggact | 660 |
| gctgnaaaag tttaaacttc tgaatcttga tatacaaggg ttgttagact ttctgcatat | 720 |
| gttgtgcttc tctgtaatga ttatgatcat ttgacttgat tatcaataat aattttgaca | 780 |

| | |
|---|---:|
| tgttttttc tcatctattt tacttacgac tcaggtgtaa gtttcagata tcggtatgtt | 840 |
| caaattattc taagttttt catgtattta tagtatcttt tacgggtcat attttcccat | 900 |
| acctatgttc taataagtgt tggacatggt tacttaaagg aaaaatgaag agtcagagca | 960 |
| acataggttc tcatcaatta acttcatcga cttctttagc ttgtaagctt aaaagcaaaa | 1020 |
| ttactgttgc atggaaatag ttcaaaattt ctggatattg cgcctctctg caggtcgact | 1080 |
| ctagag | 1086 |

<210> SEQ ID NO 105
<211> LENGTH: 1086
<212> TYPE: DNA
<213> ORGANISM: Gossypium hirsutum
<220> FEATURE:
<221> NAME/KEY: unsure
<222> LOCATION: (1)..(1086)
<223> OTHER INFORMATION: unsure at all n locations

<400> SEQUENCE: 105

| | |
|---|---:|
| ctctagagtc gacctgcagt acatgcagag cgttatcttc ttgttttcgg tgggagttca | 60 |
| catgctactt tcttcaatga tttgcatgtc cttgatttgc aaactgtaag ataatttcac | 120 |
| ttttcagttt tctcatttgc ttgtctgagg aattaatttc tttatctttc cctttttttt | 180 |
| cttttcttat ttntttattt gggtttgtag atggaatggt caaaacctgc acaactaggt | 240 |
| gagttaccaa ctcctagagc tggtcatgca ggagtgacta ttggggaaaa ctggtttatt | 300 |
| gctggaggtg gagacaacaa aagcggtaaa tgcttagttt tagtgttatt atactgtcag | 360 |
| catttgatat gacaataaga aaagcttgac ggattggttg tgtgaaaaag cttacttcta | 420 |
| tcactactta ttcttcgttg tttgtccttt tctcttcctc caggggcgtc aaaaactata | 480 |
| gtccttaaca tgtctagctt cgtttggtca gttgtgacat cagttgaagg aactgttcct | 540 |
| cttgctagtg aggtatttta cattntacga atgcttattg tgttcaaaat tctgtgcatg | 600 |
| tggcaaatct cttttgcat tgcttaatca tatgtatatt gtttcaaatg tgtcgggact | 660 |
| gctgyaaaag tttaaacttc tgaatcttga tatacaaggg ttgttagact ttctgcatat | 720 |
| gttgtgcttc tctgtaatga ttatgatcat ttgacttgat tatcaataat aattttgaca | 780 |
| tgttttttc tcatctattt tacttacgac tcaggtgtaa gtttcagata tcggtatgtt | 840 |
| caaattattc taagttttt catgtattta tagtatcttt tacgggtcat attttcccat | 900 |
| acctatgttc taataagtgt tggacatggt tacttaaagg aaaaatgaag agtcagagca | 960 |
| acataggttc tcatcaatta acttcatcga cttctttagc ttgtaagctt aaaagcaaaa | 1020 |
| ttactgttgc atggaaatag ttcaaaattt ctggatattg cgcctctctg caggtcgact | 1080 |
| ctagag | 1086 |

<210> SEQ ID NO 106
<211> LENGTH: 367
<212> TYPE: DNA
<213> ORGANISM: Gossypium hirsutum
<220> FEATURE:
<221> NAME/KEY: unsure
<222> LOCATION: (1)..(367)
<223> OTHER INFORMATION: unsure at all n locations

<400> SEQUENCE: 106

| | |
|---|---:|
| acggaaaaat aagggtgtaa aagatagagc ctacaattcc aatatcaaac aaaaagctaa | 60 |
| aggcaaccaa araagatgac gaaacttcaa gctaaaacat tgcacaattt tatggtanaa | 120 |
| gatactacaa tctaacttac ttcttcgcac tccttcatct tcttctgtgc tccatcaaat | 180 |

```
tcatagttga cataaacaca tgccaaaaac tccgtgatgg gatctttgta agagcattga    240
tcttgctgga taaccttgat aaattctttg aattgaggtc ttctcctttt gttgacaata    300
aaagcagtgg ctaagtacct tagaagatgg ggagcactgg tttgaatggc gtttagatac    360
ctggaaa                                                              367

<210> SEQ ID NO 107
<211> LENGTH: 958
<212> TYPE: DNA
<213> ORGANISM: Gossypium hirsutum
<220> FEATURE:
<221> NAME/KEY: unsure
<222> LOCATION: (1)..(958)
<223> OTHER INFORMATION: unsure at all n locations

<400> SEQUENCE: 107
taagtataaa gatattgaat gatcaacatg tgtgatatat tatgttaaaa aaacacacat     60
gtatgatata ccatatcact tgttccaat tcagaatcaa aaggaagatc aaatgggttg    120
gttggtttaa gatcagcagc ttgtgtctct ttctctccct gcaaaattaa gtttagaacc    180
taaattagat taaagaagag ctcaataaga atccatataa tataaagaac aaaagaacca    240
gtaagttaaa agaacaaacc ggaagtggat tcattgatgg agcatataat ggtgctatgc    300
cattctctga tggtagagta gcagcaggaa aaccaatatg ggagtcagca gtttggatac    360
cataattatc atggttctgc aagaatagat attttaaaca taaatacaag aaatgtgaac    420
tttttggcat aattagaaat aaaagtagca aacctctgaa actgctaagc ccaaatgttc    480
atcagtggtg gccatatgtt cgtatgctac tacttgaggt tcaagaggaa gtgattcaac    540
cgaatcatta aaagcattcc atgactgttc aaagacaaag ggtcacttga gcatgcaatt    600
gacaggagag aaaattttat atttcaaacc gtaaccatat gtagaccaag caataaagcc    660
gttgaataaa tgcatgctta aagcatctct ttcttattct tcacaaanct gcatgtgaaa    720
tggcttacct gagtgccagt tgcaacaggg ggggcttgam cctcatgtcc atcttgccat    780
ttagtagaca ttgctgaaga atccccaaaa gcactaaaat tttcaaaagg tgaccactgc    840
atggttgtgt ttatggatga ctgttggtca aacttcactg acaaatcttc atcactgggc    900
atcacagcag gtaaaagatt tttggatact ggatcagatg ctgcaggtcc tgtctctt     958

<210> SEQ ID NO 108
<211> LENGTH: 366
<212> TYPE: DNA
<213> ORGANISM: Gossypium hirsutum
<220> FEATURE:
<221> NAME/KEY: unsure
<222> LOCATION: (1)..(366)
<223> OTHER INFORMATION: unsure at all n locations

<400> SEQUENCE: 108
gagtcgacct gcagatttcg ggcacagcgt tagttttgga tgaaatcatc aaccatgtgc     60
agtccctaca acgtcaagtg gaggttagaa ttgtgcatct tnagcatcac tttagttttt    120
ctcatgtact nttcggtttg aacttgttaa aagaaatcat gaattcttga tatgttctga    180
agcattgcaa gtggactaat aagtstagtg aaagccactt gattcccccc tattgctacc    240
caaaatcttt ggtaattttt ttatcatata gttttaaaa tttatagtct atttgttcca    300
aaatcacttt caaatgacta tagatgtgaa tttggcctga gattaatcgc cttaaatatt    360
tgccga                                                               366

<210> SEQ ID NO 109
```

```
<211> LENGTH: 453
<212> TYPE: DNA
<213> ORGANISM: Gossypium hirsutum
<220> FEATURE:
<221> NAME/KEY: unsure
<222> LOCATION: (1)..(453)
<223> OTHER INFORMATION: unsure at all n locations

<400> SEQUENCE: 109
gatagacaat tacatttaaa atggaaataa gataaaacaa taatttaaaa caattcaaaa        60
ctagaataaa aataataact ttatttctaa gattacgtta ttatgacccc tagattgatg       120
gttggtagag cagtaatctt agattgacaa ttatgaaaaa agtgtgaaca gttgatggta       180
aaagaaaggt ggattttcca acttaggaag ttgaaatgat gaactcttgt agtgagttac       240
ggtagcatag aaactgaatg caaaatgtga tttgacatct attaggcaag gcccctcaac       300
cgactaccaa gataatcngg cacgaacctc actgctttga actaatagat agaagccgat       360
gattggttgr taataaagaa aaccggttgg ttggctttgg tgaataagag ttggtgttgt       420
ttcagccaaa aaggtaaata gttagaacta tac                                    453

<210> SEQ ID NO 110
<211> LENGTH: 443
<212> TYPE: DNA
<213> ORGANISM: Gossypium hirsutum
<220> FEATURE:
<221> NAME/KEY: unsure
<222> LOCATION: (1)..(443)
<223> OTHER INFORMATION: unsure at all n locations

<400> SEQUENCE: 110
cactatacac gcgcacacat atatataggg ttcgaattcg gtacacctag caatacaatc        60
ttttaactcc acaaaggagt taaaaaaact gccacatgtc ctattttat tattattta         120 ctacacctta agggtatgta ttacctattc aaccttgctn atggagacta aacaagccac       180
tagcagaatt ttccatggat acacacacag gccagtccaa taaagagtaa catactgtgg       240
caatatatga craatncacg agcgcgcata tatatcataa tgacatattt gtcatactat       300
ggaagattct ttttcttttt taaatnacaa attagattat actgggcaac ttaaaccgtc       360
attcaggctc accaattaac aaccaataaa atgctaaaac caacactata tgtatatctg       420
agaaaatgca tacacatata aat                                               443

<210> SEQ ID NO 111
<211> LENGTH: 443
<212> TYPE: DNA
<213> ORGANISM: Gossypium hirsutum
<220> FEATURE:
<221> NAME/KEY: unsure
<222> LOCATION: (1)..(443)
<223> OTHER INFORMATION: unsure at all n locations

<400> SEQUENCE: 111
cactatacac gcgcacacat atatataggg ttcgaattcg gtacacctag caatacaatc        60
ttttaactcc acaaaggagt taaaaaaact gccacatgtc ctattttat tattattta         120 ctacacctta agggtatgta ttacctattc aaccttgctn atggagacta aacaagccac       180
tagcagaatt ttccatggat acacacacag gccagtccaa taaagagtaa catactgtgg       240
caatatatga cnaatrcacg agcgcgcata tatatcataa tgacatattt gtcatactat       300
ggaagattct ttttcttttt taaatnacaa attagattat actgggcaac ttaaaccgtc       360
attcaggctc accaattaac aaccaataaa atgctaaaac caacactata tgtatatctg       420
```

```
agaaaatgca tacacatata aat                                            443

<210> SEQ ID NO 112
<211> LENGTH: 443
<212> TYPE: DNA
<213> ORGANISM: Gossypium hirsutum
<220> FEATURE:
<221> NAME/KEY: unsure
<222> LOCATION: (1)..(443)
<223> OTHER INFORMATION: unsure at all n locations

<400> SEQUENCE: 112
cactatacac gcgcacacat atatataggg ttcgaattcg gtacacctag caatacaatc     60
ttttaactcc acaaaggagt taaaaaaact gccacatgtc ctatttttat tattatttta   120
ctcaccctta agggtatgta ttacctattc aaccttgctn atggagacta acaagccac    180 tagcagaatt ttccatggat acacacacag gccagtccaa taaagagtaa catactgtgg   240
caatatatga cnaatncacg agcgcgcata tatatcataa tgacatattt gtcatactat   300
ggaagattct ttttcttttt taaatmacaa attagattat actgggcaac ttaaaccgtc   360
attcaggctc accaattaac aaccaataaa atgctaaaac caacactata tgtatatctg   420
agaaaatgca tacacatata aat                                           443

<210> SEQ ID NO 113
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 113
ccactgttga aactccatct gagat                                           25

<210> SEQ ID NO 114
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 114
ggctaaagtt ggatcttggg atcta                                           25

<210> SEQ ID NO 115
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 115
acccttttgt tgcttttggg tgataat                                         27

<210> SEQ ID NO 116
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 116
```

```
ccatcgtttc attgcacaag tca                                           23
```

<210> SEQ ID NO 117
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 117

```
tgcaccgcaa acatggaatt tt                                            22
```

<210> SEQ ID NO 118
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 118

```
acttggacaa aacgaattcc tggaa                                         25
```

<210> SEQ ID NO 119
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 119

```
ccaacttttg atcggcaatg gt                                            22
```

<210> SEQ ID NO 120
<211> LENGTH: 28
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 120

```
tgggtaagtt ttccttcttt ctcctttt                                      28
```

<210> SEQ ID NO 121
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 121

```
ccaatgcaag tgacccaatt ctaaa                                         25
```

<210> SEQ ID NO 122
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 122

```
aatgataaaa acacacctca gttcttcct                                     29
```

```
<210> SEQ ID NO 123
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 123
cttattcata aacagaatgc ctctagtact gt                                    32

<210> SEQ ID NO 124
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 124
catacatagt acgaagagca ggagttg                                          27

<210> SEQ ID NO 125
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 125
cccgggcttc aaaggatga                                                   19

<210> SEQ ID NO 126
<211> LENGTH: 34
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 126
gcttatatac ttattgtttc tcgtttcttt ctgg                                  34

<210> SEQ ID NO 127
<211> LENGTH: 33
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 127
cacttaccta cctccattaa ttacattgaa act                                   33

<210> SEQ ID NO 128
<211> LENGTH: 33
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 128
ccgaaattta caaatcaaaa ctctgaacaa aat                                   33

<210> SEQ ID NO 129
```

```
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 129
cggtggcgca tggc                                                        14

<210> SEQ ID NO 130
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 130
ccaagatact ggctgggaag ag                                               22

<210> SEQ ID NO 131
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 131
gtggtaaact acttaaccaa tcttgtccta                                       30

<210> SEQ ID NO 132
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 132
acagcatgga gtgatgcatt actta                                            25

<210> SEQ ID NO 133
<211> LENGTH: 31
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 133
agtgtttaca taccataggg aatttgtttg t                                     31

<210> SEQ ID NO 134
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 134
agaaaagcat aatgccttgt tgtttaaca                                        29

<210> SEQ ID NO 135
<211> LENGTH: 25
<212> TYPE: DNA
```

```
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 135
cctgcacaaa acgtttacag agaat                                              25

<210> SEQ ID NO 136
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 136
caaatctgta gacgcacgat cga                                                23

<210> SEQ ID NO 137
<211> LENGTH: 31
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 137
cccttcaata catggaaaaa cttagaaaac a                                       31

<210> SEQ ID NO 138
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 138
ccttcaacac cagacgaagc t                                                  21

<210> SEQ ID NO 139
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 139
ccgccgcatc cgtca                                                         15

<210> SEQ ID NO 140
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 140
caacactttt ggctgcatgg t                                                  21

<210> SEQ ID NO 141
<211> LENGTH: 25
<212> TYPE: DNA
<213> ORGANISM: Artificial sequence
<220> FEATURE:
```

```
<223> OTHER INFORMATION: forward primers (113-180), reverse primers
      (181-248), and probes (249-316, 317-384) for SEQ ID NOs: 1-68

<400> SEQUENCE: 141
ggtgagatcg gtaccatagt accat                                          25

<210> SEQ ID NO 142
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 142
aacacgggca agagatgct                                                 19

<210> SEQ ID NO 143
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 143
caagtaggac gtgcgcaatg                                                20

<210> SEQ ID NO 144
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 144
caaacaagca acttattcac agatattgga                                     30

<210> SEQ ID NO 145
<211> LENGTH: 31
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 145
aacgactcat catctgatct gagttaaaat t                                   31

<210> SEQ ID NO 146
<211> LENGTH: 35
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 146
ctttgaatat ttgtttcaat tgcgaaatta gttga                               35

<210> SEQ ID NO 147
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68
```

```
<400> SEQUENCE: 147
gagaggttcg acttggaaag ct                                            22

<210> SEQ ID NO 148
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 148
gaagatgtac caaaggcatt gcat                                          24

<210> SEQ ID NO 149
<211> LENGTH: 34
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 149
cctagtcctc accaaaatca atcatttaaa agta                               34

<210> SEQ ID NO 150
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 150
cgaggttagg caatctgtct tttttatt                                      29

<210> SEQ ID NO 151
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 151
catgactata actgcaccag gctat                                         25

<210> SEQ ID NO 152
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 152
gaacaaccat ctgttgaaat cttttgc                                       27

<210> SEQ ID NO 153
<211> LENGTH: 28
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 153
```

```
tgacacagca ttttcttaca ctgttttg                                      28

<210> SEQ ID NO 154
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 154
caagtcatcc atttaaggaa actccaaaa                                     29

<210> SEQ ID NO 155
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 155
cccactctct cttaacaaca tcaca                                         25

<210> SEQ ID NO 156
<211> LENGTH: 26
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 156
acagggattg ttctatggtt gattcc                                        26

<210> SEQ ID NO 157
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 157
gaagtcccct cggtgataag tc                                            22

<210> SEQ ID NO 158
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 158
tcaaccagta gatctccaat aaacttaaat gg                                 32

<210> SEQ ID NO 159
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 159
acagctgaca caatatgtag agaagatttc                                    30
```

```
<210> SEQ ID NO 160
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 160
cgtgctaaga atttgcttga tgaaacc                                       27

<210> SEQ ID NO 161
<211> LENGTH: 33
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 161
ctacacctta agggtatgta ttacctattc aac                                33

<210> SEQ ID NO 162
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 162
gagtccttgt aggatcatat ccccata                                       27

<210> SEQ ID NO 163
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 163
ggcttccgtc tcctccttta ga                                            22

<210> SEQ ID NO 164
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 164
gctgcaagat attgtctccc agaaa                                         25

<210> SEQ ID NO 165
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 165
gtcactgttt gattctgttg ttgca                                         25
```

```
<210> SEQ ID NO 166
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 166
ggtggtggca gataaagata ttgca                                         25

<210> SEQ ID NO 167
<211> LENGTH: 26
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 167
ccatcattag ttgggccttt caattg                                        26

<210> SEQ ID NO 168
<211> LENGTH: 38
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 168
gacattaaga tgaaagaatg aaaatgttaa ccttaaga                           38

<210> SEQ ID NO 169
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 169
gcatctgaaa acgtaatgat ttagcaaga                                     29

<210> SEQ ID NO 170
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 170
gcccctgacg catgttctag                                               20

<210> SEQ ID NO 171
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 171
ttacgaacca cctttgaact gtga                                          24

<210> SEQ ID NO 172
<211> LENGTH: 22
```

```
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 172
ggcatacctg gaaacctgca at                                              22

<210> SEQ ID NO 173
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 173
caagaaaaaa ctgttgctct atgctatca                                       29

<210> SEQ ID NO 174
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 174
gcgcgagcat attcaacttt aacaa                                           25

<210> SEQ ID NO 175
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 175
actgttcctc ttgctagtga ggtat                                           25

<210> SEQ ID NO 176
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 176
tgacgaaact tcaagctaaa acattgc                                         27

<210> SEQ ID NO 177
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 177
agccgttgaa taaatgcatg cttaaag                                         27

<210> SEQ ID NO 178
<211> LENGTH: 26
<212> TYPE: DNA
<213> ORGANISM: Artificial sequence
```

```
<220> FEATURE:
<223> OTHER INFORMATION: forward primers (113-180), reverse primers
      (181-248), and probes (249-316, 317-384) for SEQ ID NOs: 1-68

<400> SEQUENCE: 178
aacttctaat cccatggtct gagaga                                          26

<210> SEQ ID NO 179
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 179
aggcaaggcc cctcaac                                                    17

<210> SEQ ID NO 180
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 180
acgcaccgga aatgaaagag a                                               21

<210> SEQ ID NO 181
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 181
agagcagcag aaaccacgaa t                                               21

<210> SEQ ID NO 182
<211> LENGTH: 35
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 182
aacagatgaa aactaaccat ttctaaacac aattt                                35

<210> SEQ ID NO 183
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 183
gaaagattgc attccagtaa ccagaat                                         27

<210> SEQ ID NO 184
<211> LENGTH: 29
<212> TYPE: DNA
<213> ORGANISM: Artificial sequence
<220> FEATURE:
<223> OTHER INFORMATION: forward primers (113-180), reverse primers
```

(181-248), and probes (249-316, 317-384) for SEQ ID NOs: 1-68

<400> SEQUENCE: 184
gagaatcaat aagtttgctt gttggacaa                                29

<210> SEQ ID NO 185
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 185
aagagaaaag gttccaagac accaa                                    25

<210> SEQ ID NO 186
<211> LENGTH: 34
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 186
tcatcacaga aacaagtttt atataagagg aaca                          34

<210> SEQ ID NO 187
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 187
cagaaatcaa atttttacag acatagggaa ca                            32

<210> SEQ ID NO 188
<211> LENGTH: 35
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 188
agttgatttt aaatctcatt tttgggttct ctttt                         35

<210> SEQ ID NO 189
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 189
ccttgctgct cggagctt                                            18

<210> SEQ ID NO 190
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

```
<400> SEQUENCE: 190
acaggttgca tacttgctga gtt                                              23

<210> SEQ ID NO 191
<211> LENGTH: 27
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 191
tgatgacgac tatttgcata tgttcga                                          27

<210> SEQ ID NO 192
<211> LENGTH: 31
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 192
aaaaaatgat attaccatgg agatgagtgg t                                     31

<210> SEQ ID NO 193
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 193
cgtatcccct tcatttcgtc gaa                                              23

<210> SEQ ID NO 194
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 194
gacaacatga caacgtacga caa                                              23

<210> SEQ ID NO 195
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 195
ggttggtaat gtacttgatg taattttgtt ga                                    32

<210> SEQ ID NO 196
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 196
```

```
cgccttttcc ggagaagata tctc                                              24
```

<210> SEQ ID NO 197
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 197

```
acggcgtcat ttcatattgt tataaaagc                                         29
```

<210> SEQ ID NO 198
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 198

```
gtctggccat ggattagcct tt                                                22
```

<210> SEQ ID NO 199
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 199

```
aactttgtgg tatgtaagaa ggatcgtaag                                        30
```

<210> SEQ ID NO 200
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 200

```
ttcctatatg gcgaagtgtt ggg                                               23
```

<210> SEQ ID NO 201
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 201

```
gcatcccaaa ggactatcat atcca                                             25
```

<210> SEQ ID NO 202
<211> LENGTH: 26
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 202

```
actccaacct aaacacctct acttct                                            26
```

<210> SEQ ID NO 203
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 203
ggctttcact tgtcgatagg tttca                                            25

<210> SEQ ID NO 204
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 204
cagaatctac gacgtcaaac acttg                                            25

<210> SEQ ID NO 205
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 205
gatattcgag cccatgttac ttgga                                            25

<210> SEQ ID NO 206
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 206
cccagataac aggacctctt cac                                              23

<210> SEQ ID NO 207
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 207
gcttgtaagg cattgagaca ttgg                                             24

<210> SEQ ID NO 208
<211> LENGTH: 33
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 208
catccctccc tattatttta tctttactca caa                                   33

<210> SEQ ID NO 209

<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 209
cgcttctaac gggaaccaag a                                      21

<210> SEQ ID NO 210
<211> LENGTH: 26
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 210
tccagtagcc ctttctatac caagat                                 26

<210> SEQ ID NO 211
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 211
gcaaaaggaa aatccattac tagtttaaga ct                          32

<210> SEQ ID NO 212
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 212
cagatcttgg gtttaggctc aaagt                                  25

<210> SEQ ID NO 213
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 213
caagctgttg atggcccata g                                      21

<210> SEQ ID NO 214
<211> LENGTH: 26
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 214
acagcctgaa acatcaaatc cttact                                 26

<210> SEQ ID NO 215
<211> LENGTH: 27
<212> TYPE: DNA

```
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 215
gggagaaaac tagtaaaaca cggttgt                                          27

<210> SEQ ID NO 216
<211> LENGTH: 41
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 216
tcatttcaat aaagtaagtg ttaagacata ctagatagag a                          41

<210> SEQ ID NO 217
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 217
aagtgaaaat gttaatgaaa tgaacgaggt tt                                    32

<210> SEQ ID NO 218
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 218
gctaaagcca ataaactctc ttacaaatgg                                       30

<210> SEQ ID NO 219
<211> LENGTH: 28
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 219
gcatgctctt gttggatata tacccata                                         28

<210> SEQ ID NO 220
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 220
tgatgagaac ttgcggaaaa tcca                                             24

<210> SEQ ID NO 221
<211> LENGTH: 32
<212> TYPE: DNA
<213> ORGANISM: Artificial sequence
<220> FEATURE:
```

-continued

<223> OTHER INFORMATION: forward primers (113-180), reverse primers
     (181-248), and probes (249-316, 317-384) for SEQ ID NOs: 1-68

<400> SEQUENCE: 221
aaggctactc gggaaaaaga ataacataaa ta                                    32

<210> SEQ ID NO 222
<211> LENGTH: 26
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 222
acttcgcgat tcagtagttc tacttg                                          26

<210> SEQ ID NO 223
<211> LENGTH: 31
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 223
gaccacatgc atagcataac tttttaattc a                                     31

<210> SEQ ID NO 224
<211> LENGTH: 27
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 224
acgaggaatt ctcttctctg tacttct                                         27

<210> SEQ ID NO 225
<211> LENGTH: 24
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 225
cgttattgtg ctgtctcaga tgct                                            24

<210> SEQ ID NO 226
<211> LENGTH: 27
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 226
gtccgaattt gaaattggac aaggaaa                                         27

<210> SEQ ID NO 227
<211> LENGTH: 25
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

```
<400> SEQUENCE: 227
agatcactac ctactgctct tgcat                                              25

<210> SEQ ID NO 228
<211> LENGTH: 28
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 228
cggattaatc ttccgtatca agttgaga                                           28

<210> SEQ ID NO 229
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 229
gcctgtgtgt gtatccatgg aaaat                                              25

<210> SEQ ID NO 230
<211> LENGTH: 36
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 230
ggtttagttc attggaaact atattactct gattct                                  36

<210> SEQ ID NO 231
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 231
agacctgcga gagctccat                                                     19

<210> SEQ ID NO 232
<211> LENGTH: 33
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 232
taacatttgg ttattttatt gtccagatca tga                                     33

<210> SEQ ID NO 233
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 233
```

```
ggtcagatga acggcaacac t                                              21

<210> SEQ ID NO 234
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 234
cactttggag ataccctttc aggaa                                          25

<210> SEQ ID NO 235
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 235
gttggcttgc cggtaacc                                                  18

<210> SEQ ID NO 236
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 236
catgtgctcc ggagattctt ca                                             22

<210> SEQ ID NO 237
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 237
cgagatcgat ctcacttggt tgaat                                          25

<210> SEQ ID NO 238
<211> LENGTH: 24
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 238
gccattcatg tatcgcatca tctt                                           24

<210> SEQ ID NO 239
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 239
tcacaatgcc gccgctaata a                                              21
```

<210> SEQ ID NO 240
<211> LENGTH: 28
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 240
ccgtttaatt ttagccactg aacatctt                                      28

<210> SEQ ID NO 241
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 241
ccacaggaaa tcctctatgg tactg                                         25

<210> SEQ ID NO 242
<211> LENGTH: 32
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 242
tgtaaagtca ttacaatttt tctaggacga ct                                 32

<210> SEQ ID NO 243
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 243
ccacatgcac agaattttga acaca                                         25

<210> SEQ ID NO 244
<211> LENGTH: 25
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 244
gatgaaggag tgcgaagaag taagt                                         25

<210> SEQ ID NO 245
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 245
tgcaactggc actcaggtaa g                                             21

```
<210> SEQ ID NO 246
<211> LENGTH: 30
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 246
tggttacatt atctgatggt atttgcactt                                    30

<210> SEQ ID NO 247
<211> LENGTH: 29
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 247
ccaatcatcg gcttctatct attagttca                                     29

<210> SEQ ID NO 248
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 248
ccggcggctt ccca                                                     14

<210> SEQ ID NO 249
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 249
cattcacgga atagatg                                                  17

<210> SEQ ID NO 250
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 250
ccagagttga ctattg                                                   16

<210> SEQ ID NO 251
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 251
ttagtatctt tatagcaaac ct                                            22

<210> SEQ ID NO 252
<211> LENGTH: 16
```

```
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 252
ctgttgtgaa acttga                                                         16

<210> SEQ ID NO 253
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 253
aatacgagtc agtcagca                                                       18

<210> SEQ ID NO 254
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 254
aattgactgg atcgaatc                                                       18

<210> SEQ ID NO 255
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 255
tccctacatg atcaatag                                                       18

<210> SEQ ID NO 256
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 256 ataaaaaga aaaccaaaag aa                                                   22

<210> SEQ ID NO 257
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 257
cttgaaaaca taagaagacc a                                                   21

<210> SEQ ID NO 258
<211> LENGTH: 20
<212> TYPE: DNA
<213> ORGANISM: Artificial sequence
```

```
<220> FEATURE:
<223> OTHER INFORMATION: forward primers (113-180), reverse primers
      (181-248), and probes (249-316, 317-384) for SEQ ID NOs: 1-68

<400> SEQUENCE: 258
cataataggc ttgccagcat                                              20

<210> SEQ ID NO 259
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 259
ctccttgtag accttctt                                                18

<210> SEQ ID NO 260
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 260
aagaagcagt agattat                                                 17

<210> SEQ ID NO 261
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 261
cccacgactg aaatg                                                   15

<210> SEQ ID NO 262
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 262
acaaaccacc taatacc                                                 17

<210> SEQ ID NO 263
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 263
ctatactagc acaatttgta                                              20

<210> SEQ ID NO 264
<211> LENGTH: 16
<212> TYPE: DNA
<213> ORGANISM: Artificial sequence
<220> FEATURE:
<223> OTHER INFORMATION: forward primers (113-180), reverse primers
```

(181-248), and probes (249-316, 317-384) for SEQ ID NOs: 1-68

<400> SEQUENCE: 264
ccggttgttt ttggct                                                    16

<210> SEQ ID NO 265
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 265
cggtgagact ccagcac                                                   17

<210> SEQ ID NO 266
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 266
ctattattag gcaagattaa                                                20

<210> SEQ ID NO 267
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 267
tcacattaaa tgaaagatg                                                 19

<210> SEQ ID NO 268
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 268
cctggaagtt actgactg                                                  18

<210> SEQ ID NO 269
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 269
actgtaaaca gaagccca                                                  18

<210> SEQ ID NO 270
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

```
<400> SEQUENCE: 270
catgctaatt agatttt                                                    17

<210> SEQ ID NO 271
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 271
ttttccctta caacatacac                                                 20

<210> SEQ ID NO 272
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 272
acctccatgt aatcc                                                      15

<210> SEQ ID NO 273
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 273
tttgggcgag tttc                                                       14

<210> SEQ ID NO 274
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 274
tcttgattcg gctcgtc                                                    17

<210> SEQ ID NO 275
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 275
ccgccaattt gatc                                                       14

<210> SEQ ID NO 276
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 276
```

```
cactgggcgg tcac                                                     14
```

<210> SEQ ID NO 277
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 277

```
aaggccatat tgaggtc                                                  17
```

<210> SEQ ID NO 278
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 278

```
ctggatggca tttag                                                    15
```

<210> SEQ ID NO 279
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 279

```
attgacacag agtttg                                                   16
```

<210> SEQ ID NO 280
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 280

```
cgatgaacac taataaat                                                 18
```

<210> SEQ ID NO 281
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 281

```
tttgaatagt ctccaagcaa                                               20
```

<210> SEQ ID NO 282
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 282

```
catacgattc gcatttt                                                  17
```

-continued

```
<210> SEQ ID NO 283
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 283
tccctaacga atcaa                                                        15

<210> SEQ ID NO 284
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 284
atttgcaact tgattatgtt ga                                                22

<210> SEQ ID NO 285
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 285
acaacattcc cgttttt                                                      17

<210> SEQ ID NO 286
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 286
tcgtttttgc gtttttt                                                      17

<210> SEQ ID NO 287
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 287
actcgggaat gagtatag                                                     18

<210> SEQ ID NO 288
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 288
cagttgggcg gcaaa                                                        15

<210> SEQ ID NO 289
```

```
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 289 cttttattt ttcgtaaggc c                                          21

<210> SEQ ID NO 290
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 290
acgcatcccc ggatta                                               16

<210> SEQ ID NO 291
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 291
agattggtgt cttgtgtgtg                                           20

<210> SEQ ID NO 292
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 292
tctcaagtcc gtctggc                                              17

<210> SEQ ID NO 293
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 293
acaaattctt cgtaaggaa                                            19

<210> SEQ ID NO 294
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 294
ctttgagttg acattatc                                             18

<210> SEQ ID NO 295
<211> LENGTH: 21
<212> TYPE: DNA
```

```
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 295
atcctcaaaa tctttcctct c                                              21

<210> SEQ ID NO 296
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 296
catagtccga ggaatc                                                    16

<210> SEQ ID NO 297
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 297
tgtttagtct ccatgagcaa g                                              21

<210> SEQ ID NO 298
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 298
cgtgttttga tgcttatc                                                  18

<210> SEQ ID NO 299
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 299
tttgctcaac cgacagca                                                  18

<210> SEQ ID NO 300
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 300
ccggcttctt aacttta                                                   17

<210> SEQ ID NO 301
<211> LENGTH: 16
<212> TYPE: DNA
<213> ORGANISM: Artificial sequence
<220> FEATURE:
```

-continued

<223> OTHER INFORMATION: forward primers (113-180), reverse primers
     (181-248), and probes (249-316, 317-384) for SEQ ID NOs: 1-68

<400> SEQUENCE: 301
ttgcggcaca tatgta                                                    16

<210> SEQ ID NO 302
<211> LENGTH: 19
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 302
attttgtcac cactcctac                                                 19

<210> SEQ ID NO 303
<211> LENGTH: 18
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 303
atggcggtat gttctgga                                                  18

<210> SEQ ID NO 304
<211> LENGTH: 16
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 304
ccagcaaaga gtttat                                                    16

<210> SEQ ID NO 305
<211> LENGTH: 21
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 305
cactctgaga taataattca a                                              21

<210> SEQ ID NO 306
<211> LENGTH: 17
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

<400> SEQUENCE: 306
catacatgtt gaagctt                                                   17

<210> SEQ ID NO 307
<211> LENGTH: 20
<212> TYPE: DNA
<213> ORGANISM: Artificial sequence
<220> FEATURE:
<223> OTHER INFORMATION: forward primers (113-180), reverse primers
     (181-248), and probes (249-316, 317-384) for SEQ ID NOs: 1-68

```
<400> SEQUENCE: 307
tttccgtatt caattaaaca                                                  20

<210> SEQ ID NO 308
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 308
caattgtgga tctgatctg                                                   19

<210> SEQ ID NO 309
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 309
ctgagaagac ggtcaatt                                                    18

<210> SEQ ID NO 310
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 310
ccattactgt caaaatga                                                    18

<210> SEQ ID NO 311
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 311
ataagcattc gtaaaatgta                                                  20

<210> SEQ ID NO 312
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 312
caattttatg gtacaagata c                                                21

<210> SEQ ID NO 313
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 313
```

```
cacatgcagg tttgtg                                              16
```

<210> SEQ ID NO 314
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 314

```
aagatgacag cattcg                                              16
```

<210> SEQ ID NO 315
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 315

```
ctaccaagat aatcaggcac g                                        21
```

<210> SEQ ID NO 316
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 316

```
ttcaccagta attaaac                                             17
```

<210> SEQ ID NO 317
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 317

```
ttcacggcat agatg                                               15
```

<210> SEQ ID NO 318
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 318

```
cagagttggc tattg                                               15
```

<210> SEQ ID NO 319
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 319

```
tctttatggc aaacct                                              16
```

```
<210> SEQ ID NO 320
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 320
cctgttgtga tacttga                                                  17

<210> SEQ ID NO 321
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 321
atacgagtcg gtcagca                                                  17

<210> SEQ ID NO 322
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 322
ttgactgggt cgaatc                                                   16

<210> SEQ ID NO 323
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 323
cctacatgag caatag                                                   16

<210> SEQ ID NO 324
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 324
aaaagaaaac cgaaagaa                                                 18

<210> SEQ ID NO 325
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 325
ttgaaaacat aaaagacca                                                20
```

-continued

```
<210> SEQ ID NO 326
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 326
cataataggc tttccagcat                                                  20

<210> SEQ ID NO 327
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 327
ccttgtagag cttctt                                                      16

<210> SEQ ID NO 328
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 328
aagaagcagt tgattat                                                     17

<210> SEQ ID NO 329
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 329
ccacgaccga aatg                                                        14

<210> SEQ ID NO 330
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 330
aaaccaccca atacc                                                       15

<210> SEQ ID NO 331
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 331
ctatactagc acattttgta                                                  20

<210> SEQ ID NO 332
<211> LENGTH: 15
```

```
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 332
cggttgttgt tggct                                                     15

<210> SEQ ID NO 333
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 333
cggtgagact cagcac                                                    16

<210> SEQ ID NO 334
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 334
ttattaggcg agattaa                                                   17

<210> SEQ ID NO 335
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 335
atcacattaa ataaaagatg                                                20

<210> SEQ ID NO 336
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 336
ctggaggtta ctgactg                                                   17

<210> SEQ ID NO 337
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 337
ctgtaaacac aagccca                                                   17

<210> SEQ ID NO 338
<211> LENGTH: 16
<212> TYPE: DNA
<213> ORGANISM: Artificial sequence
```

```
<220> FEATURE:
<223> OTHER INFORMATION: forward primers (113-180), reverse primers
      (181-248), and probes (249-316, 317-384) for SEQ ID NOs: 1-68

<400> SEQUENCE: 338
atgctaatga gatttt                                                        16

<210> SEQ ID NO 339
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 339
tttcccttac aacttacac                                                     19

<210> SEQ ID NO 340
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 340
cctccgtgta atcc                                                          14

<210> SEQ ID NO 341
<211> LENGTH: 13
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 341
ttgggcaagt ttc                                                           13

<210> SEQ ID NO 342
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 342
atcttgattc agctcgtc                                                      18

<210> SEQ ID NO 343
<211> LENGTH: 14
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 343
ccgccagttt gatc                                                          14

<210> SEQ ID NO 344
<211> LENGTH: 15
<212> TYPE: DNA
<213> ORGANISM: Artificial sequence
<220> FEATURE:
<223> OTHER INFORMATION: forward primers (113-180), reverse primers
```

-continued (181-248), and probes (249-316, 317-384) for SEQ ID NOs: 1-68

<400> SEQUENCE: 344
ccactaggcg gtcac                                                15

<210> SEQ ID NO 345
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 345
aaggccataa tgaggtc                                              17

<210> SEQ ID NO 346
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 346
actggatagc atttag                                               16

<210> SEQ ID NO 347
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 347
ttgacacgga gtttg                                                15

<210> SEQ ID NO 348
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 348
atgaacacaa ataaat                                               16

<210> SEQ ID NO 349
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 349
tttttgaata gtctccgagc aa                                        22

<210> SEQ ID NO 350
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

```
<400> SEQUENCE: 350
aacatacgat tagcatttt                                                  19

<210> SEQ ID NO 351
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 351
tccctaagga atcaa                                                      15

<210> SEQ ID NO 352
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 352
atttgcaact tgattttgtt ga                                              22

<210> SEQ ID NO 353
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 353
aacatccccg ttttt                                                      15

<210> SEQ ID NO 354
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 354 ttcgttttg cttttttt                                                    18

<210> SEQ ID NO 355
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 355
actcgggaat aagtatag                                                   18

<210> SEQ ID NO 356
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 356
```

-continued

```
cagttgggca gcaaa                                              15

<210> SEQ ID NO 357
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 357 cttttttattt ttcataaggc c                                      21

<210> SEQ ID NO 358
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 358
acgcatcctc ggatta                                             16

<210> SEQ ID NO 359
<211> LENGTH: 20
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 359
agattggtgt cttatgtgtg                                         20

<210> SEQ ID NO 360
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 360
ctcaagtcca tctggc                                             16

<210> SEQ ID NO 361
<211> LENGTH: 23
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 361
ttttacaaat tcttcataag gaa                                     23

<210> SEQ ID NO 362
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 362
ttgagtcgac attatc                                             16
```

```
<210> SEQ ID NO 363
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 363
cctcaaaatc tctcctctc                                                    19

<210> SEQ ID NO 364
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 364
catagtccaa ggaatc                                                       16

<210> SEQ ID NO 365
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 365
tgtttagtct ccatcagcaa g                                                 21

<210> SEQ ID NO 366
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 366
ccgtgttttg attcttatc                                                    19

<210> SEQ ID NO 367
<211> LENGTH: 19
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 367
ctttgctcaa cctacagca                                                    19

<210> SEQ ID NO 368
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 368
cggcttctca acttta                                                       16

<210> SEQ ID NO 369
```

<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 369
ttgcggcacg tatgta                                                         16

<210> SEQ ID NO 370
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 370
ttgtcaccgc tcctac                                                         16

<210> SEQ ID NO 371
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 371
atggcggtat attctgga                                                       18

<210> SEQ ID NO 372
<211> LENGTH: 15
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 372
cagcaaagcg tttat                                                          15

<210> SEQ ID NO 373
<211> LENGTH: 21
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 373
cactctgaga taatagttca a                                                   21

<210> SEQ ID NO 374
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 374
catacatgtt caagctt                                                        17

<210> SEQ ID NO 375
<211> LENGTH: 18
<212> TYPE: DNA

```
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 375
tccgtattca actaaaca                                                    18

<210> SEQ ID NO 376
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 376
attgtggatc cgatctg                                                     17

<210> SEQ ID NO 377
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 377
ctgagaagac agtcaatt                                                    18

<210> SEQ ID NO 378
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 378
cattactgtc gaaatga                                                     17

<210> SEQ ID NO 379
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 379
agcattcgta caatgta                                                     17

<210> SEQ ID NO 380
<211> LENGTH: 22
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 380
acaattttat ggtataagat ac                                               22

<210> SEQ ID NO 381
<211> LENGTH: 16
<212> TYPE: DNA
<213> ORGANISM: Artificial sequence
<220> FEATURE:
```

-continued

```
<223> OTHER INFORMATION: forward primers (113-180), reverse primers
      (181-248), and probes (249-316, 317-384) for SEQ ID NOs: 1-68

<400> SEQUENCE: 381
cacatgcagt tttgtg                                                   16

<210> SEQ ID NO 382
<211> LENGTH: 16
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 382
aagatgacaa cattcg                                                   16

<210> SEQ ID NO 383
<211> LENGTH: 18
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 383
ccaagataat cgggcacg                                                 18

<210> SEQ ID NO 384
<211> LENGTH: 17
<212> TYPE: DNA
<213> ORGANISM: Artificial sequence
<220> FEATURE:
<223> OTHER INFORMATION: forward primers (113-180), reverse primers
      (181-248), and probes (249-316, 317-384) for SEQ ID NOs: 1-68

<400> SEQUENCE: 384
ttcaccagta tttaaac                                                  17
```

METHODS OF QUANTIFYING TARGET ORGANISMS AND CREATING RENIFORM RESISTANT COTTON PLANTS

CROSS-REFERENCE TO RELATED APPLICATIONS

This application claims the benefit of U.S. Provisional Application No. 61/250,235, filed on Oct. 9, 2009. The entire disclosure of the above application is incorporated herein by reference.

INCORPORATION OF SEQUENCE LISTING

The sequence listing contained in the file named "55576_RenSeqs.txt", which is 188 kilobytes (measured in MS-Windows®) created on Oct. 11, 2010, is filed herewith by electronic submission and incorporated herein by reference.

FIELD OF THE INVENTION

Disclosed herein are methods of quantifying plant pathogens present at a given location, particularly plant pathogens that spend at least part of their life cycle in the rhizosphere of crop plants. Embodiments of the invention comprise methods of comparing the amount of DNA sequence that is specific to a target organism in a sample of matter to the total amount of DNA in the sample of matter to quantify the relative amount of the target organism present in the sample of matter. Non-limiting examples are provided that disclose novel methods of quantifying both the absolute number, and the relative number, of reniform nematodes (*Rotylenchulus reniformis*) and/or root knot nematodes (*Meloidogyne incognita*), present in a sample of matter, e.g. soil. This invention facilitates disease management and research by allowing a user to quickly assess the risk of planting a crop at a given location, determine how best to treat crops already growing at a given location in response to infestation, anticipate and track the development of infestation within or among locations, and to study the variability of a plant or plant population to resist reniform infection.

Other embodiments of the invention comprise molecular markers useful for detecting nucleotide sequences in cotton plants associated with reniform resistance and methods of introgressing those sequences from one plant into another to produce novel germplasm comprising one or more reniform resistance loci.

SUMMARY OF THE INVENTION

The invention disclosed herein comprises a rapid method of determining the level of target organisms in a sample of matter. This Infection Index Method comprises deriving relationships between the total amount of DNA detected in a sample to the amount of DNA in the sample detected by PCR amplification of a sequence that is specific to the target organism, and using that relationship, or any mathematical permutations of that relationship, to quantify the amount of target organism in the sample.

The invention also provides descriptions of how the Infection Index Method can be used to monitor reniform infestation at one or more locations so that more effective planting, reniform treatment, and resource allocation plans can be made for one or more growing locations.

The invention further provides a description of how the infection index for a location can be used to estimate a plant's ability to resist infection to disease.

Furthermore, this invention describes how the Infection Index Method can be used to help identify disease resistance alleles in cotton genomic DNA, help genotype a cotton plant with respect to the presence or absence of those alleles, aid breeders in tracking those alleles in a population of cotton plants as they are inherited from generation to generation, and provide information to make decisions about which individuals to select for advancement in a breeding program.

Certain aspects of this invention further include novel single nucleotide polymorphic (SNP) markers useful for detecting the presence of reniform resistance alleles in a plant, or a population of plants, as part of a molecular assisted breeding program. The SNP markers disclosed herein allow a breeder to genotype a plant for presence of nucleotide sequences associated with reniform resistance, thereby reducing or even bypassing less efficient phenotyping processes.

DETAILED DESCRIPTION OF THE INVENTION

The invention disclosed herein comprises a novel and high-throughput method of determining the amount of target organism at a given location. The method is considerably more efficient and more accurate than methods presently or previously disclosed in the art.

This Infection Index Method comprises quantifying the number of target organisms in a sample of matter by comparing the amount of DNA detected with a sequence specific to a target organism to the total amount of DNA detected in the sample of matter.

In one embodiment of the Infection Index Method, the DNA sequence that is specific to the target organism is the ITS1 (internal transcribed spacer 1) region 5.8S rRNA gene of the reniform nematode *Rotylenchulus reniformis*. In another embodiment, the pest-specific nucleic acid sequence detected is the ITS1 region 5.8 S rRNA gene of the root knot nematode *Meloidogyne incognita*. In other embodiments, the pest-specific nucleic acid sequences detected are specific to other organisms.

Additional embodiments of the disclosed invention include phenotyping a plant as to its susceptibility or resistance to nematodes based on the level of nematode infestation detected in the rhizosphere of the plant using the Infection Index Method.

Previous methods described in the art, such as the Baermann Funnel Extraction Technique (BFET), typically result in complete removal of the plant from the growing location in order to collect soil. This invention provides a novel high-throughput and accurate way of determining a plant's ability to resist infection by specific pests without disturbing the plant from where it grows. Thus, the ability of a plant to resist infection can be assayed multiple times over a growing period through sequential soil sampling and the spread of infestation can be monitored over time.

The present invention also provides methods of incorporating the Infection Index Method into conventional breeding efforts to facilitate the introgression of favorable alleles from one plant into another. In one embodiment, this process comprises the steps of: 1) making crosses between parental lines; 2) phenotyping the offspring produced from those crosses using the Infection Index Method; and 3) making selections of parents and/or the offspring based on those phenotype scores.

Furthermore, the present invention provides a method of introgressing an allele associated with disease resistance into a plant line comprising the steps of: 1) providing a population of plants; 2) genotyping at least one plant in the population with respect to at least one genomic nucleic acid marker selected from the group comprising of SEQ ID NO: 1-112 and 3) selecting from the population at least one plant comprising at least one allele associated with the disease resistance. The population provided may be derived by crossing at least one disease resistant plant with at least one disease sensitive plant to form a population.

The present invention also provides for an elite plant produced by: 1) providing a population of plants; 2) genotyping at least one plant in the population with respect to a cotton genomic nucleic acid marker selected from the group comprising SEQ ID NO: 1-112; and 3) selecting from the population at least one plant comprising at least one allele associated with disease resistance. The elite cotton plant of the present invention can exhibit a transgenic trait.

The invention further provides a substantially purified nucleic acid molecule for the detection of loci related to disease resistance comprising a nucleic acid molecule selected from the group consisting of SEQ ID NO: 1-112 and complements thereof. The invention further provides an isolated nucleic acid molecule for detecting a molecular marker representing a polymorphism in cotton DNA, wherein the nucleic acid molecule comprises at least 15 nucleotides that include or are adjacent to the polymorphism, wherein the nucleic acid molecule is at least 90 percent identical to a sequence of the same number of consecutive nucleotides in either strand of DNA that include or are adjacent to the polymorphism, and wherein the molecular marker is selected from the group consisting of SEQ ID NO: 1-112. In one aspect, the isolated nucleic acid further comprises a detectable label or provides for incorporation of a detectable label. In a further aspect, the detectable label is selected from the group consisting of an isotope, a fluorophore, an oxidant, a reductant, a nucleotide and a hapten.

The present invention further provides a set of oligonucleotides comprising a) a pair of oligonucleotide primers wherein each of the primers comprises at least 12 contiguous nucleotides and wherein the pair of primers permit PCR amplification of a DNA segment comprising a molecular marker selected from the group consisting of SEQ ID NO: 1-112 and b) at least one detector oligonucleotide that permits detection of a polymorphism in the amplified segment, wherein the sequence of the detector oligonucleotide is at least 95 percent identical to a sequence of the same number of consecutive nucleotides in either strand of a segment of cotton DNA that include or are adjacent to the polymorphism of step (a).

Unless otherwise noted, terms are to be understood according to conventional usage by those of ordinary skill in the relevant art. Definitions of common terms in molecular biology may also be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press New York, 2007. The nomenclature for DNA bases as set forth at 37 CFR §1.822 is used.

The "rhizosphere" of a plant is the region of soil that is influenced by the plant's roots, root secretions, and root-associated soil microorganisms.

As used herein, "growing area" is any area or facility where plants are purposefully grown. Non-limiting examples include cultivated fields, greenhouses, growth chambers, pots, or any other industrial, academic, public or private setting where multiple plants are grown for study and/or consumption.

As used herein, a "location" is a specific site within a growing area. At least one embodiment of this invention describes collecting soil at multiple locations within a growing area. Non-limiting examples of such locations would be specific 2 ft by 2 ft sections in a particular field, or a seedling growing in a 2 in by 2 in section of a pot in a growth chamber.

As used herein, RKN means root knot nematode, or *Meloidogyne incognita*.

An "allele" refers to an alternative sequence at a particular locus; the length of an allele can be as small as 1 nucleotide base, but is typically larger.

A "locus" is a position on a genomic sequence that is usually found by a point of reference; e.g., a DNA sequence that is a gene, or part of a gene or intergenic region. The loci of this invention comprise one or more polymorphisms in a population; i.e., alternative alleles are present in some individuals.

As used herein, "polymorphism" means the presence of two or more variations of a nucleic acid sequence or nucleic acid feature at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may also comprise polymorphisms. In addition, the presence, absence, or variation in copy number of the preceding may comprise polymorphisms As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics. As used herein, "genetic marker" means polymorphic nucleic acid sequence or nucleic acid feature. A genetic marker may be represented by one or more particular variant sequences, or by a consensus sequence. In another sense, a "genetic marker" is an isolated variant or consensus of such a sequence.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given cotton genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the phrase "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein the polymorphism constitutes a single base pair change, an insertion of one or more base pairs, or a deletion of one or more base pairs.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" is the genetic constitution of an individual (or group of individuals) at one or more genetic loci, as contrasted with the observable trait (the phenotype). The genotype can be indirectly characterized, for example, by the use of genetic markers, or directly characterized, for example, by nucleic acid sequencing. Suitable markers include a phenotypic character, a metabolic profile, a genetic marker, or some other type of marker. Genotype is defined by the allele(s) of one or more known loci that the individual has inherited from its parents, or is capable of passing onto its offspring. The term genotype can be used to refer to an individual's genetic constitution at a single locus, at multiple loci, a portion of a chromosome, an entire chromosome, a portion of the genome, the entire genome, or, more generally, the term genotype can be used to refer to an individual's genetic make-up for all the genes in its genome. A genotype may constitute an allele for at least one genetic marker locus or a haplotype for at least one haplotype window.

Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

As used herein, "phenotype" means the detectable characteristics of a cell or organism which can be influenced by genotype.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, "resistance allele" means the nucleic acid sequence that includes the polymorphic allele associated with resistance to a disease.

As used herein, "cotton" means *Gossypium hirsutum* and includes all plant varieties that can be bred with cotton, including wild cotton species. More specifically, cotton plants from the species *Gossypium hirsutum* and the subspecies *Gossypium hirsutum* L. can be genotyped using these compositions and methods. In an additional aspect, the cotton plant is from the group *Gossypium arboreum* L., otherwise known as tree cotton. In another aspect, the cotton plant is from the group *Gossypium barbadense* L., otherwise known as American pima or Egyptian cotton. In another aspect, the cotton plant is from the group *Gossypium herbaceum* L., otherwise known as levant cotton. *Gossypium* or cotton plants can include hybrids, inbreds, partial inbreds, or members of defined or undefined populations.

As used herein, the term "comprising" means "including but not limited to".

As used herein, the term "elite line" means any line that has resulted from breeding and selection for superior agronomic performance. Non-limiting examples of elite lines that are commercially available include DP 555 BG/RR, DP 445 BG/RR, DP 444 BG/RR, DP 454 BG/RR, DP 161 B2RF, DP 141 B2RF, DP 0924 B2RF, DP 0935 B2RF, DP 121 RF, DP 174 RF (Deltapine); ST5599BR, ST5242BR, ST4554B2RF, ST4498B2RF, ST5458B2RF (Stoneville); FM9058F, FM9180B2F, FM1880B2F, FM1740B2F (FiberMax); PHY485WRF, PHY375WRF, PHY745WRF (Acala)(PhytoGen); and MCS0423B2RF, MCS0508B2RF (Cotton States).

In the present invention, a disease resistance locus is located on chromosome A11. SNP markers used to detect the presence of reniform nematode resistance and to monitor the introgression of the disease resistance locus comprise those selected from the group consisting of SEQ ID NO: 1-112. Forward primers used to amplify the SNPs in SEQ ID NO: 1-68 are provided in the sequence listing as SEQ ID NO: 113-180. Reverse primers used to amplify the SNPs in SEQ ID NO: 1-68 are listed in the same order in the sequence listing as SEQ ID NO: 181-248. Probe sets used to detect the SNPs in SEQ ID NO: 1-68 are also listed in the same order as SEQ ID NO: 249-316 and SEQ ID NO: 317-384, respectively.

For example, marker DNA sequence SEQ ID NO 3 can be amplified using the primers indicated as SEQ ID NO: 115 and 183 and detected with probes indicated as SEQ ID NO: 251 and 319. Illustrative example marker DNA sequence SEQ ID NO 12 can be amplified using the primers indicated as SEQ ID NO: 124 and 192 and detected with probes indicated as SEQ ID NO: 260 and 328. Illustrative example marker DNA sequence SEQ ID NO: 13 can be amplified using the primers indicated as SEQ ID NO: 125 and 193 and detected with probes indicated as SEQ ID NO: 261 and 329.

Furthermore, SEQ ID NO: 69-112 are additional SNP markers useful for detecting the presence of reniform nematode resistance and for monitoring the introgression of the disease resistance locus. Based on these sequences, one of ordinary skill in the art can order the reaction components necessary to detect the disclosed SNPs from several options of vendors specializing in such services or simply create the appropriate primers and probes using methods requiring ordinary skill in the art.

The present invention also provides a cotton plant comprising a nucleic acid molecule selected from the group consisting of SEQ ID NO: 1-112, fragments thereof, and complements of both. The present invention also provides an elite cotton plant comprising a nucleic acid molecule selected from the group consisting of SEQ ID NO: 1-112, fragments thereof, and complements of both.

The present invention also provides a plant comprising a disease resistance locus. Such alleles may be homozygous or heterozygous.

As used herein, reniform refers to any reniform variant or isolate. A cotton plant of the present invention can be resistant to one or more nematodes capable of causing disease similar to reniform. In one aspect, the present invention provides plants resistant to reniform as well as methods and compositions for screening cotton plants for resistance or susceptibility to reniform, caused by the genus *Rotylenchulus*. In a preferred aspect, the present invention provides methods and compositions for screening cotton plants for resistance or susceptibility to *Rotylenchulus reniformis*.

In one aspect, this invention could be used on any plant. In another aspect, the plant is selected from the genus *Gossypium*. In another aspect, the plant is selected from the species *Gossypium hirsutum*. In a further aspect, the plant is selected from the subspecies *Gossypium hirsutum* L. In an additional aspect, the plant is from the group *Gossypium arboreum* L., otherwise known as tree cotton. In another aspect, the plant is from the group *Gossypium barbadense* L., otherwise known as American pima or Egyptian cotton. In another aspect, cotton plant is from the group *Gossypium herbaceum* L., otherwise known as levant cotton. *Gossypium* or cotton plants can include hybrids, inbreds, partial inbreds, or members of defined or undefined populations.

Plants of the present invention can be very resistant, resistant, substantially resistant, moderately-resistant, comparatively resistant, partially resistant, moderately susceptible, or susceptible to a given disease, or display other variations in degrees of resistance or susceptibility.

In a preferred aspect, the present invention provides a plant to be assayed for resistance or susceptibility to disease by the Infection Index Method, or by any other method to determine whether a plant is very resistant, resistant, substantially resistant, moderately resistant, comparatively resistant, partially resistant, moderately susceptible, or susceptible to a given disease, or display other variations in degrees of resistance or susceptibility.

In another aspect, the cotton plant can show a comparative resistance compared to a non-resistant control cotton plant. In this aspect, a control cotton plant will preferably be genetically similar except for the disease resistance allele or alleles in question. Such plants can be grown under similar conditions with equivalent or near equivalent exposure to the pathogen.

A disease resistance QTL of the present invention may be introduced into an elite line. An "elite line" is any line that has resulted from breeding and selection for superior agronomic performance.

A resistance QTL of the present invention may also be introduced into an elite cotton plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in plants.

A disease resistant QTL allele or alleles can be introduced from any plant that contains that allele (donor) to any recipient plant. In one aspect, the recipient plant can contain additional disease resistance loci. In another aspect, the recipient plant can contain a transgene. In another aspect, while maintaining the introduced QTL, the genetic contribution of the plant providing the disease resistance QTL can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that genetic material contains the resistance locus or loci of interest.

It is further understood that a plant of the present invention may exhibit the characteristics of any relative maturity group. In an aspect, the maturity group is selected from the group consisting of early maturing varieties, mid season maturing varieties, and full season varieties.

An allele of a QTL can comprise multiple genes or other genetic factors even within a contiguous genomic region or linkage group, such as a haplotype. As used herein, an allele of a disease resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular disease locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice.

However, those of skill in the art should, in light of the present disclosure, appreciate that many changes can be made in the specific embodiments disclosed herein and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Determining Infection Indices

Soil Sampling and DNA Extraction

To ensure that soil sampled from a given location was representative of the soil at that location, four 200-300 gm soil samples were gathered from various positions at that location, combined, and thoroughly mixed to form a "bulked sample". Using the UltraClean™ Mega Soil DNA Isolation Kit, and following the manufacturer's protocols, DNA was extracted from one or more 5-7 gm soil subsamples taken from the bulked sample.

Total DNA Quantification

Following extraction of DNA from soil samples, the total amount of DNA in the soil sample was quantified using a Quant-iT™ PicoGreen® kit and following the manufacturer's protocols. A four-point standard curve was generated using 10 μL of salmon sperm DNA, at various concentrations, added to 40 μl TE buffer and 50 μL of the PicoGreen® reagent. The amount of DNA detected in the soil sample was mapped to the standard curve to arrive at the total amount of DNA isolated from the soil sample (Table 1).

TABLE 1

Contents of DNA quantification assays (μl).

| Reagent | PCR Product | DNA of Known Concentration |
|---|---|---|
| DNA | 2 | 10 |
| TE buffer | 48 | 40 |
| 200-fold Diluted Picogreen ® Reagent | 50 | 50 |
| Total: | 100 | 100 |

Reniform ITS1 Gene Quantification

The amount of reniform ITS1 gene in the DNA isolate extracted from the soil sample above was quantified by Real Time PCR. A 100 fold dilution of the isolate was created and 2 μL of that dilution were mixed with 3 μL of ITS1 primer-probe mix, and 5 μL TaqMan® Universal PCR Mastermix. The contents of the primer-probe mix are displayed in Table 2 and the contents of the subsequent PCR reaction are displayed in Table 3.

TABLE 2

Contents of the reniform ITS1 primer-probe mix used to quantify reniform nematode.

| [Reagent] | Sequence (5'→ 3') | Volume (μL) |
|---|---|---|
| 100 μM Forward Primer | GCTGCGCTGGCGTCTCT | 330 |
| 100 μM Reverse Primer | GGACGTAGCACATTAGCAATGC | 330 |

TABLE 2-continued

Contents of the reniform ITS1 primer-probe mix used to quantify reniform nematode.

| [Reagent] | Sequence (5'→ 3') | Volume (μL) |
|---|---|---|
| 100 μM Probe | CGTTGTTGAGCAGTTGT | 67 |
| Water | — | 9273 |
| | Total: | 10000 |

TABLE 3

Contents of the PCR reaction used to quantify reniform nematode.

| Component | Vol (μL) |
|---|---|
| TaqMan ® Universal PCR Mastermix | 5 |
| ITS Primer-Probe Mix | 3 |
| Diluted DNA | 2 |
| Total: | 10 |

After reactions were assembled, PCR was performed in an ABI 7900HT Sequence Detection System using standard techniques known in the art to amplify the sequence specific to the two primers. The amount of total DNA and the amount of DNA amplified in the PCR reaction by the ITS primer-probe mix were compared to a standard curve generated by the ABI 7900HT using 10-fold dilutions of reniform ITS plasmid. This comparison provided an estimate of the total amount of DNA and amount of reniform ITS1 DNA in the sample.

Infection Index Calculation

The amount of total DNA and the amount of DNA amplified in the PCR reaction were used to calculate the infection index for that sample using the following formula:

$$\text{infection index} = \frac{\text{ng of reniform } ITS1 \text{ gene DNA}}{\text{ng of total DNA}}$$

Example 2

Demonstration of the Relationship Between Infection Index Vs. Baermann Funnel Extraction Technique Ninety gram soil samples were collected from the rhizospheres of cotton lines exhibiting varying levels of reniform resistance in reniform-infested fields. From each 90 gm sample, a 5-7 gm subsample was taken to assess the level of infestation via the Infection Index Method. The remaining 83-85 gm of soil was analyzed via the Baermann Funnel Extraction Technique (BFET). A regression analysis produced the following linear model:

Log(Nem/g)=0.7866+1.2883 Log(ITS/DNA)

with $R^2$=0.742 and where g=grams, Nem=the number of reniform nematodes determined by BFET, ITS=the predicted ng of reniform ITS1 5.8S rRNA gene sequence detected by Taqman® Real time PCR and DNA=the ng of total DNA determined by standard DNA quantification protocol.

To demonstrate the correlation between BFET and the Infection Index Method, reniform juveniles that were collected via BFET for each soil sample were suspended in 1.5 mL water in small tubes and counted manually under a microscope. Each of these samples was then assessed via the Infection Index Method, wherein the DNA from each tube was extracted as if it were a 5-7 g sample of soil, as described previously. A regression analysis produced the following linear fit model:

Log(Nem/g)=0.3156+3.1713 Log(ITS/DNA)

with $R^2$=0.779 and where g=grams, Nem=the number of reniform nematodes determined by BFET, ITS=the predicted ng of reniform ITS1 5.8S rRNA gene sequence detected by Taqman® Real Time PCR and DNA=the ng of total DNA detected by DNA quantification protocol.

Thus, the Infection Index Method correlates ($R^2$>0.74) with the number of reniform nematodes in a sample of matter whether it is a soil sample or a substantially purified suspension of reniform nematodes.

Example 3

Using the Infection Index Method to Monitor Reniform Infection Among Different Growing Areas In one embodiment of this invention, the Infection Index Method can be used to determine the level of reniform infestation (inoculum density) in different growing areas. From 8 cotton fields near various cities in the Cotton Belt (Table 4), five 200-300 gm soil samples were collected from representative locations within each field. The five samples collected at a single field were then bulked, thoroughly mixed and thereafter considered to represent the collective soil for that growing area.

From each of the 8 samples representing a different field, a 5 gm subsample was processed through the Infection index Method, as described in Example 1, while 100 gm of the remaining soil was processed through BFET. Unfortunately, due to the inadvertent loss of soil from the samples taken at Havana and Leesburg, insufficient amounts remained to perform BFET for those growing areas. The data generated was entered into Table 4 and a regression analysis was performed to reveal the relationship between the results generated from the two methods ($R^2$=0.81).

TABLE 4

Infection Index Method results verses Baermann Funnel Extraction Technique results for several growing areas.

| | Reniform per 100 gm of soil | |
|---|---|---|
| Growing Area | Baermann Funnel Extraction Technique | Infection Index Method |
| Caledonia, MS | 1360 | 1154 |
| Burtihatchie, MS | 129 | 105 |
| Starkville, MS | 381 | 52 |
| Minturn, SC | 592 | 638 |
| Laurinburg, NC* | 1151* | 2181 |
| Laurinburg, NC | 322 | 125 |
| Havana, , FL | 0** | 301 |
| Leesburg, FL | 0** | 285 |

*Many dead or inactive nematodes observed
**Sample size too small (60 gm) for extraction Thus, the Infection Index Method can be used to determine the presence of target organisms at various growing areas distributed across a wide geographical range. Furthermore, the discrepancy between the Infection Index Method and BFET results for the first Laurinburg, N.C. location listed in Table 4 highlight the improved accuracy of the Infection Index Method over previous methods described in the art because, at that location, many dead or inactive nematodes were observed. Those skilled in the art realize that BFET results tend to be underestimates of nematode infection at locations where many of the nematodes are dead or inactive at the time samples are taken. Thus, the much higher number of reniform detected by the Infection Index Method compared to BFET at the first Laurinburg location illustrates that, unlike current methods described in the art, the Infection Index Method is not confounded by disproportionate numbers of dead or inactive nematodes in a soil sample.

Table 4 also illustrates the ability of the Infection Index Method to accurately determine infestation levels under conditions where soil sample sizes are too small for other methods, as clear results were gathered with the Infection Index Method for locations where insufficient soil was available to perform BFET.

Infection indices can be determined for each growing area before planting, after planting, during the growing season, after harvest, and/or in any combination thereof. An average infection index can be determined for a particular growing area for a specific point in time, or over a period of time, based on one or more samples taken sequentially from that growing area over time.

In one embodiment, the average infection index for one or more growing areas can be compared to determine and/or contrast the level of infestation among them. This information can be used to develop treatment priorities and strategies for treating infestation among growing areas, make better crop production and management decisions, and determine the ability of plants to resist disease.

For example, infection indices determined before planting can provide a "baseline" level of infestation for a growing area, allowing a grower to decide whether to plant at that location, or decide which variety of a certain crop would be better suited for that environment, based on the grower's needs. For instance, if the average reniform infection index for a field is particularly high, a grower may select to plant a particularly reniform resistant variety at that growing area, or perhaps elect to leave it fallow for a period of time.

In the same way, a grower can base decisions about what variety of crop, if any, to plant in a particular growing area the following year based on infection indices measured at that growing area, either before planting, during the growing season, or after harvest, in the previous year.

Thus, those working in the crop seed industry can rapidly make accurate recommendations about which cultivars are better suited to one growing area verses another, or make analogous comparisons and decisions about which cultivars to plant at different locations within the same growing area.

The infection index can be combined with VART (Variable Application Rate Technologies) in order to make site specific decisions and to allocate resources for chemical treatments appropriately, based on the level of reniform infestation at different growing areas. For instance, resources comprising chemicals, equipment, and/or manpower, or other resources, or combinations thereof, could be dispatched in greater concentration to one growing area as opposed to another depending on the initial infestation level before planting, as determined by the Infection Index Method. In analogous ways, these decisions about resource allocation can be made to treat, or anticipate optimal treatments, of plants at various locations within a growing area while plants are growing, and resources dispatched accordingly.

In another embodiment, the average infection index of various growing areas can be used to monitor or scout the change in infestation levels at multiple growing areas over time. As these levels change, resources could be allocated to different growing areas in anticipation of predicted changes in infestation level trends.

Example 4

Using the Infection Index Method to Monitor Reniform Infection within a Given Geographical Location In one embodiment of this invention, the Infection Index Method can be used to determine the level of reniform infestation for a single growing area, or among multiple locations within a single growing area.

Soil is collected at multiple locations within a given growing area and processed through the Infection Index Method as described in Example 1. infection indices can be determined for each sample before planting, after planting, during the growing period of the plants, after harvest, and/or in any combination thereof.

In one embodiment, an average infection index can be determined for a particular location in a growing area over a period of time based on one or more samples taken from that location at one or more points in time. Alternatively, the growing area may be divided into sections, each consisting of one or more sample locations, and an average infection index of that section can be determined by averaging the infection indices determined from one or more samples taken within that section.

Table 5 illustrates how infection index data generated from soil samples taken from multiple locations within a growing area, like that generated from a cultivated cotton field near Parksdale, Ark., can be mapped onto a graphical representation of the growing area. This reveals how infestation levels differed among locations within the field at a particular point in time.

TABLE 5

A representation of the pre-planting assessment of reniform nematode infestation (number of reniform per pint of soil) across multiple locations in a field near Parksdale, AR.

|   | A | B | C | D | E | F | G |
|---|---|---|---|---|---|---|---|
| 1 | 4735 | 3906 | 3095 | 4811 | 10862 | 11236 | 8333 |
| 2 | 4037 | 6516 | 4591 | 5404 | 12153 | 7577 | 11985 |
| 3 | 5042 | 5504 | 4389 | 5953 | 6506 | 9931 | 7685 |
| 4 | 4425 | 5327 | 11990 | 12558 | 13461 | 7116 | 14707 |

High Infestation
Moderate Infestation
Low Infestation

One of the problems of generating reliable reniform disease evaluation data is the lack of uniform distribution of the pest in a given field or population. In one embodiment of this invention, the Infection Index Method is used to monitor the change of infestation levels for a plot, location, section, or multiple locations or sections of a growing area over time, which allows a grower to track the spread of infestation across different locations within the field.

For instance, by monitoring the change in infestation levels over time, a grower or scientist can determine whether differences in infestation levels at some point is unduly influenced by differences in initial infestation levels, or to some other factor, such as plant resistance to reniform nematode infection.

Previously, it was difficult to accurately gauge the effects of a given treatment on the spread of reniform infestation across locations due to the considerable investments in time and resources necessary to assay each growing area or location within a growing area before, during, and after the treatment. The results of such studies, for example, could be easily confounded by differences in initial infestation levels across locations, or growing areas, unless costly measures were taken to account for those initial differences. The Infection Index Method, on the other hand, provides a feasible way to correct for such differences providing a relatively quick and inexpensive way to assay infestation on a location-by-location, or section-by-section basis at multiple times for substantially all locations in a growing area.

This information can be used to develop treatment priorities and strategies for treating infection among locations within a growing area. For example, infection indices determined for specific locations, or sections of the field, before planting can provide a baseline level of infection for that location, allowing a grower to decide which variety of crop, if any, to plant at a particular location in the field based on the infection index previously determined for that location.

The Infection Index Method can also be used in conjunction with VART to anticipate the allocation of resources to different locations within a growing area in preparation of treating plants before they are planted or while they are growing. For instance, resources comprising chemicals, equipment, and/or manpower, or other resources, or combinations thereof, could be dispatched in greater concentration to one location or section of a field as opposed to another depending on its infection index before planting. In the same way, these decisions about resource allocation can be made to treat, or anticipate desired treatments, of plants in a growing area while plants are growing, and resources dispatched accordingly.

In another embodiment, the average infection index of a section of a growing area can be used to monitor the change in infestation levels over time. As these levels change, resources could be allocated to different sections of a growing area in anticipation of future infection level trends.

Example 5

Demonstration that the Infection Index Method can be Used to Reliably Phenotype Plants for Resistance to Reniform Nematode This example describes how the Infection Index Method can be used to determine the number of reniform nematodes present in a plant's rhizosphere and how that information can be used to phenotype the plant for its ability to resist reniform nematode infection.

Establishment of Relatively Resistant and Susceptible Phenotypes

A population of 7-10 day-old *Gossypium arboretum* Lonren-1 and Lonren-2 lines were inoculated with approximately 2500 juvenile reniform nematodes per plant and propagated in a growth chamber for 45-50 days, after which approximately 90 g of soil was separately collected from the rhizosphere of each plant and the level of reniform nematode infestation was quantified for each plant using standard BFET techniques.

The plants with the highest levels of reniform nematodes were considered thereafter to have a relatively "susceptible" phenotype, and those with the lowest number of reniform nematodes were thereafter considered to have a relatively "resistant" phenotype for subsequent analyses. All plants were grown under identical environmental conditions.

Data Collection

The six most susceptible and six most resistant lines were planted in a growth chamber and each plant inoculated with approximately 2500 nematodes, with four replications. Two other plants of each phenotype were not inoculated to serve as live controls and two pots containing soil but no plants were inoculated to serve as fallow controls. All plants were harvested after two months and soil collected from the rhizosphere of each plant. This time, in addition to the 90 g of soil collected to quantify nematode infection via the BFET, 5-7 g samples were also collected to quantify nematode infection via the Infection Index Method.

Results

The average infection indices for the two phenotypes and the controls are presented in Table 6 (an infection index of 73.72 for one of the inoculated, susceptible plants was excluded as an outlier based on an ANOVA analysis). On average, the susceptible phenotypes had infection indices approximately 23 times higher than plants with resistant phenotypes, demonstrating the ability of the Infection Index Method to assess the ability of plants to resist nematode infection (note that including the outlier would have made this difference even greater).

TABLE 6

Results of infection indices calculated on reniform resistant and reniform susceptible phenotypes.

| Genotype | Treatment | Average Infection Index* |
|---|---|---|
| Resistant | Inoculated | 0.76 |
| | Control | 0.00 |
| Susceptible | Inoculated | 17.18 |
| | Control | 0.01 |
| Fallow | Inoculated | 0.02 |

*infection index = $\frac{\text{ng of reniform ITS1 gene DNA}}{\text{ng of total DNA}}$ In this manner, the infection index calculated for a sample of soil collected from the rhizosphere of a plant can serve as an indication of the plant's ability to resist reniform infection, and consequently, serve as the plant's effective phenotype. Thus, the infection index calculated for one plant, or a population of plants, can be compared to that of another plant, or population of plants, to compare and score relative levels of resistance.

This method then allows the user to compare relative resistance phenotypes among plants in a single growing area, or across growing areas in ways analogous to those which infection indices can be compared for locations within or among growing areas, as described in Examples 1-4. Changes in infection indices over time can reveal important information about the spread of infection in a population, or among populations. Moreover, the abilities of plant lines to resist infection can also be determined. For example, infection indices calculated for plants in a population at a specific point in the growing season can be compared to pre-planting infection indices to more accurately phenotype a plant's ability to resist infection. It allows the user to determine how much of the difference between two plants' infection indices is due to differences in the plants' abilities to actually resist infection verses differences in preplanting levels of reniform infestation in the soil at the locations where the plants were planted. Even changes in a plant's ability to resist infection over time can be determined.

This information can also be very important in helping growers or breeders determine how best to allocate resources or apply treatments to plants in response to reniform infestation and allow plant breeders to more accurately gauge a plant's ability to resist infection.

Example 6

The Infection Index Method can be Used on Species Other than Reniform Nematode Conical vials (50 mL), each containing 5 gm of soil free of root knot nematode (RKN), were assembled and a specific number of RKN J2 stage juveniles were counted manually and mixed with the soil within each vial. The number of RKN added to each vial was either 0, 10, 100, 250, 500, 100, 1500, 2000, 2500, 5000, 7500, or 10,000, with 3 replications of each number, for a total of 36 vials. Each 5 gm sample in each vial was stored at room temperature for 3 days, then the amount of total DNA and the amount of RKN DNA amplified in a PCR reaction was calculated for each sample following the process described in Example 1, except that primers and probes specific to RKN were used (Table 7). The infection index was then calculated for each sample using the following formula:

$$\text{infection index} = \frac{\text{ng of } RKN\ ITS1 \text{ gene DNA}}{\text{ng of total DNA}}$$

TABLE 7

Concentrations of RKN ITS1 primer-probe mix components used in the Infection Index Method to quantify RKN infestation.

| Reagent | Sequence (5'→ 3') | Vol. (μL) |
|---|---|---|
| 100 mM Forward Primer | CGT AAC TTA CAC TCA GAT CTG TCC AAT | 330 |
| 100 mM Reverse Primer | GGT ACC CAA ACG GTG TTA GCA TTT | 330 |
| 100 mM Probe | TAC ACG TGA GCC ATA CTC AAA TGC CCA A | 67 |
| Water | — | 9273 |
| | Total: | 10000 |

Table 8 compares the log of the infection index averaged for the 3 replications of each inoculum level to the number of nematodes manually counted out in the inoculum.

TABLE 8

Infection indices calculated for samples containing specified numbers of RKN.

| Number of RKN in soil | Log of Infection Index | StDev |
|---|---|---|
| 0 | 0 | 0 |
| 10 | −1.7276 | 0.2268 |
| 100 | −0.5857 | 0.1152 |
| 250 | 0.5911 | 0.0984 |
| 500 | 1.1138 | 0.1603 |
| 1,000 | 1.679 | 0.3536 |
| 1,500 | 1.8025 | 0.1464 |
| 2,000 | 2.1834 | 0.1174 |
| 2,500 | 2.1402 | 0.0243 |
| 5,000 | 2.8862 | 0.2988 |
| 7,500 | 3.1898 | 0.1574 |
| 10,000 | 3.1376 | 0.0231 |

Table 8 reveals the accuracy of the Infection Index Method for quantifying the known number of RKN in a sample of soil ($R^2$=99%), as well as the applicability of the method to organisms other than reniform. It is anticipated that other organisms could be quantified in this manner using primers and probes specific to them.

It is anticipated that the Infection Index Method can be used to quantify the number of nematodes infecting plant species other than cotton. For instance, nematode infestation levels of soybean or corn growing areas could also be determined using the primers and probes described in Table 2 (reniform) and/or Table 7 (RKN).

One non-limiting, prophetic example of the wide applicability of the Infection Index Method would be using it to determine the level of *Diabrotica virgifera* infestation in a corn field using DNA sequences specific to *Diabrotica virgifera*.

Example 7

The Infection Index Method is Specific to the Organism Targeted by Primer and Probe Selection and can be Used to Quantify Infestation by Multiple Species, Simultaneously Five pots containing tomato and cotton seedlings were inoculated with 2500 RKN eggs. A second set of five pots containing tomato and cotton seedlings were inoculated with 2500 reniform Juveniles. After 60 days, four 5-7 gm sub-samples of soil from the rhizosphere of each plant in each pot were collected and composited. The total DNA and DNA amplified in a PCR reaction specific for RKN using the probes and primers described in Table 7 were determined and used to calculate an infection index for each plant.

Next, a series of 100 gm soil samples were then collected from a reniform-infected field near Lubbock Tex. Although the Lubbock field was infected with reniform, no RKN was detected there. From each 100 gm sample, 5-7 gm sub-samples were processed through the Infection Index Method using the RKN-specific primers and probes described in Table 7.

The log of each infection index calculated for each sample was then determined (Table 9). A regression analysis of the data produced the following linear fit model:

RKN per sample=313+1621 Log*(infection index)

with $R^2$=0.59. The number of predicted RKN per sample was then calculated using this equation and entered into Table 9.

TABLE 9

Infection indices calculated for samples from RKN-infested culture pots and Reniform-infested fields.

| Source | log (infection index) | Predicted #RKN/Sample |
|---|---|---|
| RKN culture pot | 0.37 | 906.26 |
| RKN culture pot | 0.18 | 596.95 |
| RKN culture pot | 0.24 | 699.11 |
| RKN culture pot | 0.14 | 535.05 |
| RKN culture pot | 0.95 | 1856.41 |
| REN culture Pot | 0 | 0 |
| REN culture Pot | 0 | 0 |
| REN culture Pot | 0 | 0 |
| REN culture Pot | 0 | 0 |
| REN culture Pot | 0 | 0 |
| Wilson, TX (Ren infested field) | 0 | 0 |
| Wilson, TX (Ren infested field) | 0 | 0 |
| Wilson, TX (Ren infested field) | 0 | 0 |
| Wilson, TX (Ren infested field) | 0 | 0 |

Table 9 reveals the specificity of the Infection Index Method for quantifying only RKN infestation levels when RKN-specific probes and primers are used. Thus, not only is the Infection Index Method efficient and accurate, but is also highly specific for quantifying only the organisms targeted by the primers and probes used in the process. In one embodiment of the invention, the Infection Index Method can be used to detect cross contamination between RKN and reniform-specified growing areas. In another embodiment, contamination by other organisms could be detected and quantified using probes and primers specific for those organisms.

The fact that results of the Infection Index Method are not confounded by the presence of non-target organisms in the soil reveals yet another embodiment of the invention. The relative infestation levels of more than one organism can be determined for a given location simultaneously. It is anticipated that a set of primers and probes specific for RKN could be combined with primers and probes specific to reniform in the same PCR reaction to determine the total amount of infestation by both organisms at the same time via the Infection Index Method.

In another embodiment of the invention, subsamples taken from the same location, or rhizosphere of the same plant, could be processed through the Infection Index Method separately, but simultaneously, to determine the level of RKN infestation verses the level of reniform infestation for that location or plant.

This example also reveals the novel concept of using the Infection Index Method to detect the amount of obligate endo-parasites, like RKN, present in the soil. Previous art fails to teach or suggest that such quantification is possible due to the presumption that it would be necessary to extract DNA from parasites living inside plant tissue. This example demonstrates the surprising result that it is indeed possible to quantify endo-parasite infestation by assaying soil collected from the rhizospheres of plants substantially nondestructively, presumably because the life cycle of the parasite includes some time outside of the plant tissue and not all of the parasites are at the same point of the life cycle at the same time. Thus, the Infection Index Method is a useful tool for quantifying the relative amount of obligate endo-parasites, like RKN.

It is also anticipated that the Infection Index Method could be used in conjunction with isothermal PCR techniques. Thus, one embodiment of this invention comprises using an infection index to determine the amount of target organisms in a sample without leaving the field or growing area.

Example 8

Prophetic Example of Using the Infection Index Method to Select for Reniform Resistant Plants Using Conventional Breeding Techniques The disease resistance of a plant can be gauged using the Infection Index Method described in Examples 1-6 and this information can be used to guide decisions about selecting plants to serve as parents in subsequent generations.

For example, crosses can be made between cotton lines and the progeny grown in soil infected with reniform. Using the Infection Index Method, the ability of the offspring to resist infection can be determined, as well as the ability of each parent line to produce offspring resistant to reniform infection.

This system can be used to determine which offspring and/or which parents to use in future crosses by continuing to select for favorable disease resistance phenotypes, as determined by the Infection Index Method, to generate reniform resistant lines. Any number of variations in selection schemes or breeding programs known in the art can be used in conjunction with the Infection Index Method, including, but not limited to, recurrent selection, pedigree selection, and/or single seed descent.

In one embodiment, the introgression of one or more resistance loci can also be achieved via repeated backcrossing to a recurrent parent, with a consistently resistant phenotype, accompanied by selection to retain the resistant phenotype of the recurrent donor parent. This backcrossing procedure is implemented at any stage in line development and occurs in conjunction with breeding for superior agronomic characteristics or one or more traits of interest, including transgenic and nontransgenic traits.

This method can also be used to discover new sources of resistance within or among germplasms.

Alternatively, a forward breeding approach is employed wherein a resistant phenotype can be monitored for successful introgression following a cross with a susceptible parent with subsequent generations phenotyped using the Infection Index Method to detect the resistant phenotype. This selection of the resistant phenotype can be done simultaneously with selection for one or more additional traits of interest, including transgenic and nontransgenic traits.

Example 9

Demonstration of how the Infection Index Method can be Used to Identify SNP Markers Associated with a Reniform Resistance Gene A mapping population was developed from crossing the reniform resistant parent LONREN-2 with reniform susceptible parent GV061 (ATCC Deposit # PTA-XXXX). A total of 135 near-isogenic lines (NILs) were developed for the mapping population. Ten replicates of each line were phenotyped for reniform resistance using the Infection Index Method as described in Example 1 and SNPs that were polymorphic in the NIL population were used to genotype each plant. Sequence capture techniques and Bulked Segregant Analysis (BSA) were then used to identify and map additional SNPs associated with resistance. A total of 112 SNPs capable of detecting the presence of reniform resistance and monitoring the introgression of the disease resistance locus were identified and mapped to the cotton genome in the region (Table 10). Although primers and probes are not provided for every SNP, one can order the components necessary to detect the disclosed SNPs from several options of vendors specializing in such services or simply create the appropriate primers and probes using methods requiring ordinary skill in the art.

TABLE 10

SNP markers on chromosome A11 capable of detecting reniform resistance
and monitoring the introgression of the disease resistance locus.

| SEQ ID NO | Chr. Position (cM) | SNP Position [1] | Allele 1 | Allele 2 | SEQ ID NO: Fwd Primer | Rev Primer | Probe 1 | Probe 2 |
|---|---|---|---|---|---|---|---|---|
| 1 | 145 | 253 | A | G | 113 | 182 | 251 | 320 |
| 2 | 152.2 | 253 | G | T | 114 | 183 | 252 | 321 |
| 3 | 163.6 | 122 | A | G | 115 | 184 | 253 | 322 |
| 4 | 172.2 | 143 | C | T | 116 | 185 | 254 | 323 |
| 5 | 158.4 | 325 | C | G | 117 | 186 | 255 | 324 |
| 6 | 142.5 | 303 | A | C | 118 | 187 | 256 | 325 |
| 7 | 166.4 | 125 | A | C | 119 | 188 | 257 | 326 |
| 8 | 147 | 382 | A | G | 120 | 189 | 258 | 327 |
| 9 | 143 | 367 | A | G | 121 | 190 | 259 | 328 |
| 10 | 181.1 | 409 | A | T | 122 | 191 | 260 | 329 |
| 11 | 150.7 | 447 | A | G | 123 | 192 | 261 | 330 |
| 12 | 165.5 | 209 | A | G | 124 | 193 | 262 | 331 |
| 13 | 171.3 | 354 | C | T | 125 | 194 | 263 | 332 |
| 14 | 169.8 | 254 | A | T | 126 | 195 | 264 | 333 |
| 15 | 183.5 | 218 | A | T | 127 | 196 | 265 | 334 |
| 16 | 163.9 | 449 | C | T | 128 | 197 | 266 | 335 |
| 17 | 160.8 | 220 | G | * | 129 | 198 | 267 | 336 |
| 18 | 160.1 | 385 | A | G | 130 | 199 | 268 | 337 |
| 19 | 145.9 | 333 | A | T | 131 | 200 | 269 | 338 |
| 20 | 183.5 | 322 | A | G | 132 | 201 | 270 | 339 |
| 21 | 180.1 | 166 | A | T | 133 | 202 | 271 | 340 |
| 22 | 180.1 | 219 | C | T | 134 | 203 | 272 | 341 |
| 23 | 160.1 | 59 | A | T | 135 | 204 | 273 | 342 |
| 24 | 182.4 | 525 | C | G | 136 | 205 | 274 | 343 |
| 25 | 178.5 | 221 | C | T | 137 | 206 | 275 | 344 |
| 26 | 159.2 | 272 | A | T | 138 | 207 | 276 | 345 |
| 27 | 150.7 | 149 | A | C | 139 | 208 | 277 | 346 |
| 28 | 165.7 | 310 | C | G | 140 | 209 | 278 | 347 |
| 29 | 160.1 | 520 | A | T | 141 | 210 | 279 | 348 |
| 30 | 159.8 | 62 | A | G | 142 | 211 | 280 | 349 |
| 31 | 182.2 | 192 | G | T | 143 | 212 | 281 | 350 |
| 32 | 181.2 | 255 | A | G | 144 | 213 | 282 | 351 |
| 33 | 174.4 | 381 | A | G | 145 | 214 | 283 | 352 |
| 34 | 160.1 | 107 | A | C | 146 | 215 | 284 | 353 |
| 35 | 150.7 | 171 | A | G | 147 | 216 | 285 | 354 |
| 36 | 180.1 | 356 | A | G | 148 | 217 | 286 | 355 |
| 37 | 150.7 | 323 | C | T | 149 | 218 | 287 | 356 |
| 38 | 171.2 | 188 | A | G | 150 | 219 | 288 | 357 |
| 39 | 174.9 | 188 | T | C | 151 | 220 | 289 | 358 |
| 40 | 174.9 | 683 | G | A | 152 | 221 | 290 | 359 |
| 41 | 166.6 | 619 | C | T | 153 | 222 | 291 | 360 |
| 42 | 175.5 | 338 | G | A | 154 | 223 | 292 | 361 |
| 43 | 174.9 | 152 | T | G | 155 | 224 | 293 | 362 |
| 44 | 170.4 | 163 | G | A | 156 | 225 | 294 | 363 |
| 45 | 174.9 | 312 | A | G | 157 | 226 | 295 | 364 |
| 46 | 167.7 | 82 | C | T | 158 | 227 | 296 | 365 |
| 47 | 175.2 | 708 | C | A | 159 | 228 | 297 | 366 |
| 48 | 174.9 | 225 | G | C | 160 | 229 | 298 | 367 |
| 49 | 160.1 | 197 | G | T | 161 | 230 | 299 | 368 |
| 50 | 170.7 | 106 | T | C | 162 | 231 | 300 | 369 |
| 51 | 174.9 | 207 | A | G | 163 | 232 | 301 | 370 |
| 52 | 174.9 | 553 | A | G | 164 | 233 | 302 | 371 |
| 53 | 168.9 | 152 | C | T | 165 | 234 | 303 | 372 |
| 54 | 174.6 | 208 | T | C | 166 | 235 | 304 | 373 |
| 55 | 170.7 | 531 | T | C | 167 | 236 | 305 | 374 |
| 56 | 174.9 | 139 | C | T | 168 | 237 | 306 | 375 |
| 57 | 174.6 | 159 | A | G | 169 | 238 | 307 | 376 |
| 58 | 162 | 51 | G | A | 170 | 239 | 308 | 377 |
| 59 | 170.7 | 139 | G | A | 171 | 240 | 309 | 378 |
| 60 | 175.5 | 318 | A | G | 172 | 241 | 310 | 379 |
| 61 | 174.9 | 143 | A | G | 173 | 242 | 311 | 380 |
| 62 | 175.5 | 105.0 | T | A | 174 | 243 | 312 | 381 |
| 63 | 170.7 | 160 | C | G | 175 | 244 | 313 | 382 |
| 64 | 172.6 | 168 | G | T | 176 | 245 | 314 | 383 |
| 65 | 174.9 | 565 | T | G | 177 | 246 | 315 | 384 |
| 66 | 170.1 | 165 | C | T | 178 | 247 | 316 | 385 |
| 67 | 174.9 | 118 | C | T | 179 | 248 | 317 | 386 |
| 68 | 170.7 | 96 | C | A | 180 | 249 | 318 | 387 |
| 69 | 170.4 | 609 | G | A | 181 | 250 | 319 | 388 |
| 70 | ** | 131 | A | G | — | — | — | — |
| 71 | ** | 205 | G | C | — | — | — | — |
| 72 | 174.9 | 739 | T | A | — | — | — | — |

TABLE 10-continued

SNP markers on chromosome A11 capable of detecting reniform resistance and monitoring the introgression of the disease resistance locus.

| SEQ ID NO | Chr. Position (cM) | SNP Position[1] | Allele 1 | Allele 2 | Fwd Primer | Rev Primer | Probe 1 | Probe 2 |
|---|---|---|---|---|---|---|---|---|
| 73 | 174.9 | 186 | C | T | — | — | — | — |
| 74 | 174.9 | 262 | G | T | — | — | — | — |
| 75 | 174.9 | 270 | A | T | — | — | — | — |
| 76 | 174.9 | 419 | C | A | — | — | — | — |
| 78 | 167.7 | 121 | T | C | — | — | — | — |
| 77 | 167.7 | 26 | A | G | — | — | — | — |
| 79 | 175.2 | 760 | C | A | — | — | — | — |
| 80 | 174.9 | 286 | A | T | — | — | — | — |
| 81 | 174.6 | 264 | A | G | — | — | — | — |
| 82 | 174.6 | 316 | T | C | — | — | — | — |
| 83 | 168.9 | 190 | G | A | — | — | — | — |
| 84 | 168.9 | 394 | T | A | — | — | — | — |
| 85 | 168.9 | 431 | A | T | — | — | — | — |
| 86 | 168.9 | 469 | A | G | — | — | — | — |
| 87 | 168.9 | 489 | T | C | — | — | — | — |
| 88 | 168.9 | 573 | G | A | — | — | — | — |
| 89 | 168.9 | 580 | G | T | — | — | — | — |
| 90 | 174.9 | 72 | G | A | — | — | — | — |
| 91 | 174.9 | 76 | T | C | — | — | — | — |
| 93 | 170.7 | 227 | C | T | — | — | — | — |
| 94 | 170.7 | 269 | A | G | — | — | — | — |
| 95 | 170.7 | 285 | A | C | — | — | — | — |
| 96 | 170.7 | 294 | A | G | — | — | — | — |
| 92 | 170.7 | 72 | A | G | — | — | — | — |
| 98 | 174.9 | 201 | A | G | — | — | — | — |
| 99 | 174.9 | 246 | T | C | — | — | — | — |
| 97 | 174.9 | 36 | C | T | — | — | — | — |
| 102 | 174.6 | 185 | G | A | — | — | — | — |
| 100 | 174.6 | 51 | G | C | — | — | — | — |
| 101 | 174.6 | 52 | T | C | — | — | — | — |
| 103 | 174.9 | 53 | A | G | — | — | — | — |
| 104 | 175.5 | 370 | G | A | — | — | — | — |
| 105 | 175.5 | 252 | G | A | — | — | — | — |
| 106 | 175.5 | 256 | A | G | — | — | — | — |
| 107 | 175.5 | 326 | C | A | — | — | — | — |
| 108 | 174.9 | 193 | T | A | — | — | — | — |
| 109 | 174.9 | 665 | C | T | — | — | — | — |
| 110 | ** | 3 | C | T | — | — | — | — |
| 111 | ** | 5 | G | A | — | — | — | — |
| 112 | 174.9 | 72 | A | G | — | — | — | — |

* a single nucleotide deletion
** exact location not determined
[1] nucleotide position in the indicated SEQ ID NO.

Example 10

Detecting Reniform Resistance and Monitoring the Introgression of the Resistance Locus from One Plant Line into Another Using SNP Markers A reniform resistant parent, such as LONREN-2, and a reniform susceptible parent, such as GV061 can be phenotyped for their ability to resist reniform infection using the Infection Index Method described in Examples 1-5. Alternatively, the Baermann Funnel Extraction Technique, or another reniform resistance phenotyping method, can be used.

Following phenotyping, the genotypes of the parents would be determined with respect to one or more markers linked to the resistance selected from Table 10. Alternatively, any DNA marker that falls within the genomic region between the public markers CGR6333 and BNL1231b can be used.

Next, the resistant parent and the susceptible parent would be crossed. In one embodiment of this invention, the genotype of the offspring would then be associated with the phenotype of the parents by comparing the genotype of the offspring at one or more marker loci selected from Table 10, or any DNA marker that falls within the genomic region between the public markers CGR6333 and BNL1231b, to the genotype of the parents at one or more marker loci. Individuals that share SNP alleles for those markers with the resistant parent would then be selected for advancement in the breeding program. Individuals with SNP alleles for those markers that do not match the resistant parent, or that do match the susceptible parent, could be discarded.

This process saves the laborious and time consuming process of phenotyping by hand the progeny from crosses with these parents to verify the resistant or susceptible individuals in the progeny population.

This invention can be used on populations other than those specifically described in this application without altering the methods described herein. Although different parents may have different genotypes at different markers, the method of using this invention is fundamentally identical.

A plant breeder can select resistant genotypes, as determined by the genotype of the resistant parent, at one or more markers provided in Table 10, or any marker that maps between the public markers CGR6333 and BNL1231b, to select plants for reniform resistance arising from the donor while selecting for the recipient genome in adjacent chromosome regions. In practice, this reduces the amount of linkage drag from the donor genome that may be associated with undesirable agronomic or fiber quality properties.

The introgression of one or more resistance loci is achieved via repeated backcrossing to a recurrent parent accompanied by selection to retain one or more reniform resistance loci from the donor parent. This backcrossing procedure is implemented at any stage in line development and occurs in conjunction with breeding for superior agronomic characteristics or one or more traits of interest, including transgenic and nontransgenic traits.

Alternatively, a forward breeding approach is employed wherein one or more reniform resistance loci can be monitored for successful introgression following a cross with a susceptible parent with subsequent generations genotyped for one or more reniform resistance loci and for one or more additional traits of interest, including transgenic and non-transgenic traits.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are, to the extent necessary, incorporated herein by reference in their entireties. As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents

What is claimed:

1. A method of determining a relative amount of nematodes in a sample of soil material, the method comprising:
   (a) determining a total amount of DNA in the soil material, by isolating DNA from the rhizosphere of a plant;
   (b) assaying for a presence of at least one DNA sequence in the DNA isolated from the rhizosphere of the plant that is specific to the nematode to quantify an amount of target nematode-specific DNA in the soil material; and,
   (c) calculating a ratio of nematode-specific DNA to total amount of DNA corresponding to the relative amount of the nematode in the soil material;
   wherein said nematode is an endo-parasitic nematode.

2. The method of claim 1 further comprising comparing said ratio to a standard to determine the number of nematodes in said sample.

3. The method of claim 1 wherein the nematodes are a plant pathogen.

4. The method of claim 1 wherein the nematodes are reniform nematodes.

5. The method of claim 1 wherein the nematodes are root knot nematodes.

6. The method of claim 1 wherein the ratio is used to select at least one treatment to apply to at least one location in a growing area, wherein the treatment is a chemical.

7. The method of claim 6 where the chemical is a nematocide.

8. A method of treating a location with pesticides comprising:
   (a) calculating a ratio of an amount of a nematode-specific nucleic acid to a total amount of nucleic acid isolated from the rhizosphere of a plant (a plant or soil sample) collected at a location, wherein said nematode-specific nucleic acid is from an endo-parasitic nematode, and
   (b) applying a pesticide to the location in proportion to the ratio calculated in (a).

9. The method of claim 1, wherein the ratio is used to represent the ability of a plant at a location where the sample of soil material was taken to resist infection by the endo-parasitic nematode.

10. The method of claim 9, wherein the ratio is used to decide whether to use the plant or its progeny in a breeding program.

11. The method of claim 9, wherein the plant is a cotton plant.

* * * * *

UNITED STATES PATENT AND TRADEMARK OFFICE
CERTIFICATE OF CORRECTION

| | | |
|---|---|---|
| PATENT NO. | : 8,686,219 B2 | Page 1 of 1 |
| APPLICATION NO. | : 12/901756 | |
| DATED | : April 1, 2014 | |
| INVENTOR(S) | : Muhammad Bhatti et al. | |

It is certified that error appears in the above-identified patent and that said Letters Patent is hereby corrected as shown below:

In the Claims

Column 200, Line 49, please delete "from the rhizosphere of a plant (a plant orsoil sample) collected at a location", and insert --from the rhizosphere of a plant collected at a location--

Signed and Sealed this
Eighth Day of July, 2014

Michelle K. Lee
*Deputy Director of the United States Patent and Trademark Office*